(12) United States Patent
Zhang et al.

(10) Patent No.: US 9,365,499 B2
(45) Date of Patent: Jun. 14, 2016

(54) 9-AMINOMETHYL SUBSTITUTED TETRACYCLINE COMPOUNDS

(75) Inventors: Hui Zhang, Jinan (CN); Yanyan Dong, Jinan (CN)

(73) Assignee: KBP Biosciences Co., Ltd., Jinan, Shandong Province (CN)

(*) Notice: Subject to any disclaimer, the term of this patent is extended or adjusted under 35 U.S.C. 154(b) by 167 days.

(21) Appl. No.: 14/234,420

(22) PCT Filed: Jul. 26, 2012

(86) PCT No.: PCT/CN2012/001001
§ 371 (c)(1),
(2), (4) Date: Jan. 23, 2014

(87) PCT Pub. No.: WO2013/013505
PCT Pub. Date: Jan. 31, 2013

(65) Prior Publication Data
US 2014/0179638 A1 Jun. 26, 2014

(30) Foreign Application Priority Data
Jul. 26, 2011 (CN) ........................ 2011 1 0222016

(51) Int. Cl.
| C07C 237/26 | (2006.01) |
| C07D 221/20 | (2006.01) |
| C07D 205/04 | (2006.01) |
| C07D 205/12 | (2006.01) |
| C07D 209/52 | (2006.01) |
| C07D 209/54 | (2006.01) |
| A61K 31/65 | (2006.01) |
| C07C 231/12 | (2006.01) |
| C07D 221/22 | (2006.01) |
| C07D 305/06 | (2006.01) |
| C07D 491/107 | (2006.01) |

(52) U.S. Cl.
CPC .............. *C07C 237/26* (2013.01); *A61K 31/65* (2013.01); *C07C 231/12* (2013.01); *C07D 205/04* (2013.01); *C07D 205/12* (2013.01); *C07D 209/52* (2013.01); *C07D 209/54* (2013.01); *C07D 221/20* (2013.01); *C07D 221/22* (2013.01); *C07D 305/06* (2013.01); *C07D 491/107* (2013.01); *C07C 2101/04* (2013.01); *C07C 2102/40* (2013.01); *C07C 2103/46* (2013.01); *C07C 2103/94* (2013.01)

(58) Field of Classification Search
CPC .. C07C 237/26; C07C 231/12; C07D 209/52; C07D 205/04; C07D 305/06; C07D 221/20; A61K 31/65
See application file for complete search history.

(56) References Cited

U.S. PATENT DOCUMENTS

| 7,326,696 B2* | 2/2008 | Nelson ................. C07C 237/26 514/152 |
| 2005/0026875 A1 | 2/2005 | Nelson et al. |
| 2008/0015169 A1 | 1/2008 | Nelson et al. |

FOREIGN PATENT DOCUMENTS

| CN | 1649582 | 8/2005 |
| CN | 101759604 | 6/2010 |
| JP | 2004502752 | 1/2004 |
| JP | 2007521290 | 8/2007 |
| JP | 2010513527 | 4/2010 |
| WO | 03075857 | 9/2003 |
| WO | WO 03/007587 A2 * | 9/2003 |
| WO | 2004038001 | 5/2004 |
| WO | 2004064728 | 8/2004 |
| WO | 2005009943 | 2/2005 |
| WO | 2013013505 | 1/2013 |

OTHER PUBLICATIONS

Zaragoza Dorwald, Side Reactions in Organic Synthesis, 2005, WILEY-VCH Verlag GmbH & Co. KGaA, Weinheim, Preface. p. IX.*
Marchand, Synthesis and Chemistry of Homocubanes, Bishomocubanes, and Trishomocubanes 1989, 89, pp. 1011-1033.*
China Patent Application No. CN201280037036.6 , Office Action dated Feb. 28, 2015.
Japanese Patent Application No. 2014-521914 , Japanese Office Action dated Dec. 24, 2014.
European Patent Application No. 12817774 , Supplementary European Search Report dated Nov. 25, 2014.
PCT/CN2012/001001, International Search Report dated Nov. 1, 2012.
International Application No. PCT/CN2012/001001 , "International Search Report", Nov. 1, 2012.
European Patent Application No. 12817774.8, Communication pursuant to Article 94(3) EPC dated Feb. 4, 2016; 4 pages.

* cited by examiner

*Primary Examiner* — Paul A Zucker
(74) *Attorney, Agent, or Firm* — Kilpatrick Townsend & Stockton LLP

(57) ABSTRACT

The present invention relates to 9-aminomethyl substituted tetracycline compounds represented by formula (I), or pharmaceutically acceptable salt, prodrug, solvate or isomer thereof, as well as a method for preparing these compounds and a pharmaceutical composition comprising the same. The present invention relates also to a use of these compounds in the preparation of a medicament for the treatment and/or prophylaxis of tetracycline drug-sensitive disease.

(I)

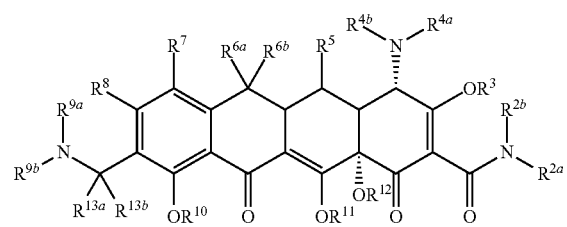

wherein, $R^{2a}$, $R^{2b}$, $R^3$, $R^{4a}$, $R^{4b}$, $R^5$, $R^{6a}$, $R^{6b}$, $R^7$, $R^8$, $R^{9a}$, $R^{9b}$, $R^{10}$, $R^{11}$, $R^{12}$, $R^{13a}$ and $R^{13b}$ are each independently as defined in the description.

6 Claims, 2 Drawing Sheets

9-AMINOMETHYL SUBSTITUTED TETRACYCLINE COMPOUNDS

PRIOR RELATED APPLICATIONS

This application is a National Phase application of International Application No. PCT/CN2012/001001 filed Jul. 26, 2012, which claims priority to Chinese Patent Application No. 201110222016.3 filed Jul. 26, 2011, each of which is incorporated herein by reference in its entirety.

TECHNICAL FIELD

The present invention relates to 9-aminomethyl substituted tetracycline compounds, or pharmaceutically acceptable salt, prodrug, solvate or isomer thereof, as well as a method for preparing these compounds and a pharmaceutical composition comprising the same. The present invention relates also to a use of these compounds in the preparation of a medicament for the treatment and/or prophylaxis of tetracycline drug-sensitive disease.

BACKGROUND ART

Tetracycline antibiotics are a kind of broad-spectrum antibiotics for oral use, which are generated by Actinomycete-*Streptomyces* fermentation. They have good pharmacological action against rickettsiales, many Gram-positive and Gram-negative bacteria, lymphogranuloma venereum pathogens, inclusion conjunctivitis pathogens and psittacosis pathogens.

The first tetracycline antibiotic is aureomycin extracted from *Streptomyces aureofaciens* in 1948, and then oxytetracycline, tetracycline and demeclocycline, which are all nature products have been developed successively. However, these drugs have high drug resistance and many side effects. Studies on the chemical structures of these compounds have been conducted later, and as a result, demethyl-tetracycline and dimethylamino-tetracycline have been synthesized. But the wide use of tetracyclines brings about more and more serious drug resistance of bacterium, which renders the use reduction of tetracycline antibiotics.

In the early 1990s, a new, third-generation tetracycline named as glycyclines were developed, and the representative drug was tigecylcine (GAR-936), which had broad antimicrobial spectrum. Tigecylcine has similar antibacterial activity with the prior tetracyclines, and further, due to efflux mechanism and ribosomal protection mechanisms, it has antibacterial activity even to the pathogens resistant against tetracyclines. However, tigecylcine can not be used orally, but only by intravenous drip for twice a day. Therefore, the use of tigecylcine is inconvenient and painful for patients. There is no oral-usable tigecylcine commercially available now.

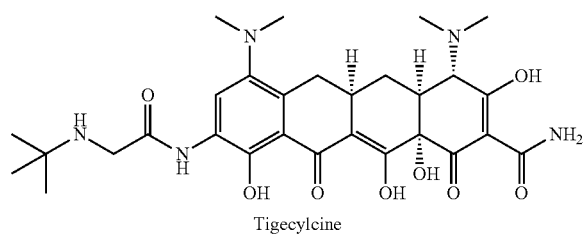 [SMILES: CN(C)c1cc(NC(=O)CNC(C)(C)C)c(O)c2c1C[C@H]1C[C@H]3[C@H](N(C)C)C(O)=C(C(N)=O)C(=O)[C@@]3(O)C(O)=C1C2=O]
Tigecylcine

The PCT application of WO2004/064728 has disclosed the compounds having structures as below, and studied the antibacterial activity thereof, but found they have poor antibacterial activity.

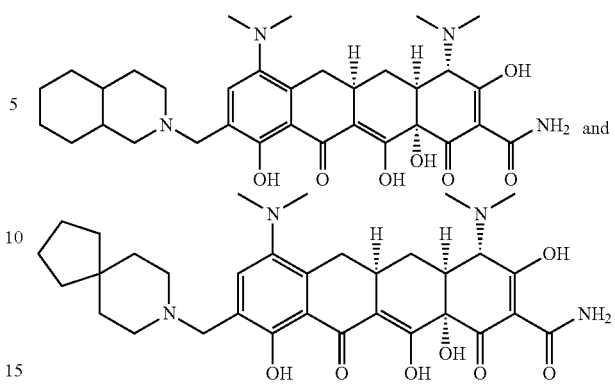

PTK-0796 is an oral-usable tetracycline antibiotic developed by Paratek Company, and it is being at phase III clinical trials for treating complex skin and skin soft-tissue infection. This drug may be administrated via injection or oral use once a day, and has broad antimicrobial spectrum. It has strong antibacterial activity to Grain-positive and Grain-negative bacteria, anaerobicbacteria, and atypical bacteria which are sensitive or resistance to many drugs. However, there are few tetracycline antibiotics similar with PTK-0796, and as such there are many limitations in the current clinic drug use.

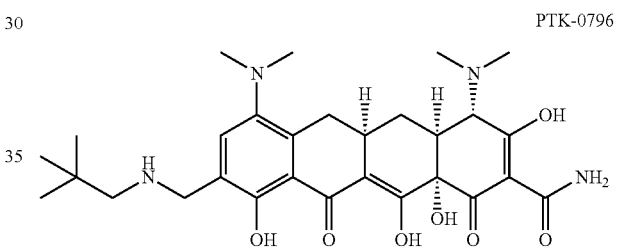
PTK-0796

Therefore, there is an insistent demand to develop new tetracycline antibiotics which have broad antimicrobial spectrum and strong antibacterial activity, and may be administrated for one time or orally, and may be easily synthesized and suitable for industrial production.

SUMMARY OF THE INVENTION

The present invention relates to a compound represented by the following general formula I:

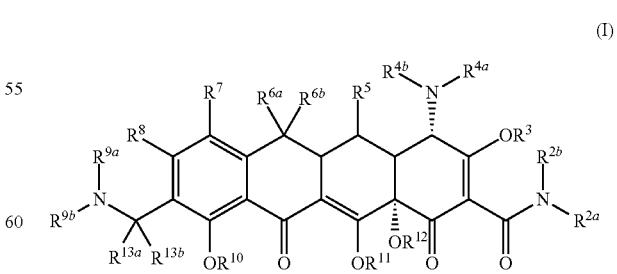

(I)

or pharmaceutically acceptable salt, prodrug, solvate or isomer thereof, wherein, $R^{2a}$, $R^{2b}$, $R^3$, $R^{10}$, $R^{11}$ and $R^{12}$ are each independently hydrogen;

$R^5$, $R^{6a}$, $R^{6b}$ and $R^8$ are each independently hydrogen, mercapto, halogen, hydroxy, amino, carboxyl, $C_{1-6}$alkyl, halo$C_{1-6}$alkyl, $C_{2-6}$alkenyl, $C_{2-6}$alkynyl, $C_{1-6}$alkoxy, halo$C_{1-6}$ alkoxy, $C_{1-6}$alkylthio, $C_{1-6}$alkylamino, di($C_{1-6}$alkyl) amino, hydroxy$C_{1-6}$alkyl, carboxyl$C_{1-6}$alkyl, amino$C_{1-6}$ alkyl, $C_{1-6}$alkylamino$C_{1-6}$alkyl, $C_{1-6}$alkylcarbonyl, $C_{1-6}$alkylcarbonyloxy, $C_{1-6}$alkoxycarbonyl, $C_{1-6}$alkylsulfinyl, $C_{1-6}$alkylsulfonyl, sulfonic, sulfonyl$C_{1-6}$alkyl, sulfoamino, sulfoamino$C_{1-6}$alkyl, $C_{1-6}$alkylsulfoamino, aminosulfonyl, $C_{1-6}$alkylaminosulfonyl, di($C_{1-6}$alkyl)amino sulfonyl, aminosulfonyl$C_{1-6}$alkyl, $C_{1-6}$alkylformylamino, $C_{1-6}$alkylcarbamoyl, di($C_{1-6}$alkyl)carbamoyl, carbamoyl, carbamoyl$C_{1-6}$alkyl, 3- to 8-membered cycloalkyl, 6- to 14-membered aryl, 6- to 14-membered aryl-$C_{1-6}$alkyl, 6- to 14-membered aryl-formyl, 6- to 14-membered aryl-formyloxy, 3- to 8-membered heterocyclyl, 3- to 8-membered heterocyclyl-$C_{1-6}$alkyl, 6- to 14-membered heteroaryl, or 6- to 14-membered heteroaryl-$C_{1-6}$alkyl;

$R^7$ is $NR^{7a}R^{7b}$;

$R^{4a}$, $R^{4b}$, $R^{7a}$ and $R^{7b}$ are each independently hydrogen, $C_{1-6}$alkyl, halo$C_{1-6}$alkyl, $C_{2-6}$alkenyl, $C_{2-6}$alkynyl, $C_{1-6}$alkoxy, halo$C_{1-6}$alkoxy, $C_{1-6}$alkylthio, hydroxy$C_{1-6}$ alkyl, carboxyl$C_{1-6}$alkyl, amino$C_{1-6}$alkyl, $C_{1-6}$alkylamino$C_{1-6}$alkyl, $C_{1-6}$alkylcarbonyl, $C_{1-6}$alkoxycarbonyl, $C_{1-6}$alkylsulfinyl, $C_{1-6}$alkylsulfonyl, sulfonic, sulfonyl$C_{1-6}$ alkyl, sulfoamino$C_{1-6}$alkyl, amino sulfonyl, $C_{1-6}$alkylaminosulfonyl, di($C_{1-6}$alkyl)aminosulfonyl, aminosulfonyl$C_{1-6}$ alkyl, $C_{1-6}$alkylcarbamoyl, di($C_{1-6}$alkyl)carbamoyl, carbamoyl, carbamoyl$C_{1-6}$alkyl, 3- to 8-membered cycloalkyl, 6- to 14-membered aryl, 6- to 14-membered aryl-$C_{1-6}$alkyl, 3- to 14-membered heterocyclyl or 3- to 14-membered heterocyclyl-$C_{1-6}$alkyl;

$R^{9a}$ and $R^{9b}$ are each independently:

(1) hydrogen, provided that $R^{9a}$ and $R^{9b}$ can not be hydrogen at the same time, (2) cyclopropyl, cyclobutyl, 6- to 12-membered spirocyclic group, 6-membered endocyclic group, 8- to 12-membered endocyclic group or 6- to 10-membered saturated fused ring group, the above groups are unsubstituted or substituted by 1 to 3 substituent(s) which may be the same or different and selected from $Q^1$, and carbon(s) in said group may be replaced by 1 to 3 atom(s) or group(s) which may be the same or different and selected from O, CO, S, SO, $SO_2$, N and $NR^c$, $R^c$ represents hydrogen or $C_{1-6}$alkyl;

(3) cyclobutyl$C_{1-6}$alkyl, cyclopentyl$C_{1-6}$alkyl, 6- to 12-membered spirocyclic group $C_{1-6}$alkyl, 6- to 9-membered endocyclic group $C_{1-6}$alkyl or 6- to 10-membered saturated fused ring group $C_{1-6}$alkyl, the above groups are unsubstituted or substituted by 1 to 3 substituent(s) which may be the same or different and selected from $Q^1$, and carbon(s) in said cyclobutyl, 6- to 12-membered spirocyclic group and 6- to 9-membered endocyclic group may be replaced by 1 to 3 atom(s) or group(s) which may be the same or different and selected from O, CO, S, SO, $SO_2$, N and $NR^c$, carbon(s) in said 6- to 10-membered saturated fused ring group may be replaced by 1 to 3 atom(s) or group(s) which may be the same or different and selected from CO, S, SO, $SO_2$, N and $NR^c$, $R^c$ represents hydrogen or $C_{1-6}$alkyl;

Alternatively, $R^{9a}$ and $R^{9b}$ together with the nitrogen atom to which they are attached form azetidinyl, 6- to 9-membered spirocyclic group or 6- to 9-membered saturated fused ring group, the above groups are unsubstituted or substituted by 1 to 3 $Q^2$ substituent(s) which may be the same or different, and carbon(s) in said azetidinyl, 6- to 9-membered spirocyclic group and 6- to 9-membered saturated fused ring group may be replaced by 1 to 3 atom(s) or group(s) which may be the same or different and selected from O, CO, S, SO, $SO_2$, N and $NR^c$, $R^c$ represents hydrogen or $C_{1-6}$alkyl;

$Q^1$ and $Q^2$ are independently selected from halogen, hydroxy, amino, carboxyl, $C_{1-6}$alkyl, $C_{1-6}$alkoxy, halo$C_{1-6}$ alkyl, halo$C_{1-6}$alkoxy, hydroxy$C_{1-6}$alkyl, amino$C_{1-6}$alkyl, carboxyl$C_{1-6}$alkyl, $C_{1-6}$alkylamino, di($C_{1-6}$alkyl)amino, aminosulfonyl, aminosulfonyl$C_{1-6}$alkyl, carbamoyl, carbamoyl$C_{1-6}$alkyl, $C_{1-6}$alkylcarbonyl, $C_{1-6}$alkylcarbonyloxy, $C_{1-6}$alkoxycarbonyl, phenyl, 3- to 8-membered cycloalkyl or 3- to 8-membered heterocyclyl;

$R^{13a}$ and $R^{13b}$ are each independently hydrogen, $C_{1-6}$alkyl or 3- to 8-membered cycloalkyl.

Preferably, Formula (I) has a structure represented by Formula (II) as below:

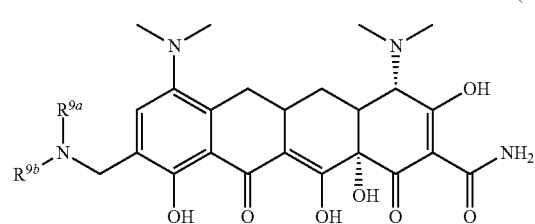

(II)

$R^{9a}$ and $R^{9b}$ are each independently as defined in above Formula (I).

Preferably, Formula (I) has a structure represented by Formula (III) as below:

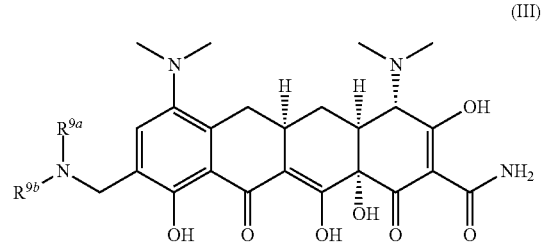

(III)

$R^{9a}$ and $R^{9b}$ are each independently as defined in above Formula (I).

More preferably, in the above formulas (I)~(III)

$R^{9a}$ and $R^{9b}$ are each independently:

(1) hydrogen, provided that $R^{9a}$ and $R^{9b}$ can not be hydrogen at the same time, (2) cyclopropyl, cyclobutyl, 6- to 12-membered spirocyclic group, 6-membered endocyclic group or 6- to 10-membered saturated fused ring group, the above groups are unsubstituted or substituted by 1 to 3 substituent(s) which may be the same or different and selected from $Q^1$, and carbon(s) in said cyclopropyl, cyclobutyl, 6- to 12-membered spirocyclic group, 6-membered endocyclic group and 6- to 10-membered saturated fused ring group may be replaced by 1 to 3 atom(s) or group(s) which may be the same or different and selected from O, CO, S, N and $NR^c$, $R^c$ represents hydrogen or $C_{1-4}$alkyl, (3) cyclobutyl$C_{1-4}$alkyl, cyclopentyl$C_{1-4}$alkyl, 6- to 12-membered spirocyclic group $C_{1-4}$alkyl, 6- to 9-membered endocyclic group $C_{1-4}$alkyl or 6- to 10-membered saturated fused ring group-$C_{1-4}$alkyl, the above groups are unsubstituted or substituted by 1 to 3 substituent(s) which may be the same or different and selected from $Q^1$, and carbon(s) in said cyclobutyl, 6- to 12-membered spirocyclic group and 6- to 9-membered endocyclic group may be replaced by 1 to 3 atom(s) or group(s) which may be the same or different and selected from O, CO, S, N and $NR^c$, carbon(s) in said 6- to 10-membered saturated fused ring group may be replaced by 1 to 3 atom(s) or group(s) which may be the same or different and selected from CO, S, N and $NR^c$, $R^c$ represents hydrogen or $C_{1-4}$alkyl;

Alternatively, $R^{9a}$ and $R^{9b}$ together with the nitrogen atom to which they are attached form azetidinyl, 6- to 9-membered spirocyclic group or 6- to 9-membered saturated fused ring group, the above groups are unsubstituted or substituted by 1 to 3 $Q^2$ substituent(s) which may be the same or different, and carbon(s) in said azetidinyl, 6- to 9-membered spirocyclic group and 6- to 9-membered saturated fused ring group may be replaced by 1 to 3 atom(s) or group(s) which may be the same or different and selected from O, CO, S, N and $NR^c$, $R^c$ represents hydrogen or $C_{1-4}$alkyl; and $Q^1$ and $Q^2$ are independently selected from halogen, hydroxy, amino, carboxyl, $C_{1-4}$alkyl, $C_{1-4}$alkoxy, halo$C_{1-4}$alkyl, halo$C_{1-4}$alkoxy, phenyl, 3-to 8-membered cycloalkyl or 3- to 8-membered heterocyclyl.

More preferably, in the above formulas (I)~(III), $R^{9a}$ and $R^{9b}$ are each independently
(1) hydrogen, provided that $R^{9a}$ and $R^{9b}$ can not be hydrogen at the same time,
(2) cyclopropyl, cyclobutyl, 6- to 10-membered spirocyclic group, 6-membered endocyclic group or 6- to 10-membered saturated fused ring group, the above groups are unsubstituted or substituted by 1 to 3 substituent(s) which may be the same or different and selected from $Q^1$, and carbon(s) in said cyclopropyl, cyclobutyl, 6- to 10-membered spirocyclic group, 6-membered endocyclic group and 6- to 10-membered saturated fused ring group may be replaced by 1 to 3 atom(s) or group(s) which may be the same or different and selected from O, CO, N and $NR^c$, $R^c$ represents hydrogen or $C_{1-4}$alkyl,
(3) cyclobutyl$C_{1-4}$alkyl, cyclopentyl$C_{1-4}$alkyl, 6- to 10-membered spirocyclic group $C_{1-4}$alkyl, 6- to 9-membered endocyclic group $C_{1-4}$alkyl or 6- to 10-membered saturated fused ring group-$C_{1-4}$alkyl, the above groups are unsubstituted or substituted by 1 to 3 substituent(s) which may be the same or different and selected from $Q^1$, and carbon(s) in said cyclobutyl, 6- to 10-membered spirocyclic group and 6- to 9-membered endocyclic group may be replaced by 1 to 3 atom(s) or group(s) which may be the same or different and selected from O, CO, N and $NR^c$, and carbon(s) in said 6- to 10-membered saturated fused ring group may be replaced by 1 to 3 atom(s) or group(s) which may be the same or different and selected from CO, N and $NR^c$, $R^c$ represents hydrogen or $C_{1-4}$alkyl;

Alternatively, $R^{9a}$ and $R^{9b}$ together with the nitrogen atom to which they are attached form azetidinyl, 6- to 9-membered spirocyclic group or 6- to 9-membered saturated fused ring group, the above groups are unsubstituted or substituted by 1 to 3 $Q^2$ substituent(s) which may be the same or different, and carbon(s) in said azetidinyl, 6- to 9-membered spirocyclic group and 6- to 9-membered saturated fused ring group may be replaced by 1 to 3 atom(s) or group(s) which may be the same or different and selected from O, CO, N and $NR^c$, $R^c$ represents hydrogen or $C_{1-4}$alkyl; and $Q^1$ and $Q^2$ are independently selected from halogen, hydroxy, amino, carboxyl, $C_{1-4}$alkyl, $C_{1-4}$alkoxy or halo$C_{1-4}$alkyl.

Further preferably, in the above formulas (I)~(III), $R^{9a}$ and $R^{9b}$ are each independently:
(1) hydrogen, provided that $R^{9a}$ and $R^{9b}$ can not be hydrogen at the same time,
(2) cyclopropyl, cyclobutyl, 6- to 10-membered spirocyclic group, 6-membered endocyclic group or 6- to 10-membered saturated fused ring group, the above groups are unsubstituted or substituted by 1 to 3 substituent(s) which may be the same or different and selected from $Q^1$, and carbon(s) in said cyclopropyl, cyclobutyl, 6- to 10-membered spirocyclic group, 6-membered endocyclic group and 6- to 10-membered saturated fused ring group may be replaced by 1 to 3 atom(s) or group(s) which may be the same or different and selected from O, N and $NR^c$, $R^c$ represents hydrogen or $C_{1-4}$alkyl;
(3) cyclobutyl$C_{1-3}$alkyl, cyclopentyl$C_{1-3}$alkyl, 6- to 10-membered spirocyclic group $C_{1-3}$alkyl, 6- to 9-membered endocyclic group $C_{1-3}$alkyl or 6- to 10-membered saturated fused ring group $C_{1-3}$alkyl, the above groups are unsubstituted or substituted by 1 to 3 substituent(s) which may be the same or different and selected from $Q^1$, and carbon(s) in said cyclobutyl, 6- to 10-membered spirocyclic group and 6- to 9-membered endocyclic group may be replaced by 1 to 3 atom(s) or group(s) which may be the same or different and selected from O, N and $NR^c$, carbon(s) in said 6- to 10-membered saturated fused ring group may be replaced by 1 to 3 atom(s) or group(s) which may be the same or different and selected from N and $NR^c$, $R^c$ represents hydrogen or $C_{1-4}$alkyl;

Alternatively, $R^{9a}$ and $R^{9b}$ together with the nitrogen atom to which they are attached form azetidinyl, 6- to 9-membered spirocyclic group or 6- to 9-membered saturated fused ring group, the above groups are unsubstituted or substituted by 1 to 3 $Q^2$ substituent(s) which may be the same or different, and carbon(s) in said azetidinyl, 6- to 9-membered spirocyclic group and 6- to 9-membered saturated fused ring group may be replaced by 1 to 3 atom(s) or group(s) which may be the same or different and selected from O, N and $NR^c$, $R^c$ represents hydrogen or $C_{1-4}$alkyl; and $Q^1$ and $Q^2$ are independently selected from halogen, $C_{1-4}$alkyl, halo$C_{1-4}$alkyl or amino.

Further more preferably, in the above formulas (I)~(III), $R^{9a}$ and $R^{9b}$ are each independently:
(1) hydrogen, provided that $R^{9a}$ and $R^{9b}$ can not be hydrogen at the same time,
(2) cyclopropyl, cyclobutyl, 6- to 8-membered spirocyclic group or 6-membered endocyclic group, the above groups are unsubstituted or substituted by 1 to 3 substituent(s) which may be the same or different and selected from $Q^1$, and carbon(s) in said cyclopropyl, cyclobutyl, 6- to 8-membered spirocyclic group and 6-membered endocyclic group may be replaced by 1 to 3 atom(s) or group(s) which may be the same or different and selected from N and $NR^c$, $R^c$ represents hydrogen, methyl or ethyl;
(3) cyclobutyl$C_{1-3}$alkyl, cyclopentyl$C_{1-3}$alkyl, 6- to 8-membered spirocyclic group $C_{1-3}$alkyl, 6- to 8-membered endocyclic group $C_{1-3}$alkyl, the above groups are unsubstituted or substituted by 1 to 3 substituent(s) which may be the same or different and selected from $Q^1$, and carbon(s) in said cyclobutyl, 6- to 8-membered spirocyclic group and 6- to 8-membered endocyclic group may be replaced by 1 to 3 atom(s) or group(s) which may be the same or different and selected from O, N and $NR^c$, $R^c$ represents hydrogen, methyl or ethyl;

Alternatively, $R^{9a}$ and $R^{9b}$ together with the nitrogen atom to which they are attached form azetidinyl, 6- to 8-membered spirocyclic group or 6- to 9-membered saturated fused ring group, the above groups are unsubstituted or substituted by 1 to 3 $Q^2$ substituent(s) which may be the same or different, and carbon(s) in said azetidinyl, 6- to 8-membered spirocyclic group and 6- to 9-membered saturated fused ring group may be replaced by 1 to 3 atom(s) or group(s) which may be the same or different and selected from O, N and $NR^c$, $R^c$ represents hydrogen, methyl or ethyl; and $Q^1$ and $Q^2$ are independently selected from halogen, $C_{1-4}$alkyl or amino.

Particularly preferably, in the above formulas (I)~(III), $R^{9a}$ and $R^{9b}$ are each independently:

(1) hydrogen, provided that $R^{9a}$ and $R^{9b}$ can not be hydrogen at the same time, (2)

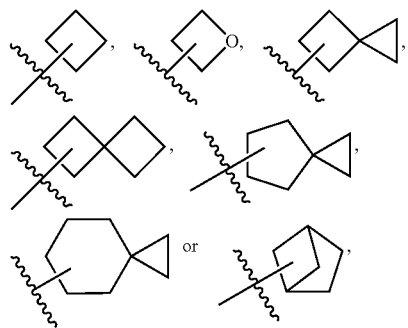

the above groups are unsubstituted or substituted by 1 to 3 substituent(s) which may be the same or different and selected from $Q^1$;

(3)

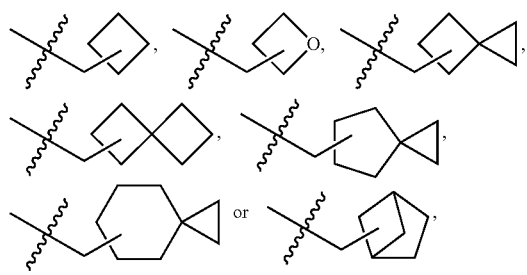

the above groups are unsubstituted or substituted by 1 to 3 substituent(s) which may be the same or different and selected from $Q^1$;

Alternatively, $R^{9a}$ and $R^{9b}$ together with the nitrogen atom to which they are attached form

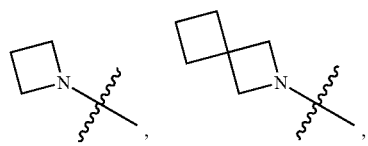

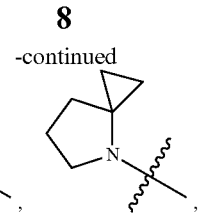

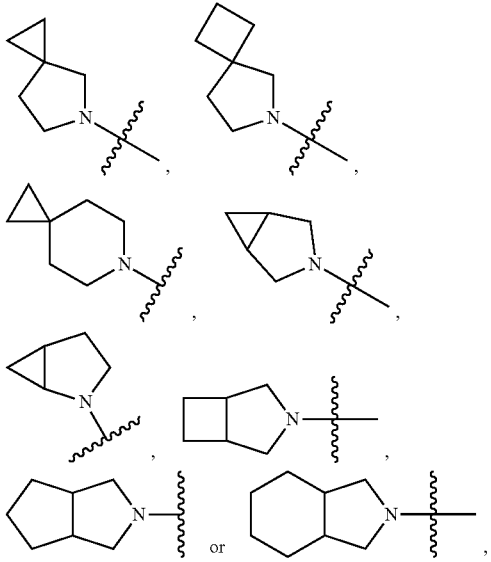

the above groups are unsubstituted or substituted by 1 to 3 $Q^2$ substituent(s) which may be the same or different;

$Q^1$ and $Q^2$ are independently selected from fluorine, chlorine, methyl or amino.

DETAILED DESCRIPTION OF THE INVENTION

Figure 1:
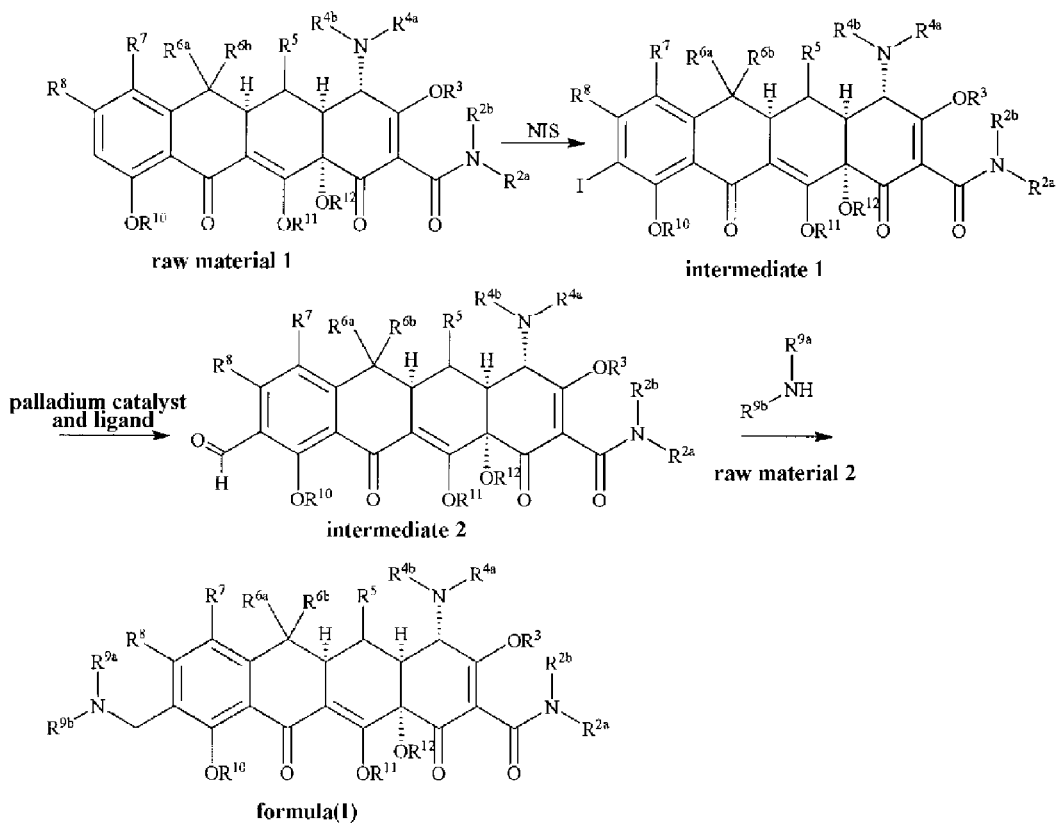
FIG. 1 is a synthetic scheme depicting a method for preparing the compounds of general formula (I).

The term "$C_{1-6}$ alkyl" as used herein means linear or branched alkyl having 1 to 6 carbon atoms and includes "$C_{1-4}$ alkyl", "$C_{1-3}$ alkyl", "$C_{1-2}$ alkyl" and the like. Examples include, but are not limited to, methyl, ethyl, n-propyl, isopropyl, n-butyl, 2-methylpropyl, 1-methylpropyl, 1,1-dimethylethyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like.

The term "$C_{2-6}$alkenyl" as used herein means linear or branched or cyclic alkenyl having 2 to 6 carbon atoms and containing double bonds. It includes "$C_{2-5}$ alkenyl", "$C_{2-4}$ alkenyl", "$C_{2-3}$alkenyl" and "$C_{3-6}$cycloalkenyl" etc., Examples include, but are not limited to, ethenyl 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-2-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1,3-butadienyl, 1,3-pentadienyl, 1,4-pentadienyl, 1,4-hexadienyl, cyclopropenyl, cyclobutenyl, cyclopentenyl, 1,3-cyclopentadienyl, cyclohexenyl, 1,4-cyclohexadienyl and the like.

The term "$C_{2-6}$alkynyl" as used herein means linear or branched alkynyl having 2 to 6 carbon atoms and containing triple bonds. It includes "$C_{2-5}$alkynyl", "$C_{2-4}$alkynyl" and "$C_{2-3}$alkynyl" etc. Examples include, but are not limited to, ethynyl, 2-propinyl, 2-butynyl, 3-butynyl, 1-methyl-2-propinyl, 2-pentynyl, 3-pentynyl, 4-pentynyl, 1-methyl-2-butynyl, 1-methyl-3-butynyl, 2-methyl-3-butynyl, 1,1-dimethyl-2-propinyl, 1-ethyl-2-propinyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl, 1-ethyl-1-methyl-2-propinyl and the like.

The terms "$C_{1-6}$alkoxy", "$C_{1-6}$alkylthio", "$C_{1-6}$alkylamino" "di($C_{1-6}$alkyl)amino", "$C_{1-6}$alkylcarbonyloxy", "$C_{1-6}$alkoxycarbonyl" "$C_{1-6}$alkylcarbonyl", "$C_{1-6}$alkylsulfonyl", "$C_{1-6}$alkylsulfinyl", "$C_{1-6}$alkylsulfoamino", "$C_{1-6}$alkylformylamino", "$C_{1-6}$alkylcarbamoyl" "di($C_{1-6}$alkyl)carbamoyl", "$C_{1-6}$alkylaminosulfonyl" "di($C_{1-6}$alkyl) aminosulfonyl" as used herein respectively refer to "$C_{1-6}$alkyl-O—", "$C_{1-6}$alkyl-S—", "$C_{1-6}$alkyl-NH—", "($C_{1-6}$alkyl)$_2$N—", "$C_{1-6}$alkyl-C(O)—O—", "$C_{1-6}$alkyl-O—C(O)—", "$C_{1-6}$alkyl-C(O)—", "$C_{1-6}$alkyl-SO$_2$—", "$C_{1-6}$alkyl-SO—", "$C_{1-6}$alkyl-SO$_2$—NH—", "$C_{1-6}$alkyl-C(O)—N H—", "$C_{1-6}$alkyl-NH—C(O)—", "($C_{1-6}$alkyl)$_2$N—C(O)—", "$C_{1-6}$alkyl-NH—SO$_2$—", "($C_{1-6}$alkyl)$_2$N—SO$_2$—", wherein "$C_{1-6}$alkyl" is defined as above.

The terms "$C_{1-4}$alkoxy", "$C_{1-4}$alkylthio", "$C_{1-4}$alkylamino", "di($C_{1-4}$alkyl)amino", "$C_{1-4}$alkylcarbonyloxy", "$C_{1-4}$alkoxycarbonyl", "$C_{1-4}$alkylcarbonyl", "$C_{1-4}$alkylsulfonyl", "$C_{1-4}$alkylsulfinyl", "$C_{1-4}$alkylsulfoamino", "$C_{1-4}$alkylformylamino", "$C_{1-4}$alkylcarbamoyl", "di($C_{1-4}$alkyl) carbamoyl", "$C_{1-4}$alkylaminosulfonyl", "di($C_{1-4}$alkyl)aminosulfonyl" as used herein respectively refer to "$C_{1-4}$ alkyl-O—", "$C_{1-4}$alkyl-S—", "$C_{1-4}$alkyl-NH—", "($C_{1-4}$ alkyl)$_2$N—", "$C_{1-4}$alkyl-C(O)—O—", "$C_{1-4}$alkyl-O—C(O)—", "$C_{1-4}$alkyl-C(O)—", "$C_{1-4}$alkyl-SO$_2$—", "$C_{1-4}$ alkyl-SO—", "$C_{1-4}$alkyl-SO$_2$—NH—", "$C_{1-4}$alkyl-C(O)—NH—", "$C_{1-4}$alkyl-NH—C(O)—", "($C_{1-4}$alkyl)$_2$N—C(O)—", "$C_{1-4}$alkyl-NH—SO$_2$—", "($C_{1-4}$alkyl)$_2$N—SO$_2$—", wherein "$C_{1-4}$ alkyl" is defined as above.

The term "hydroxy$C_{1-6}$alkyl", "carboxyl$C_{1-6}$alkyl", "amino$C_{1-6}$alkyl", "$C_{1-6}$alkylamino$C_{1-6}$alkyl", "sulfonyl$C_{1-6}$alkyl", "sulfoamino$C_{1-6}$alkyl", "aminosulfonyl$C_{1-6}$alkyl", "carbamoyl$C_{1-6}$alkyl" as used herein respectively refer to $C_{1-6}$alkyl substituted by hydroxy, carboxyl, amino, $C_{1-6}$alkylamino, sulfonyl, sulfoamino, aminosulfonyl, carbamoyl, wherein "$C_{1-6}$alkyl" is defined as above.

The terms "hydroxy$C_{1-4}$alkyl", "carboxyl$C_{1-4}$alkyl", "amino$C_{1-4}$alkyl", "$C_{1-4}$alkylamino$C_{1-4}$alkyl", "sulfonyl$C_{1-4}$ alkyl", "sulfoamino$C_{1-4}$alkyl", "aminosulfonyl$C_{1-4}$ alkyl", "carbamoyl$C_{1-4}$alkyl" as used herein respectively refer to $C_{1-4}$alkyl substituted by hydroxy, carboxyl, amino, $C_{1-4}$alkylamino, sulfonyl, sulfoamino, aminosulfonyl, carbamoyl, wherein "$C_{1-4}$alkyl" is defined as above.

The term "halogen" as used herein refers to fluorine, chlorine, bromine or iodine.

The term "halo$C_{1-6}$alkyl" as used herein refers to "$C_{1-6}$ alkyl" substituted by one or more "halogen" atom(s), the term "halo$C_{1-4}$alkyl" as used herein refers to "$C_{1-4}$alkyl" substituted by one or more "halogen" atom(s), wherein "halogen" and "$C_{1-6}$alkyl", "$C_{1-4}$alkyl" are defined as above.

The term "halo$C_{1-6}$alkoxy" as used herein refers to "$C_{1-6}$ alkoxy" substituted by one or more "halogen" atom(s), the term "halo$C_{1-4}$alkoxy" as used herein refers to "$C_{1-4}$alkoxy" substituted by one or more "halogen" atom(s), wherein "halogen", "$C_{1-6}$alkoxy", "$C_{1-4}$alkoxy" are defined as above.

The term "3- to 8-membered cycloalkyl" as used herein refers to a cyclic alkyl group, all the ring atoms of which are carbon atoms, and one hydrogen atom is removed from the ring, including for example 3- to 7-membered cycloalkyl group, 3- to 6-membered cycloalkyl, 4- to 6-membered cycloalkyl, 5- to 6-membered cycloalkyl; Examples include, but are not limited to, cyclopropyl, cyclobutyl, cyclopentyl, cyclohexyl, cycloheptyl, cyclooctyl, etc.

The term "6- to 12-membered spirocyclic group" as used herein refers to a structure containing 6-12 carbon atoms and/or hetero atoms and at least two rings share one atom, wherein the hetero atoms include nitrogen, oxygen and sulfur and the like. The group includes for example, 6- to 10-membered spirocyclic group, 6- to 9-membered spirocyclic group, 6- to 8-membered spirocyclic group, 7- to 8-membered spirocyclic group and the like. Examples include, but are not limited to,

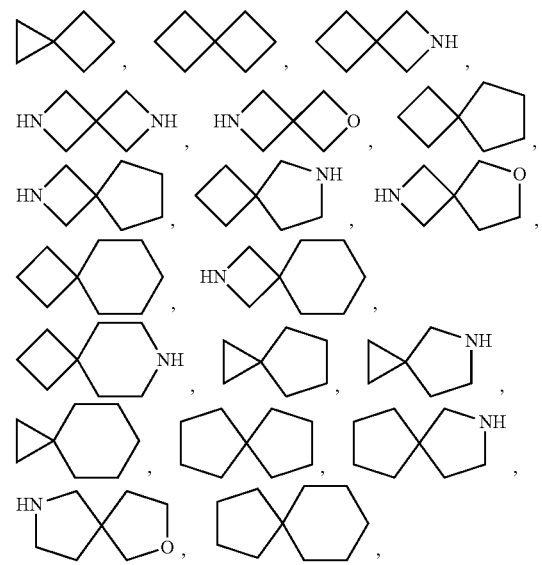

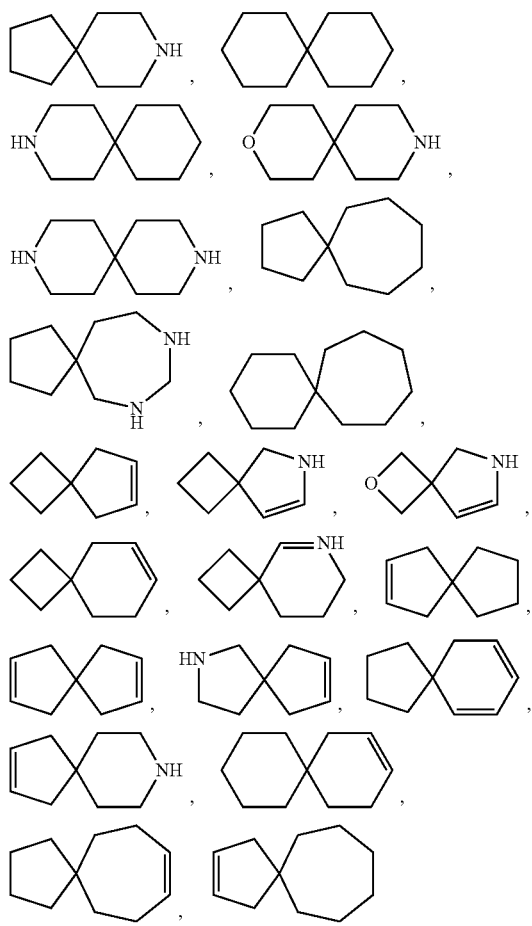

and the like.

The terms "6-membered endocyclic group" and "8- to 12-membered endocyclic group" as used herein refer to a structure containing 6 or 8-12 carbon atoms and/or hetero atoms and any two rings share two non-adjacent atoms, wherein the hetero atoms include nitrogen, oxygen and sulfur and the like. Examples include, but are not limited to,

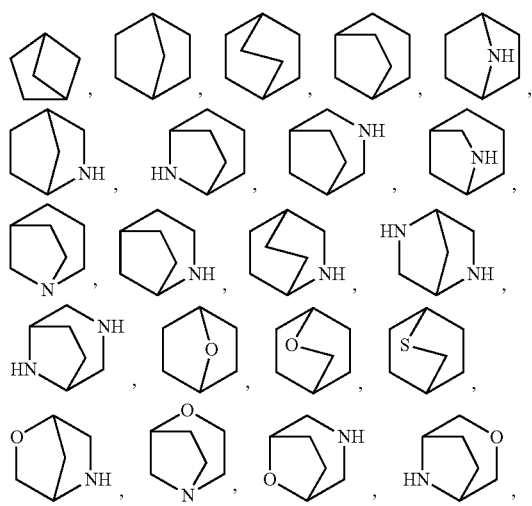

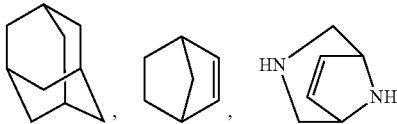

and the like.

The term "6- to 10-membered saturated fused ring group" as used herein refers to a saturated fused ring group containing 6-10 carbon atoms or/and a hetero atom, and formed by two or more cyclic structures sharing two adjacent atoms, wherein the hetero atoms include nitrogen, oxygen and sulfur and the like. The group includes 6- to 9-membered saturated fused ring group, 6- to 8-membered saturated fused ring group and the like. Examples include, but are not limited to e.g. bicyclo[3.1.0]hexyl, 3-azabicyclo[3.1.0]hexyl, 2-azabicyclo[3.1.0]hexyl, 3-azabicyclo[3.2.0]heptyl, 2-octahydrocyclopentane[C]pyrrolyl, bicyclo[3.2.0]heptyl, 3-azabicyclo[3.2.0]heptyl, octahydrocyclopentadienyl, octahydrocyclopenta[c]pyrrolyl, octahydropyrrolo[3,4-c]pyrrolyl, bicyclo[4.2.0]octyl, 3-azabicyclo[4.2.0]octyl, bicyclo[4.1.0]heptyl, octahydro-1H-indenyl, octahydro-1H-isoindolyl, decahydronaphthyl, decahydroisoquinolinyl and the like.

The term "6- to 14-membered aryl" as used herein refers to a cyclic aromatic group containing 6-14 carbon atoms, including 6- to 8-membered aryl, 8- to 14-membered aryl and the like. Examples include, but are not limited to, phenyl, naphthyl, phenanthryl, 2,3-dihydro-1H-indenyl, 1H-indenyl, 1,2,3,4-tetrahydronaphthyl, 1,4-dihydronaphthyl and the like.

The term "3- to 8-membered heterocyclyl" as used herein refers to monocyclic heterocyclic group having 3-8 ring atoms, and wherein at least one atom is hetero atom. The group includes 5- to 8-membered heterocyclyl, 5- to 6-membered heterocyclyl and the like. Examples include, but are not limited to, furyl, thienyl, pyrrolyl, thiazolyl, thiadiazolyl, oxazolyl, oxadiazolyl, imidazolyl, pyrazolyl, pyridyl, pyrimidinyl, 1,4-dioxinyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,2,4-triazinyl, 1,3,5-triazinyl, 1,2,4,5-tetrazinyl, oxepinyl, thiepinyl, azepinyl, 1,3-diazepinyl, azacyclooctatetraenyl, 2,5-dihydrothienyl, 4,5-dihydropyrazolyl, 3,4-dihydro-2H-pyranyl, 5,6-dihydro-4H-1,3-oxazinyl, aziridinyl, azetidinyl, thiacyclobutanyl, tetrahydrofuryl, tetrahydropyrrolyl, imidazolidinyl, pyrazolidinyl, tetrahydrofuranyl, 1,4-dioxanyl, 1,3-dioxanyl, 1,3-dithianyl, morpholinyl, piperazinyl and the like.

The term "6- to 14-membered heteroaryl" as used herein refers to a fused ring structure having 6-14 ring atoms, and wherein at least one atom is hetero atom, formed by two or more cyclic structures sharing two adjacent atoms. The group includes 8- to 12-membered heteroaryl, "9- to 10-membered heteroaryl and the like, for example, benzene ring fused with 3- to 8-membered heterocyclyl group, 3- to 8-membered heterocyclyl group fused with 3- to 8-membered heterocyclyl group. Examples include, but are not limited to, benzofuryl, benzisofuryl, benzothienyl, indolyl, benzoxazolyl, benzimidazolyl, indazolyl, benzotriazolyl, quinolyl, isoquinolyl, acridinyl, phenanthridinyl, benzopyridazinyl, phthalazinyl, quinazolinyl, quinoxalinyl, phenazinyl, pteridinyl, purinyl, naphthyridinyl, 1,3-dihydrobenzofuryl, benzo[d][1.3]dioxolyl, isoindolinyl, chromanyl, 1,2,3,4-tetrahydropyrrolo[3,4-c]pyrrolyl, 5,6-dihydroimidazo[1.2-a]pyrazin-7(8H)-yl, 5,6-dihydro-1,7-naphthyridin-7(8H)-yl, 5H-pyrrolo[3.4-b]pyridin-6(7H)-yl, 7,8-dihydropyridino[4.3-d]pyrimidin-6(5H)-yl, 2,3,6,7-tetrahydro-1H-pyrazolo[4,3-c]pyridin-5(4H)-yl, 6,7-dihydrothiazolo[5,4-c]pyridin-5 (4H)-yl, 3-methyl-6,7-dihydro-3H-pyrazolo[4.5-c]pyridin-5 (4H)-yl, 2-methyl-hexahydrocyclopenta[c]pyrrol-5-yl and the like.

Particularly preferred compounds of the present invention are shown in Table 1 below.

TABLE 1

| No. | Structure |
|-----|-----------|
| 1 | 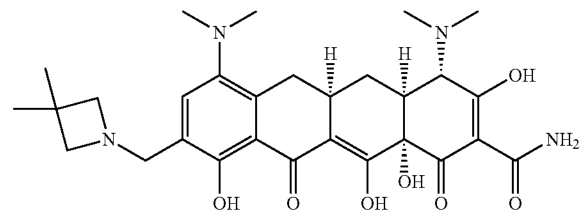 [SMILES: CN(C)c1cc(CN2CC(C)(C)C2)c(O)c2c1C[C@H]1C[C@H]3[C@H](N(C)C)C(O)=C(C(N)=O)C(=O)[C@@]3(O)C(O)=C1C2=O] |
| 2 | 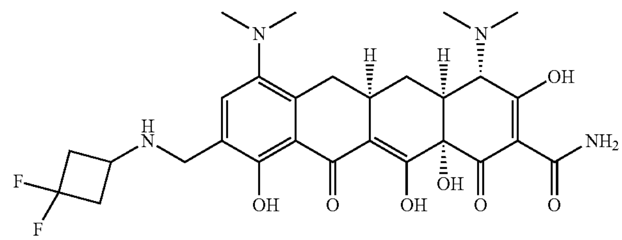 [SMILES: CN(C)c1cc(CNC2CC(F)(F)C2)c(O)c2c1C[C@H]1C[C@H]3[C@H](N(C)C)C(O)=C(C(N)=O)C(=O)[C@@]3(O)C(O)=C1C2=O] |
| 3 | 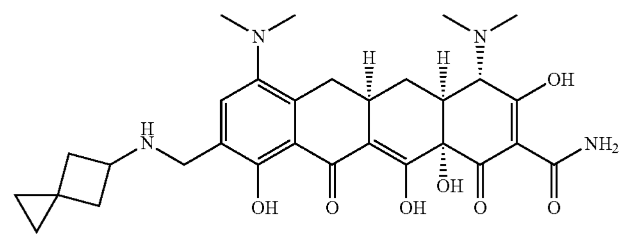 [SMILES: CN(C)c1cc(CNC2CC3(CC3)C2)c(O)c2c1C[C@H]1C[C@H]3[C@H](N(C)C)C(O)=C(C(N)=O)C(=O)[C@@]3(O)C(O)=C1C2=O] |
| 4 | 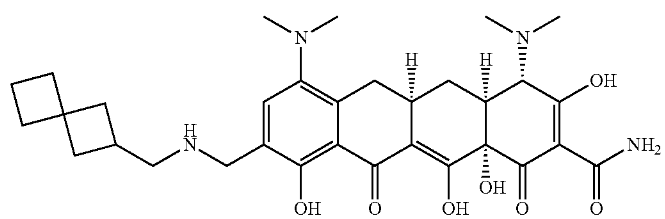 [SMILES: CN(C)c1cc(CNCC2CC3(CCC3)C2)c(O)c2c1C[C@H]1C[C@H]3[C@H](N(C)C)C(O)=C(C(N)=O)C(=O)[C@@]3(O)C(O)=C1C2=O] |
| 5 | 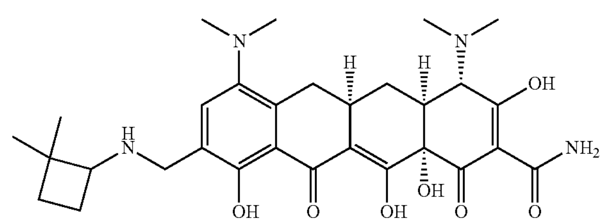 [SMILES: CN(C)c1cc(CNC2CCC2(C)C)c(O)c2c1C[C@H]1C[C@H]3[C@H](N(C)C)C(O)=C(C(N)=O)C(=O)[C@@]3(O)C(O)=C1C2=O] |
| 6 | 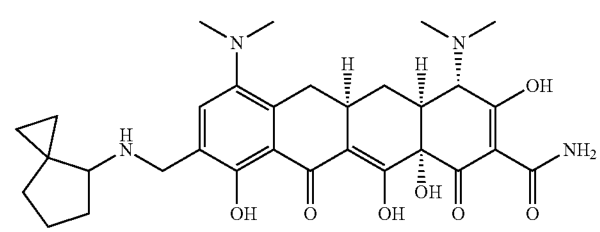 [SMILES: CN(C)c1cc(CNC2CCCC23CC3)c(O)c2c1C[C@H]1C[C@H]3[C@H](N(C)C)C(O)=C(C(N)=O)C(=O)[C@@]3(O)C(O)=C1C2=O] |

TABLE 1-continued

| No. | Structure |
|-----|-----------|
| 7 | 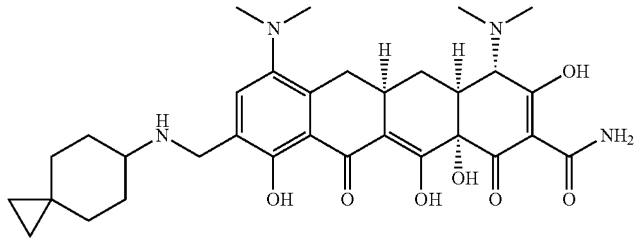 [SMILES: CN(C)c1cc(CNC2CCC3(CC2)CC3)c(O)c2c1C[C@H]1C[C@H]3[C@H](N(C)C)C(O)=C(C(N)=O)C(=O)[C@@]3(O)C(O)=C1C2=O] |
| 8 | 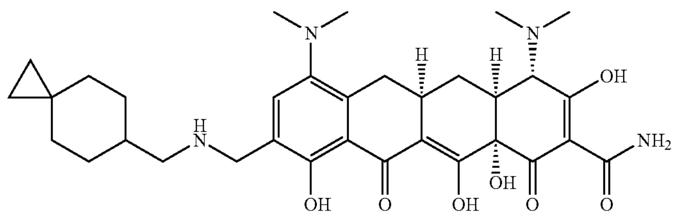 [SMILES: CN(C)c1cc(CNCC2CCC3(CC2)CC3)c(O)c2c1C[C@H]1C[C@H]3[C@H](N(C)C)C(O)=C(C(N)=O)C(=O)[C@@]3(O)C(O)=C1C2=O] |
| 9 | 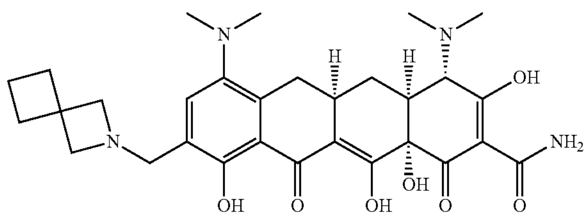 [SMILES: CN(C)c1cc(CN2CC3(CCC3)C2)c(O)c2c1C[C@H]1C[C@H]3[C@H](N(C)C)C(O)=C(C(N)=O)C(=O)[C@@]3(O)C(O)=C1C2=O] |
| 10 | 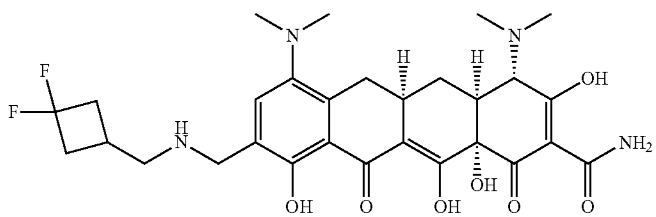 [SMILES: CN(C)c1cc(CNCC2CC(F)(F)C2)c(O)c2c1C[C@H]1C[C@H]3[C@H](N(C)C)C(O)=C(C(N)=O)C(=O)[C@@]3(O)C(O)=C1C2=O] |
| 11 | 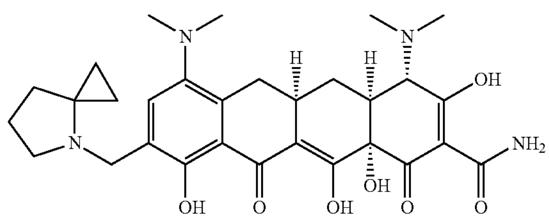 [SMILES: CN(C)c1cc(CN2CCCC23CC3)c(O)c2c1C[C@H]1C[C@H]3[C@H](N(C)C)C(O)=C(C(N)=O)C(=O)[C@@]3(O)C(O)=C1C2=O] |
| 12 | 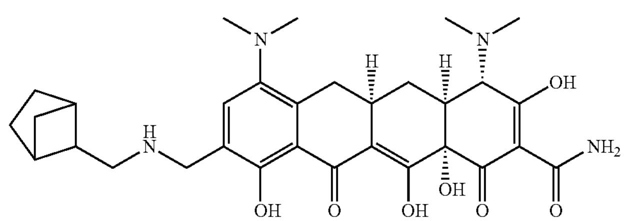 [SMILES: CN(C)c1cc(CNCC2C3CCC2C3)c(O)c2c1C[C@H]1C[C@H]3[C@H](N(C)C)C(O)=C(C(N)=O)C(=O)[C@@]3(O)C(O)=C1C2=O] |
| 13 | 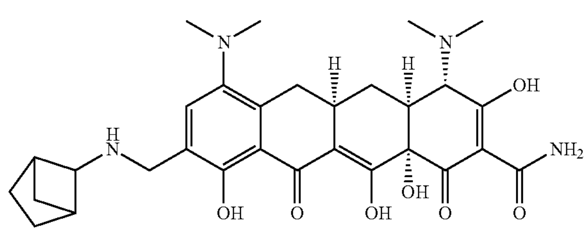 [SMILES: CN(C)c1cc(CNC2C3CCC2C3)c(O)c2c1C[C@H]1C[C@H]3[C@H](N(C)C)C(O)=C(C(N)=O)C(=O)[C@@]3(O)C(O)=C1C2=O] |

TABLE 1-continued

| No. | Structure |
|---|---|
| 14 | 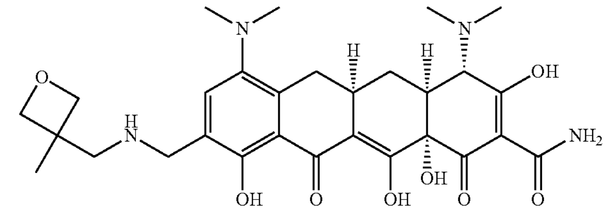 [SMILES: CN(C)c1cc(CNCC2(C)COC2)c(O)c2c1C[C@H]1C[C@H]3[C@H](N(C)C)C(O)=C(C(N)=O)C(=O)[C@@]3(O)C(O)=C1C2=O] |
| 15 | 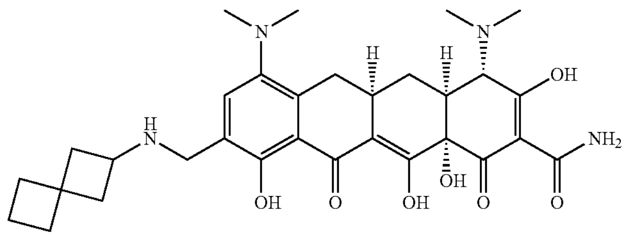 [SMILES: CN(C)c1cc(CNC2CC3(CCC3)C2)c(O)c2c1C[C@H]1C[C@H]3[C@H](N(C)C)C(O)=C(C(N)=O)C(=O)[C@@]3(O)C(O)=C1C2=O] |
| 16 | 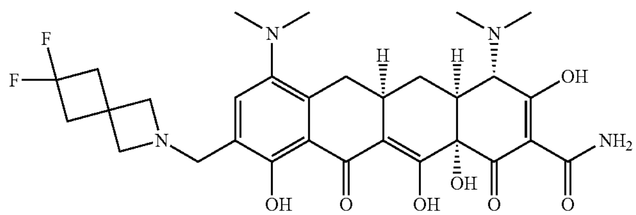 [SMILES: CN(C)c1cc(CN2CC3(C2)CC(F)(F)C3)c(O)c2c1C[C@H]1C[C@H]3[C@H](N(C)C)C(O)=C(C(N)=O)C(=O)[C@@]3(O)C(O)=C1C2=O] |
| 17 | 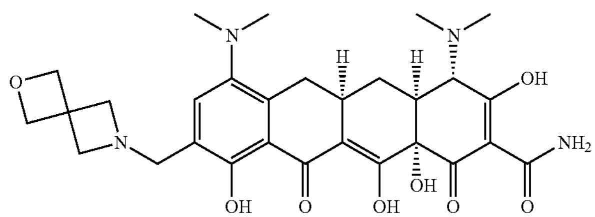 [SMILES: CN(C)c1cc(CN2CC3(COC3)C2)c(O)c2c1C[C@H]1C[C@H]3[C@H](N(C)C)C(O)=C(C(N)=O)C(=O)[C@@]3(O)C(O)=C1C2=O] |
| 18 | 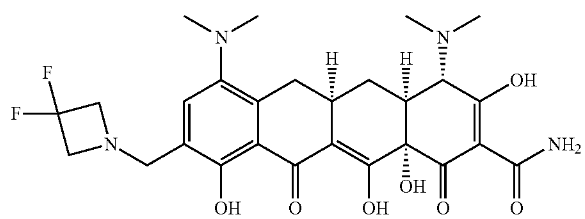 [SMILES: CN(C)c1cc(CN2CC(F)(F)C2)c(O)c2c1C[C@H]1C[C@H]3[C@H](N(C)C)C(O)=C(C(N)=O)C(=O)[C@@]3(O)C(O)=C1C2=O] |
| 19 | 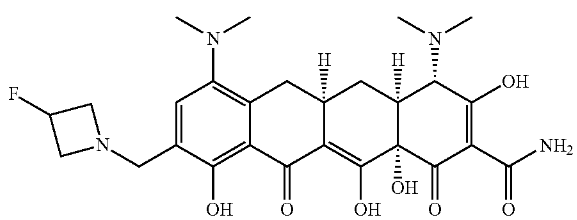 [SMILES: CN(C)c1cc(CN2CC(F)C2)c(O)c2c1C[C@H]1C[C@H]3[C@H](N(C)C)C(O)=C(C(N)=O)C(=O)[C@@]3(O)C(O)=C1C2=O] |
| 20 | 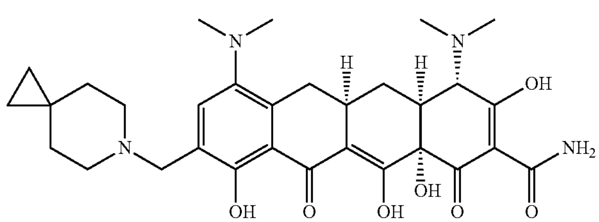 [SMILES: CN(C)c1cc(CN2CCC3(CC2)CC3)c(O)c2c1C[C@H]1C[C@H]3[C@H](N(C)C)C(O)=C(C(N)=O)C(=O)[C@@]3(O)C(O)=C1C2=O] |

TABLE 1-continued

| No. | Structure |
|---|---|
| 21 | 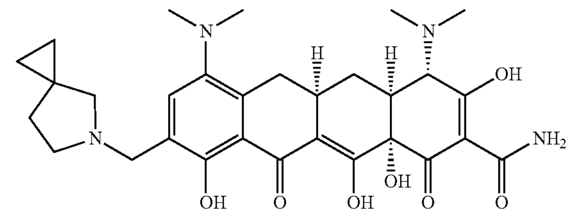 [SMILES: CN(C)c1cc(CN2CCC3(CC3)C2)c(O)c2c1C[C@H]1C[C@H]3[C@H](N(C)C)C(O)=C(C(N)=O)C(=O)[C@@]3(O)C(O)=C1C2=O] |
| 22 | 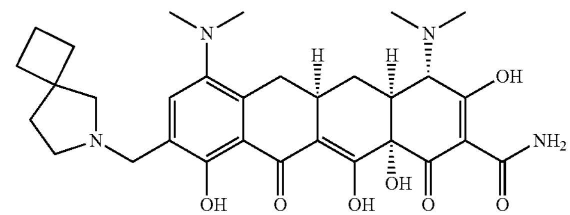 [SMILES: CN(C)c1cc(CN2CCC3(CCC3)C2)c(O)c2c1C[C@H]1C[C@H]3[C@H](N(C)C)C(O)=C(C(N)=O)C(=O)[C@@]3(O)C(O)=C1C2=O] |
| 23 | 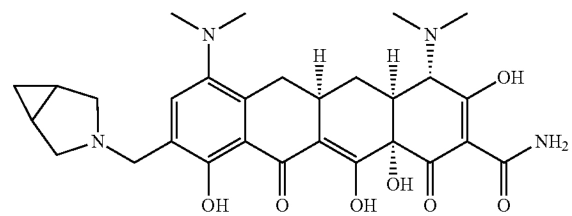 [SMILES: CN(C)c1cc(CN2CC3CC3C2)c(O)c2c1C[C@H]1C[C@H]3[C@H](N(C)C)C(O)=C(C(N)=O)C(=O)[C@@]3(O)C(O)=C1C2=O] |
| 24 | 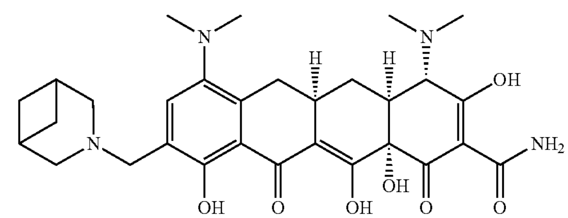 [SMILES: CN(C)c1cc(CN2CC3CC(C3)C2)c(O)c2c1C[C@H]1C[C@H]3[C@H](N(C)C)C(O)=C(C(N)=O)C(=O)[C@@]3(O)C(O)=C1C2=O] |
| 25 | 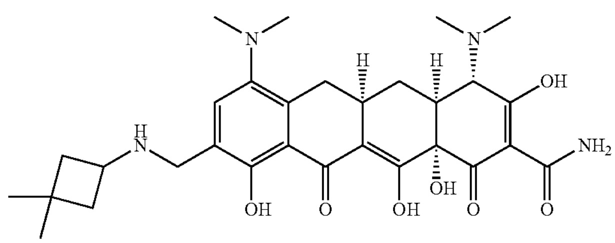 [SMILES: CN(C)c1cc(CNC2CC(C)(C)C2)c(O)c2c1C[C@H]1C[C@H]3[C@H](N(C)C)C(O)=C(C(N)=O)C(=O)[C@@]3(O)C(O)=C1C2=O] |
| 26 | 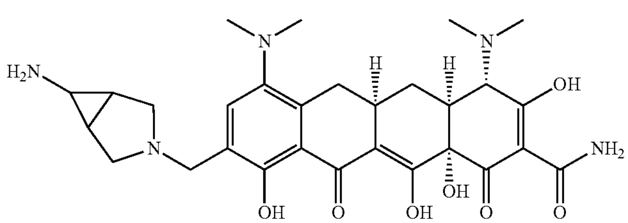 [SMILES: CN(C)c1cc(CN2CC3C(N)C3C2)c(O)c2c1C[C@H]1C[C@H]3[C@H](N(C)C)C(O)=C(C(N)=O)C(=O)[C@@]3(O)C(O)=C1C2=O] |
| 27 | 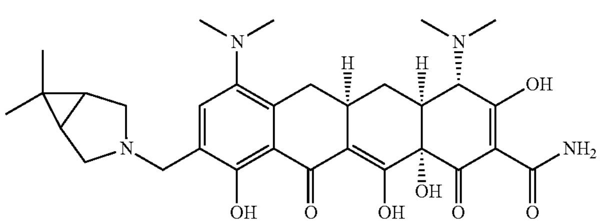 [SMILES: CN(C)c1cc(CN2CC3C(C2)C3(C)C)c(O)c2c1C[C@H]1C[C@H]3[C@H](N(C)C)C(O)=C(C(N)=O)C(=O)[C@@]3(O)C(O)=C1C2=O] |

TABLE 1-continued

| No. | Structure |
|---|---|
| 28 | 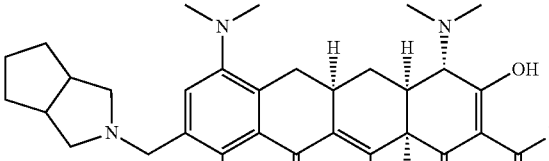 |
| 29 | 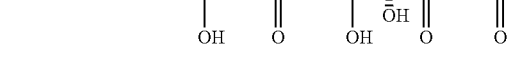 |

The present invention also relates to the preparation of the above compound of general formula (I), said method comprising the steps shown in FIG. 1.

The Reaction Steps:

(1) Preparation of Intermediate 1

Raw material 1 (commercially available) was added to the acidic catalyst, after the complete dissolvation, added N-iodosuccinimide (NIS). The reaction solution was poured into ice-water in which sodium thiosulfate was dissolved and stirred. The resulting mixture was extracted with an organic solvent, and the organic phase was rotary evaporated to remove solvents, and dried to give Intermediate 1.

(2) Preparation of Intermediate 2.

The intermediate 1, anhydrous sodium carbonate, a palladium catalyst and a metal complex ligand were placed in an anhydrous organic solvent and maintained a positive pressure of carbon monoxide atmosphere, further added triethylsilane or tri-n-butyl tin to generate hydrogen, or directly blown a mixed gas of carbon monoxide and hydrogen. After the completion of the reaction, the reaction was purified via a reversed-phase column to give Intermediate 2.

(3) Preparation of the Compound of Formula (I)

The intermediate 2 was dissolved in an organic solvent and the raw material 2 or a salt thereof was added, and further added an alkali. After the mixture was stirred at room temperature, the reducing agent was added and stirred, separated to give the compound of formula (I).

Said acidic catalyst is selected from the group consisting of, for example, but not limited to, methanesulfonic acid, p-toluenesulfonic acid, benzenesulfonic acid, etc.

Said palladium catalyst is selected from the group consisting of, for example, but not limited to, palladium acetate, palladium acetylacetonate (∥), bis(triphenylphosphino) palladium dichloride, tetrakis (triphenylphosphino) palladium.

Said metal complex ligand is selected from the group consisting of, for example, but not limited to, 4,5-bis(diphenylphosphino)-9,9-dimethylxanthene, bis(diphenylphosphino)methane, etc.

Said organic solvent is selected from the group consisting of, for example, but not limited to, acetonitrile, dimethylformamide, dimethyl sulfoxide, acetone, 1,3-dimethyl-2-imidazolinone, 1,3-dimethyl-3,4,5,6-tetrahydro-2-pyrimidone, toluene, ethyl acetate, chloroform, diethyl ether, N-methylpyrrolidone, etc.

Said bases include organic bases and inorganic bases, and inorganic bases are selected from the group consisting of, for example, but are not limited to, potassium hydroxide, sodium hydroxide, zinc hydroxide, calcium hydroxide, potassium carbonate, potassium bicarbonate, sodium carbonate, sodium bicarbonate and the like; said organic bases are selected from the group consisting of, for example, but not limited to, an amine compound such as methylamine, trimethylamine, diethylamine, triethylamine, diisopropylamine, ethylenediamine, triethanolamine, diisopropylethylamine, tributylamine, N,N-dimethylaniline, dicyclohexylamine, dibenzylamine, N-benzyl-β-phenylethyl amine, 1-diphenyl hydroxymethyl amine, N,N'-dibenzylethylene diamine, diethanolamine, dimethylethanolamine, 2-(diethylamino)ethanol, 2-aminoethanol, tromethamine; alkali metal salts of alcohols such as sodium methoxide, potassium ethoxide, potassium tert-butoxide, etc.; alkyl lithium compound such as ethyl lithium, n-butyl lithium, sec-butyl lithium, tert-butyl lithium, etc.; lithium amide compound such as lithium diisopropylamide, lithium hexamethyldisilyl amide.

Said reducing agent is selected from the group consisting of, for example, but are not limited to, lithium aluminum hydride, sodium cyanoborohydride, sodium triacetoxyboronhydride.

$R^{2a}$, $R^{2b}$, $R^3$, $R^{4a}$, $R^{4b}$, $R^5$, $R^{6a}$, $R^{6b}$, $R^7$, $R^8$, $R^{9a}$, $R^{9b}$, $R^{10}$, $R^{11}$ and $R^{12}$, in the above reaction equation are defined as above. When necessary, the needed functional groups can be protected, and the protecting group can be subsequently removed by a conventional method.

The term "pharmaceutically acceptable salt of the compound of formula (I)" refers to a salt prepared from a suitable inorganic or organic cation (base) when the compound of formula (I) includes an acidic group (eg. —COOH, —OH, $SO_3H$), including a salt formed with alkali metal such as sodium, potassium and lithium, a salt formed with alkaline earth such as calcium and magnesium, a salt formed with other metals such as aluminum, iron, zinc and copper, a salt formed with inorganic bases such as ammonium, a salt formed with organic bases such as tertiary-octyl amine, dibenzylamine, morpholine, glucamine, phenyl glycine alkyl ester, ethylenediamine, N-methylglucamine, guanidine, diethylamine, triethylamine, dicyclohexylamine, N,N'-dibenzyl-ethylenediamine, chloroprocaine, procaine, diethanol amine, N-benzyl-phenylethylamine, piperazine, tetramethylamine, tri(hydroxymethyl)aminomethane and the like.

Alternatively, the term "pharmaceutically acceptable salt of the compound of formula (I)" refers to a salt prepared from a suitable inorganic or organic anion (acid) when the compound of formula (I) includes a basic functional group (eg. —NH$_2$), including a salt formed with inorganic acids such as nitric acid, perchloric acid, sulfuric acid, phosphoric acid, hydrofluoric acid, hydrochloric acid, hydrobromic acid, hydroiodic acid, a salt formed with sulfonic acid such as methanesulfonic acid, trifluoromethanesulfonic acid, ethanesulfonic acid, benzenesulfonic acid, p-toluenesulfonic acid and the like; a salt formed with organic acids such as acetic acid, malic acid, fumaric acid, succinic acid, citric acid, tartaric acid, oxalic acid, maleic acid and the like; a salt formed with amino acids such as glycine, trimethyl glycine, arginine, ornithine, glutamic acid, aspartic acid and the like.

The term "solvate" of the present compound of formula (I) refers to the substance formed by associating with a solvent. The solvent may be an organic solvent (e.g., ethanol, methanol, propanol, acetonitrile, etc.), water, etc. For example, the compound of the present invention can form an ethanolate with ethanol, and a hydrate with water.

When one or more asymmetric carbon atoms exist in the compound of formula (I) of the present invention, there are diastereomers. When the compound contains an alkenyl group or a cyclic structure, there are cis/trans isomers. When the compound contains a ketone or an oxime, there are tautomers. All these enantiomorphs, diastereomers, racemic isomers, cis-trans isomers, tautomers, geometric isomers, epimeride and mixture thereof are included within the scope of the present invention.

The term "prodrug" of the present compound of formula (I) refers to the compounds that can be converted in vivo to the active form of the compound of the present invention (see R. B. Silverman, 1992, "The Organic Chemistry of Drug Design and Drug Action", Academic Press, Chp. 8). The prodrug can be used to change the biodistribution or pharmacokinetics. For example, a hydroxyl group or a carboxyl group is esterified to form an ester, and when the ester is administered to a patient, the ester is enzymaticly or non-enzymaticly hydrolyzed, and the ester group is removed via reduction or hydrolysis.

The compound of formula (I) of the present invention, the pharmaceutically acceptable salt, prodrug, solvate, or isomer thereof can be made into pharmaceutical preparations with one or more pharmaceutically acceptable carrier(s). Said pharmaceutical preparations refer to conventional preparations in the clinical use, and can be orally or parenterally applied to patients in need of such treatment. For oral administration, they can be made into conventional solid preparations such as tablets, capsulas, pills, granules, etc., as well as oral liquid preparations, such as oral solutions, oral suspensions, syrups, etc. For parenteral administration, they can be made into injections, including injection solution, a sterile powder for injection, concentrated solution for injection and suspension for injection. For rectal administration, they can be made into suppositories and the like. For transpulmonary administration, they can be made into inhalations or aerosols and the like. For topical or percutaneous administration, they can be made into ointments, pastes, creams, lotions, gels, powders, solutions or transdermal stickers and the like. These preparations can be prepared by a conventional method, adding pharmaceutically acceptable carriers such as excipients, binders, moisturizers, disintegrating agents, thickeners and the like.

The compounds of formula (I) or pharmaceutically acceptable salt, prodrug, solvate or isomer thereof can be used for the treatment and/or prophylaxis of tetracycline drug-sensitive disease including infections (e.g. infections of rickettsiales pathogens, lymphogranuloma venereum, inclusion conjunctivitis, psittacosis pathogens and other tetracycline compound resistant infections), cancers, diabetes and any other diseases which have been found to be treatable and/or preventable by tetracycline compounds. The mentioned tetracycline compounds refer to the compounds having tetracycline ring structure. Examples include aureomycin, terramycin, demeclocycline, methacycline, sancycline, rolitetracycline, guamecycline, minocycline, doxycycline, chelocardin and the like.

The administration amount and frequency of the compound of the present invention can be adjusted according to the judgment of the clinician or pharmacist, for example according to the patient's age, weight, the severity of the symptoms. Generally, the daily dose of the compound of the present invention when administrated in a single dose or divided doses may be for example 0.2 to 3 mg/kg body weight, preferably 0.5-2.5 mg/kg body weight. In one embodiment, for example, a patient is daily administered with approximately 10 mg-200 mg, preferably 30 mg-180 mg of the compound of the present invention in a single dose or multiple doses. In another embodiment, a patient is firstly administered with for example, 50 mg-150 mg, preferably 80 mg-120 mg of the compound of the present invention, then with 20 mg-100 mg/time, preferably 50 mg-80 mg/time in divided doses (e.g., one to four times a day).

The compound of the present invention is a broad spectrum antibacterial and has strong antibacterial activity against both Gram-positive and -negative bacteria, including aerobic and anaerobic bacteria, and further has good pharmacokinetics and high oral bioavailability. In addition, the administration of the compound of the present invention is convenience and able to meet clinical needs. Further, the synthesis of the compound of the present invention is simple, which is advantageous for industrial production.

EXAMPLES

Hereinafter, the present invention will be further illustrated in details by the following specific examples. However, these examples are illustrative only and should not be construed as limiting the invention in any way, and any functionally equivalent embodiments are within the scope of this invention.

In the examples, the abbreviations have the following meanings:

DAST: diethylaminosulfur trifluoride;
DCC: N,N'-dicyclohexylcarbodiimide;
DCM: dichloromethane;
DMF: N,N-dimethylformamide;
DMA: dimethyl adipate;
Et$_3$N: triethylamine;
EtOAc: ethyl acetate;
TEA: triethanolamine;
TFA: trifluoroacetic acid;
THF: tetrahydrofuran;
NMP: N-methylpyrrolidone;
NIS: N-iodosuccinimide;
NaBH$_3$CN: sodium cyanoborohydride;
NaBH$_4$: sodium borohydride;
InCl$_3$: indium trichloride;
NH$_4$Cl: ammonium chloride;
MeOH: methanol;
CCl$_3$COCl: trichloroacetyl chloride;
Me$_2$S: dimethyl sulfide;

NH$_3$.H$_2$O: ammonia;

STAB: sodium triacetoxyborohydride;

Boc-: tert-butoxycarbonyl;

Cbz-: benzyloxycarbonyl;

Ph-: phenyl;

Ms-: mesyl.

Minocycline hydrochloride used in the following examples was purchased from Suzhou Juli Chemical Co. Ltd and Hubei Prosperity Galaxy Chemical Co. Ltd.

Example 1

Preparation of (4S,4aS,5aR,12a5)-9-formyl-4,7-bis (dimethylamino)-3,10,12,12a-tetrahydroxy-1,1'-dioxo-1,4,4a,5,5a,6,11,12a-octahydrotetracene-2-carboxamide (Compound A)

1): (4S,4aS,5aR,12aS)-9-iodo-4,7-bis(dimethylamino)-3,10,12,12a-tetrahydroxy-1,1'-dioxo-1,4,4a, 5,5a,6,11,12a-octahydrotetracene-2-carboxamide (Compound B)

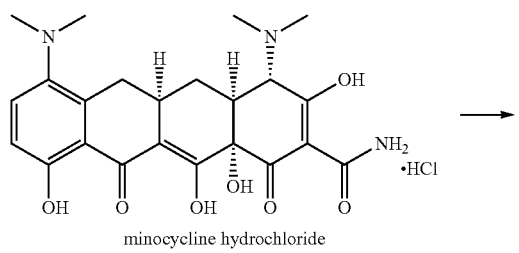

minocycline hydrochloride

To methanesulfonic acid (200 mL) was added minocycline hydrochloride (28 g) slowly portionwise. After complete dissolution of the compound, NIS (38 g, 168.9 mmol) was added portionwise at room temperature within 3 hours. Then the reaction mixture was poured into 20 mL of ice-water in which 17.9 g of sodium thiosulfate had been dissolved, and followed by vigorous stirring for 30 minutes. The obtained mixture was washed with ethyl acetate, and the aqueous phase was poured into a mixture of sodium bicarbonate (260 g) and n-butanol (300 mL), stirred, kept stand and separated. The aqueous phase was extracted with n-butanol again. The organic phases were combined and washed with water and a saturated aqueous solution of sodium chloride once respectively, and then rotary evaporated to remove solvents, dried in vacuo to give 22.8 g of Compound B as a yellow solid.

2) Compound A

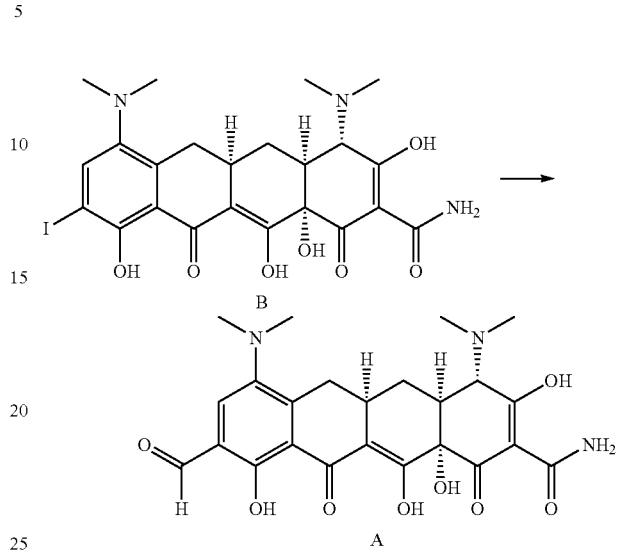

The above obtained Compound B (14.6 g), anhydrous sodium carbonate (10.6 g, 100 mmol), palladium acetate (0.11 g, 0.5 mmol) and 4,5-bis(diphenylphosphino)-9,9-dimethylxanthene (0.29 g, 0.5 mmol) were placed in anhydrous NMP (100 mL), and maintained a positive pressure of carbon monoxide atmosphere. The reaction mixture was heated to 70° C., and triethylsilane (4.44 mL, 27.5 mmol) was added dropwise within 90 minutes using a syringe. After the completion of addition, the mixture was purified by medium-pressure reverse-phase preparative column (water/acetonitrile) to give 4.8 g of compound A as a yellow solid.

LC-MS (M+H): 486 (Found)

Example 2

Preparation of (4S,4aS,5aR,12aS)-9-((3,3-dimethylazetidin-1-yl)methyl)-4,7-bis(dimethylamino)-3,10, 12,12a-tetrahydroxy-1,1'-dioxo-1,4,4a,5,5a,6,11,12a-octahydrotetracene-2-carboxamide (Compound 1)

1) Diethyl 2,2-dimethylmalonate (Compound 1-2)

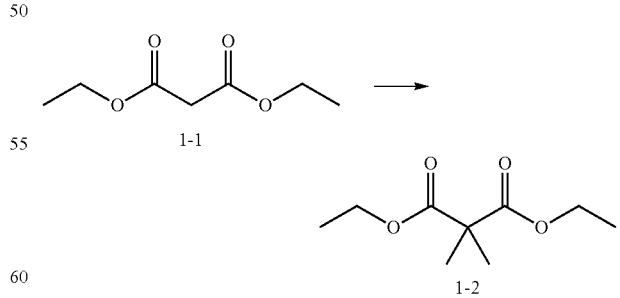

Sodium (36 g, 1.56 mol) was dissolved in 800 mL of anhydrous ethanol and was cooled with an ice-water bath, diethyl malonate (Compound 1-1) (100 g, 0.62 mol) was slowly added dropwise. After the completion of addition, methyl iodide (97.3 mL, 1.56 mol) was further added dropwise. The ice-water bath was removed after the completion of addition, the mixture was stirred at room temperature overnight. 1000 mL of water was added to the reaction mixture, and then extracted three times with 1000 mL of ethyl acetate, the organic phases were combined, washed with a saturated aqueous solution of sodium chloride, dried over anhydrous sodium sulfate, the desiccant was removed by filtration, and concentrated to give the crude Compound 1-2 as a pale yellow oil (102.1 g, 87.5% yield) and used directly in the next reaction.

2) 2,2-dimethylpropane-1,3-diol (Compound 1-3)

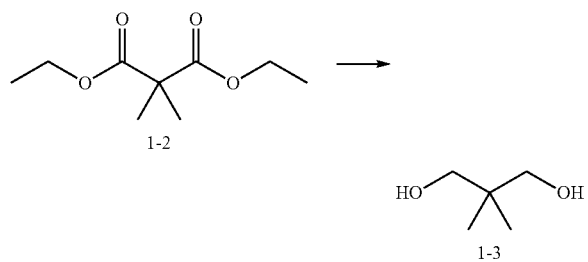

The above obtained Compound 1-2 (101.8 g, 0.54 mol) was dissolved in 750 mL of dry tetrahydrofuran, cooled with an ice-water bath, lithium aluminium hydride (30.8 g, 0.81 mol) was added portionwise to the above solution. After the addition was completed, the ice-water bath was removed, and the mixture was stirred at room temperature overnight. Added 100 mL of ethyl acetate and stirred for 2 hours to quench the reaction, then adjusted the pH to acidic using hydrochloric acid, and the solvent was removed by rotary evaporation. The resulting oil was purified by a short silica gel column (dichloromethane/methanol=10:1), and then concentrated to give the crude Compound 1-3 as a pale yellow oil, 36 g, yield 64%.

3) 2,2-dimethylpropane-1,3-diyl dimethanesulfonate (Compound 1-4)

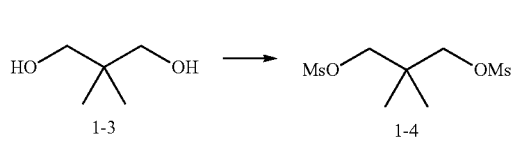

The above obtained Compound 1-3 (56.3 g, 0.54 mol) and triethylamine (302 mL, 2.17 mol) were dissolved in 600 mL of methylene chloride, cooled with an ice-water bath, mesyl chloride (168.7 mL, 2.17 mol) was added dropwise to the above mixture, and stirred at room temperature overnight. Added 1000 mL of water, stirred and separated. The aqueous phase was extracted with 300 mL of dichloromethane twice, and the organic phases were combined, washed successively with water and a saturated aqueous solution of sodium chloride, dried over anhydrous sodium sulfate, the desiccant was removed by filtration, the solvent was removed by rotary evaporation, and the residue was recrystallized with acetic acid acetate/cyclohexane (volume ratio 10:1) to give Compound 1-4 (76.6 g, 54.5% yield) as a brown solid.

4) 1,3-diiodo-2,2-dimethylpropane (Compound 1-5)

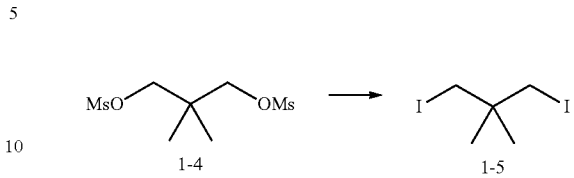

Compound 1-4 (50.4 g, 0.19 mol) and potassium iodide (193 g, 1.16 mol) were dissolved in 250 mL of DMF, heated to 110° C. and stirred overnight. Added 2000 mL of water, extracted three times with 1000 mL of ethyl acetate. The organic phases were combined, washed successively with water and brine, dried over anhydrous sodium sulfate, the desiccant was removed by filtration, and concentrated to give the crude Compound 1-5 as a black oil (62.6 g, crude).

5) 3,3-dimethyl-1-tosylazetidine (Compound 1-6)

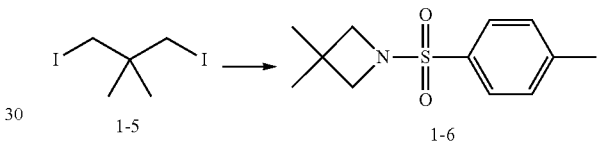

The above obtained Compound 1-5 (64.8 g, 0.2 mol), anhydrous potassium carbonate (82.2 g, 0.6 mol) and p-toluenesulfonamide (34.2 g, 0.2 mol) were dissolved in 200 mL of DMF, and reacted at 110° C. for 3 hours. Added 2000 mL of water and extracted three times with 1000 mL of petroleum ether. The organic phases were combined, washed successively with water and brine, dried over anhydrous sodium sulfate and filtered to remove the desiccant, and concentrated to give Compound 1-6 (21.9 g, 46% yield) as a white solid.

6) 3,3-dimethylazetidine hydrochloride (Compound 1-7)

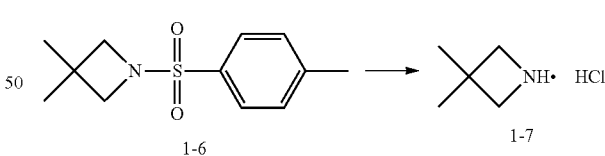

Compound 1-6 (7.2 g, 30 mmol) was dissolved in 100 mL of n-amyl alcohol, the reaction solution was controlled at 110° C., and was added portionwise 6.9 g of sodium metal. After the sodium disappeared, continued maintaining the temperature for 1 hour, and then cooled.

Thereto was poured 100 mL of water, separated the water phase, the organic phase was washed with 450 mL of 2N hydrochloric acid three times. The solvent was removed by rotary evaporation and the resulting residue was dissolved in 100 mL of a 2N aqueous solution of NaOH, then extracted three times with 300 mL of dichloromethane, the organic phases were combined and washed twice with a saturated aqueous solution of sodium chloride, dried over anhydrous sodium sulfate. Added 100 mL of 2N hydrochloric acid and concentrated to remove solvents to give Compound 1-7 (0.9 g, 24.7% yield) as a white solid.

7) Compound 1

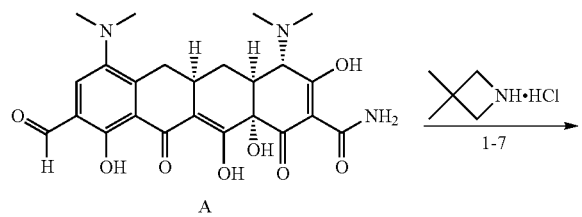

A

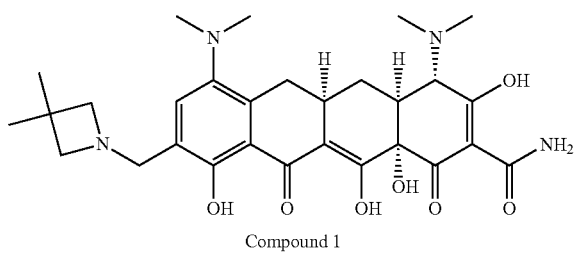

Compound 1

Compound A (0.5 g, 1.0 mmol) was dissolved in DMF (10 mL), added Compound 1-7 (0.3 g, 2.5 mmol), triethylamine (500 mg, 5 mmol) and anhydrous indium chloride (10 mg), and the mixture was stirred at room temperature for 30 minutes, then added sodium cyanoborohydride (0.3 g, 5.8 mmol), stirred for 0.5 h at room temperature and then separated by HPLC to give Compound 1 (35 mg).

$^1$H NMR (D$_2$O, 400 MHz) δ: 7.42 (s, 1H), 4.29 (s, 2H), 3.78-3.89 (m, 4H), 3.74 (s, 1H), 3.03 (m, 1H), 2.82 (s, 7H), 2.62 (m, 1H), 2.48-2.56 (m, 6H), 2.26 (m, 1H), 2.13 (m, 1H), 1.53-1.68 (m, 1H), 1.11-1.28 (m, 6H)

Example 3

Preparation of (4S,4aS,5aR,12aS)-9-((3,3-difluorocyclobutylamino)methyl)-4,7-bis(dimethylamino)-3,10,12,12a-tetrahydroxy-1,1'-dioxo-1,4,4a,5,5a,6,11,12a-octahydrotetracene-2-carboxamide (Compound 2)

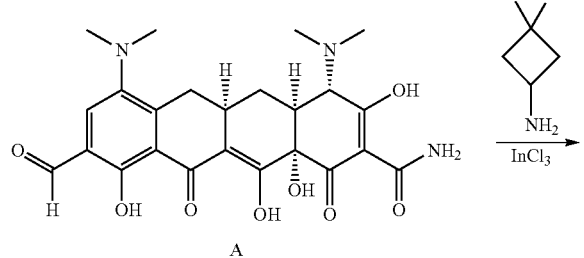

A

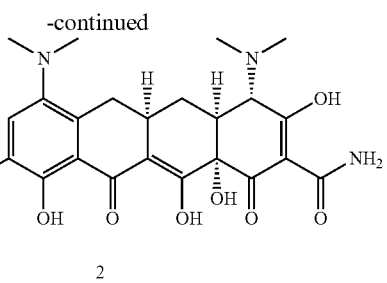

2

Compound A (0.8 g, 1.65 mmol), 3,3-difluorocyclobutylamine (0.5 g, 3.30 mmol), Et$_3$N (0.3 g, 3.30 mmol) and InCl$_3$ (73 mg, 0.33 mmol) were dissolved in 10 mL of DMF. The mixture was stirred at room temperature for 2 h and then added NaBH$_3$CN (209 mg, 3.30 mmol). The mixture was stirred at room temperature overnight, concentrated and isolated, then purified by preparative chromatography to obtain the objective Compound 2 as a yellow solid (0.508 g).

LC-MS (M+H): 577.2 (Found)

$^1$H-NMR (CD$_3$OD, 400 MHz) δ: 7.65 (s, 1H), 4.24 (s, 2H), 4.09 (s, 1H), 3.84 (m, 1H), 3.40 (m, 1H), 2.83-3.22 (m, 12H), 2.62-2.82 (m, 6H), 2.15-2.40 (m, 2H), 1.67 (m, 1H)

Example 4

Preparation of (4S,4aS,5aR,12aS)-9-((spiro[2.3]hexan-5-ylamino)methyl)-4,7-bis(dimethylamino)-3,10,12,12a-tetrahydroxy-1,1'-dioxo-1,4,4a,5,5a,6,11,12a-octahydrotetracene-2-carboxamide (Compound 3)

1) tert-Butyl 3-methylenecyclobutylcarbamate (Compound 3-2)

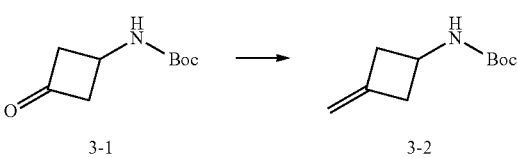

Triphenylphosphonium bromide (11 g, 30.8 mmol) was suspended in 250 mL of tetrahydrofuran and cooled in an ice-salt bath to below −5° C., added potassium tert-butoxide (4 g, 35.6 mmol) in four portions. After the addition, warmed to room temperature and stirred for 1 hour, then cooled to −5° C. To the suspension was added dropwise a solution of tert-butyl 3-oxocyclobutylcarbamate (Compound 3-1) (5 g, 27 mmol) dissolved in 40 mL of tetrahydrofuran. After the addition, warmed to room temperature and stirred for 2 hours, then suction filtered to remove insolubles, rotary evaporated to remove solvents, the resulting residue was purified by silica gel column chromatography (petroleum ether/ethyl acetate=10:1), to give Compound 3-2 (3.5 g, yield 70.7%).

2) tert-Butyl spiro[2.3]hexan-5-ylcarbamate (Compound 3-3)

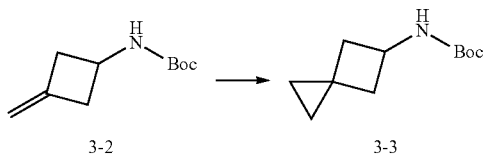

Diethyl zinc (40 mL, 1N hexane solution) was added to 100 mL of anhydrous dichloromethane under nitrogen. After the addition, cooled to −78° C. with dry ice-acetone, and diiodomethane (15 g, 56 mmol) was slowly added dropwise. After the addition stirring was continued for 30 minutes, and then changed into the ice-water bath. A solution of Compound 3-2 (1.7 g, 9.3 mmol) dissolved in 100 mL of dichloromethane was further added dropwise and stirred overnight, added 200 mL of water to quench the reaction, liquid separated, and the aqueous phase was extracted with 200 mL of dichloromethane three times. The organic phases were combined, rotary evaporated to remove solvents, and purified by silica gel column chromatography (petroleum ether/ethyl acetate=10:1) to give
Compound 3-3 (1.03 g, 56.1% yield).

3) Spiro[2.3]hexan-5-amine trifluoroacetate (Compound 3-4)

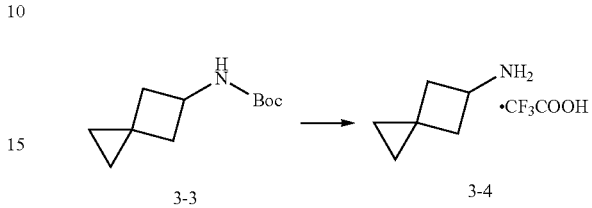

The above obtained Compound 3-3 (1 g, 5.1 mmol) was dissolved in 5 mL of trifluoroacetic acid, stirred for 10 minutes, rotary evaporated to remove trifluoroacetic acid to give 1.1 g of Compound 3-4 and used directly in the next step reactions.

4) Compound 3

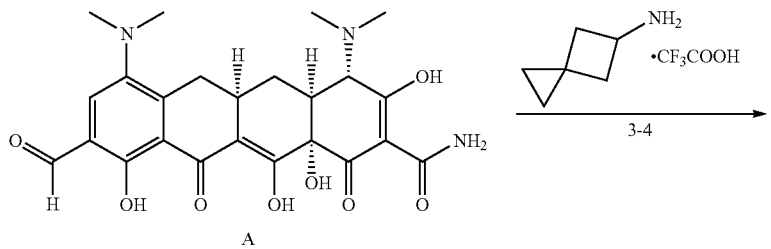

A

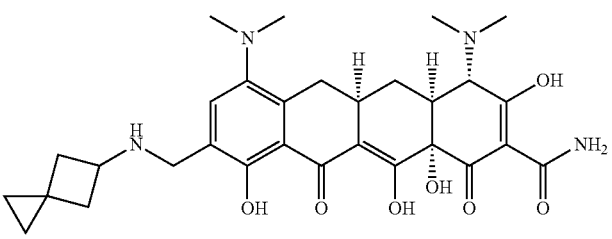

Compound 3

Compound A (0.5 g, 1.03 mmol) was dissolved in DMF (10 mL), added Compound 3-4 (0.7 g, 3.3 mmol), triethylamine (500 mg, 5 mmol) and anhydrous indium trichloride (10 mg), and the mixture was stirred at room temperature for 30 minutes, added sodium cyanoborohydride (0.3 g, 4.8 mmol), then stirred at room temperature for 0.5 h, separated by HPLC to give Compound 3 (41 mg).

$^1$H-NMR (D$_2$O, 400 MHz) δ: 7.82 (s, 1H), 4.08 (s, 2H), 3.92 (s, 1H), 3.84 (s, 1H), 3.10 (s, 7H), 2.73-2.98 (m, 8H), 2.42 (m, 1H), 2.38 (m, 2H), 2.13 (m, 3H), 1.45-1.60 (m, 1H), 0.30 (m, 4H)

Example 5

Preparation of (4S,4aS,5aR,12aS)-9-((spiro[3.3]heptan-2-ylmethylamino)methyl)-4,7-bis(dimethylamino)-3,10,12,12a-tetrahydroxy-1,1-dioxo-1,4,4a,5,5a,6,11,12a-octahydrotetracene-2-carboxamide (Compound 4)

1) 3-methylenecyclobutylmethylamine (Compound 4-2)

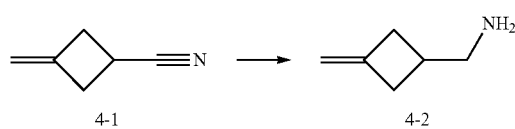

AlLiH$_4$ (2.45 g, 64.5 mmol) was dissolved in 50 mL of anhydrous tetrahydrofuran, added a solution of 3-methylenecyclobutylcarbonitrile (compound 4-1) (5 g, 53.7 mmol) dissolved in 20 mL of tetrahydrofuran, heated to reflux and stirred for 2 hours. After cooling, water (5 mL, 0.7 mmol) was slowly added dropwise under cooling in an ice-water bath, after the completion of addition, stirring was continued for 2 hours, and filtrated through Celite to remove insolubles. The resulting filtrate was rotary evaporated to remove solvents to give Compound 4-2 (3.5 g, 67.1% yield).

2) Benzyl 3-methylenecyclobutylmethylcarbamate (Compound 4-3)

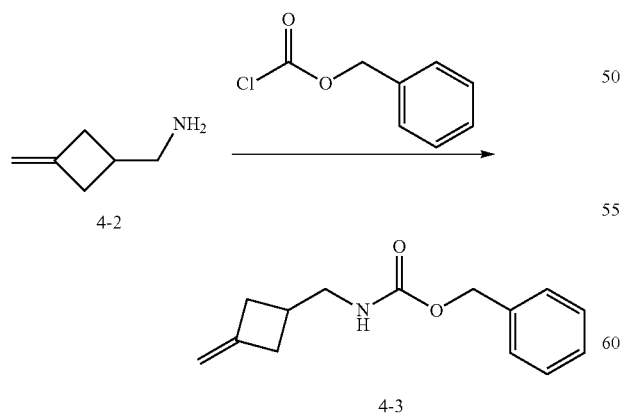

Compound 4-2 (3 g, 30.9 mmol) was dissolved in 50 mL of tetrahydrofuran, added Na$_2$CO$_3$ (6.3 g, 60 mmol) and benzyl chloroformate (5.25 g, 30.8 mmol). The mixture was stirred for 12 hours at room temperature, added 100 mL of water, extracted three times with 300 mL of ethyl acetate, combined the organic phases, rotary evaporated to remove solvents and purified by column chromatography (petroleum ether/ethyl acetate=10:1) to give Compound 4-3 (4 g, 56% yield).

3) Benzyl (5,5-dichloro-6-oxospiro[3.3]heptan-2-yl)methylcarbamate (Compound 4-4)

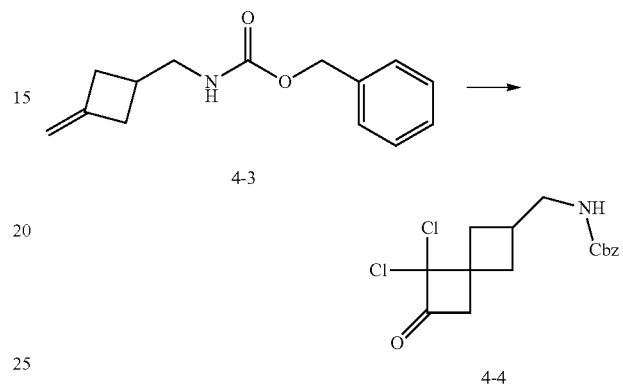

Compound 4-3 (3 g, 12.98 mmol) and zinc-copper alloy (7.78 g, 64.9 mmol) were placed in 100 mL of diethyl ether, added dropwise a solution of CCl$_3$COCl (6.97 g, 38.33 mmol) dissolved in 15 mL of DMA with stirring slowly. After the completion of addition, the mixture was stirred at room temperature for 18 hours. To the reaction mixture was poured 100 mL of saturated aqueous solution of sodium bicarbonate, and suction filtrated to remove insolubles, liquid separated, the aqueous phase was extracted with diethyl ether. The organic phases were combined, dried over anhydrous sodium sulfate, suction filtrated to remove the desiccant, and rotary evaporated to remove solvents, the resulting crude Compound 4-4 was used directly in the next reaction.

4) Benzyl (6-oxospiro[3.3]heptan-2-yl)methylcarbamate (Compound 4-5)

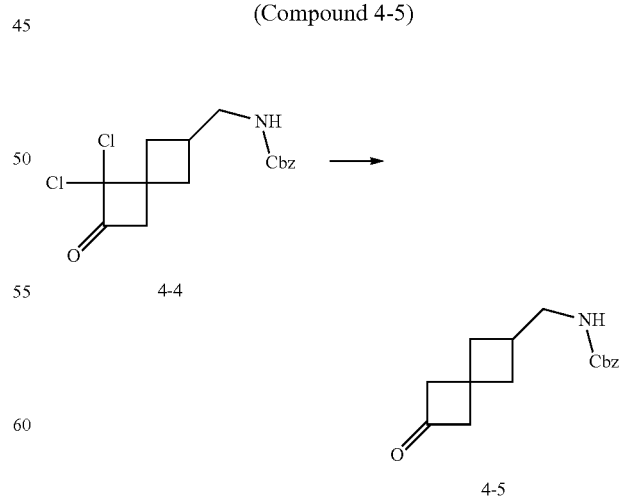

The above obtained Compound 4-4, zinc powder (2.18 g, 33.3 mmol) and NH$_4$Cl (1.38 g, 25.8 mmol) were added to 50 mL of methanol and refluxed for 4 hours. Suction filtered to remove insolubles, and rotary evaporated to remove solvents. The mixture was purified by column chromatography (petroleum ether/ethyl acetate=5:1) to give Compound 4-5 (2.1 g, yield 59.2% (two steps)).

5) Spiro[3.3]heptan-2-ylmethylamine (Compound 4-6)

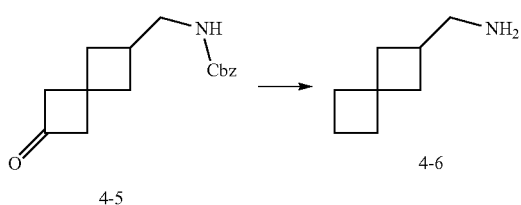 [SMILES: O=C1CC2(C1)CC(CNC(=O)OCc1ccccc1)C2 ; NCC1CC2(CCC2)C1]

Compound 4-5 (2 g, 7.32 mmol) and hydrazine monohydrate (0.828 g, 16.5 mmol) and NaOH (0.585 g, 14.63 mmol) were added to triethylene glycol (20 mL) and heated under reflux for 1 hour. Then remove the condenser, heated to 200° C. in an oil bath and maintained for 3 hours, and after cooling purified by column chromatography to give Compound 4-6 (0.67 g, 73% yield).

6) Synthesis of Compound 4

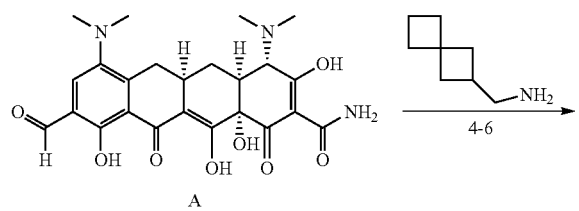

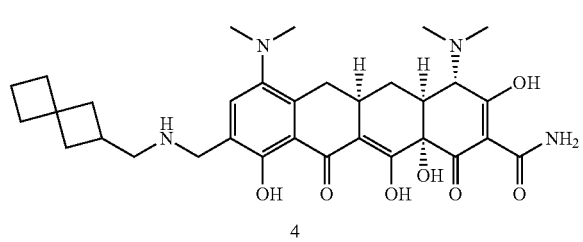

Compound A (0.230 g, 0.474 mmol), Compound 4-6 (0.65 g, 5.2 mmol), triethylamine (500 mg, 5 mmol) and anhydrous indium trichloride (10 mg) were dissolved in DMF and stirred for 1 hour, added sodium cyanoborohydride (0.090 g, 1.43 mmol) and stirred for 4 hours, then separated by a reverse-phase preparative chromatography to give Compound 4 (13 mg).

$^1$H-NMR (D$_2$O, 400 MHz) δ: 7.69 (s, 1H), 4.12-4.27 (m, 2H), 3.77-3.88 (m, 1H), 2.73-3.07 (m, 17H), 2.41-2.45 (m, 1H), 2.19 (m, 1H), 2.05-2.14 (m, 1H), 1.87-1.96 (m, 2H), 1.74-1.82 (m, 2H), 1.58-1.73 (m, 7H)

Example 6

Preparation of (4S,4aS,5aR,12aS)-9-((spiro[2.5]octan-6-ylamino)methyl)-4,7-bis(dimethylamino)-3,10,12,12a-tetrahydroxy-1,1'-dioxo-1,4,4a,5,5a,6,11,12a-octahydrotetracene-2-carboxamide (Compound 7)

1) tert-Butyl 4-methylenecyclohexylcarbamate (Compound 7-2)

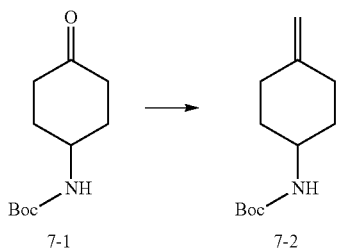

Triphenylmethylphosphonium bromide (53.7 g, 0.15 mol) was dissolved in 500 mL of tetrahydrofuran, potassium tert-butoxide (16.8 g, 0.15 mol) was added at −20° C., reacted for 0.5 h after the temperature was raised to 0° C. Then, tert-butyl 4-oxo-cyclohexylcarbamate (Compound 7-1) (21.3 g, 0.1 mol) was dissolved in 100 mL of THF and added dropwise into the flask under nitrogen. After 3 hours of reaction at room temperature, a small amount of water was added to dissolve the solids. The mixture was rotary evaporated to remove THF, extracted with anhydrous diethyl ether, and dried, concentrated, the concentrate was dissolved in n-hexane, and filtered by silica gel, then concentrated to give Compound 7-2 as a colorless liquid (19.5 g, 92.3% yield).

2) tert-Butyl spiro[2.5]octan-6-ylcarbamate (Compound 7-3)

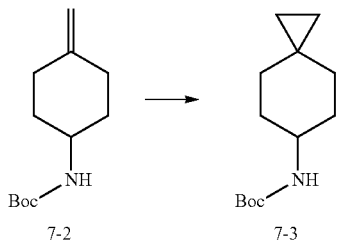

Diethyl zinc (40 mL, 1 M solution in hexane) was slowly added to 300 mL of anhydrous DCM at −78° C. under nitrogen, further dimethyl iodide (15 g, 56 mmol) was added slowly. After 30 minutes, warmed to room temperature and maintained for 30 minutes, cooled with an ice-water bath. Then a solution of Compound 7-2 (2 g, 9.5 mmol) dissolved in 10 mL of methylene chloride was added and reacted overnight. To the reaction mixture was poured 100 mL of saturated aqueous solution of ammonium chloride, and liquid separated, the organic phase was extracted with ethyl acetate (100 mL) twice, the organic phases were combined and dried over anhydrous sodium sulfate. Suction filtered to remove desiccant, and rotary evaporated to remove solvents. The residue was purified by silica gel column chromatography (petroleum ether/ethyl acetate=10:1) to give Compound 7-3 as a white solid (0.8 g, 37.4% yield).

3) Spiro[2.5]octan-6-amine trifluoroacetate (Compound 7-4)

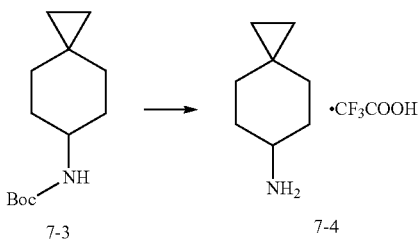 [SMILES: CC(C)(C)OC(=O)NC1CCC2(CC1)CC2 ; NC1CCC2(CC1)CC2 ; "·CF3COOH"]

Compound 7-3 (1.5 g, 6.7 mmol) was dissolved in 15 mL of DCM and TFA (2.5 mL) was added and stirred for 1 hour to give Compound 7-4 (1.6 g, 99.8% yield).

4) Compound 7

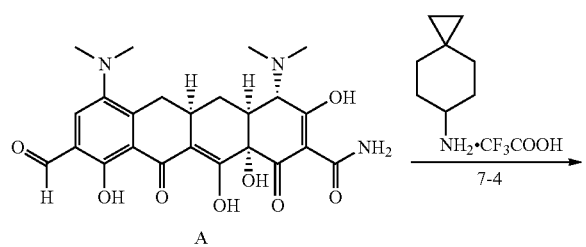

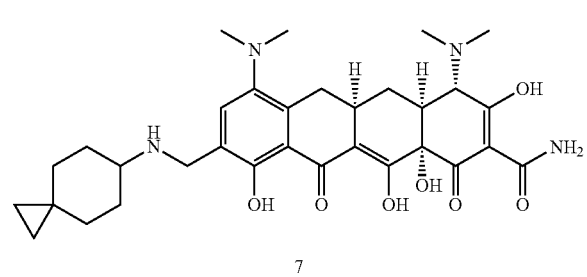

Compound A (1.0 g, 2.1 mmol), Compound 7-4 (300.0 mg, 1.25 mmol), 1 mL of TEA and 10 mg of anhydrous indium trichloride were dissolved in 10 mL of DMF and reacted at room temperature for 0.5 h, 400 mg of sodium triacetoxyborohydride were added slowly and the reaction was continued for 1.5 hours. The reaction solution was diluted with 1 L of water, and separated using reverse-phase preparative column to obtain 600 mg of crude product. The crude product was further purified by semi-preparative high-pressure chromatography to give Compound 7 (83 mg).

$^{1}$H-NMR (D$_{2}$O, 400 MHz) δ: 7.48 (s, 1H), 4.28 (br. s., 2H), 3.75 (s, 1H), 2.98-3.19 (m, 2H), 2.69-2.95 (m, 7H), 2.45-2.65 (m, 8H), 2.28 (m, 1H), 2.13 (m, 1H), 2.01 (m, 2H), 1.40-1.76 (m, 6H), 0.93 (m, 2H), 0.25 (m, 2H), 0.16 (m, 2H)

Example 7

Preparation of (4S,4aS,5aR,12aS)-9-((spiro[2.5]octan-6-ylmethylamino)methyl)-4,7-bis(dimethylamino)-3,10,12,12a-tetrahydroxy-1,11-dioxo-1,4,4a,5,5a,6,11,12a-octahydrotetracene-2-carboxamide (Compound 8)

1) Ethyl 4-methylenecyclohexylcarboxylate (Compound 8-2)

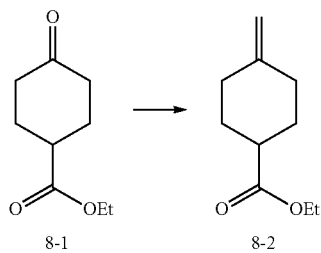

Triphenylmethylphosphonium bromide (53.7 g, 0.15 mol) was dissolved in 500 mL of THF, and potassium tert-butoxide (16.8 g, 0.15 mol) was added at −20° C. Reacted for 0.5 h after the temperature was raised to 0° C. Subsequently, ethyl 4-oxo-cyclohexylcarboxylate (Compound 8-1) (17 g, 0.1 mol) was dissolved in 100 mL of THF and added dropwise to the flask under nitrogen, reacted at room temperature for 3 hours, then a small amount of water was added to dissolve the solid, and rotary evaporated to remove THF, extracted with anhydrous diethyl ether, dried, and concentrated, the concentrate was dissolved in n-hexane, and filtered by silica gel, then concentrated to give Compound 8-2 as a colorless liquid (16.1 g, 95.7% yield).

2) 4-methylenecyclohexanecarboxamide (Compound 8-3)

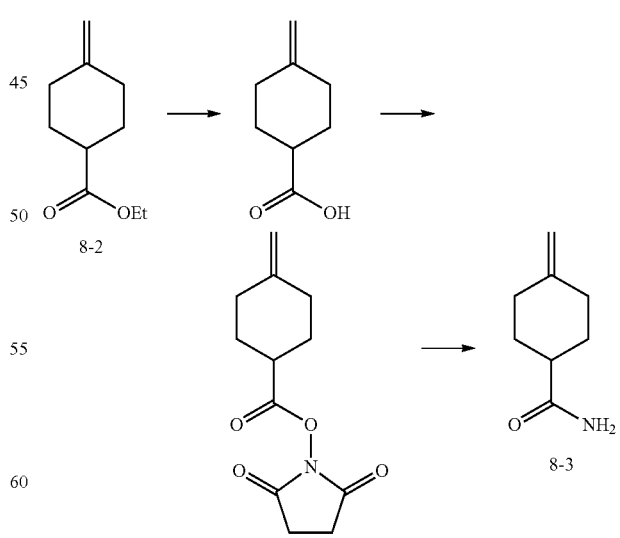

Compound 8-2 (16.1 g, 0.096 mol) and sodium hydroxide (8 g, 0.2 mol) were dissolved in a mixed solvent of 100 mL of methanol and water (volume ratio 1:1), reacted at 50° C. for 0.5 h, and rotary evaporated to remove methanol. Then added 200 mL of water, and adjusted the pH to acidic, extracted with dichloromethane, washed with saturated brine, and then dried over anhydrous sodium sulfate, the desiccant was removed by filtration, the solvent was removed by rotary evaporation, and concentrated to give a white solid.

The above obtained white solid and N-hydroxysuccinimide (13.2 g, 0.115 mol) were dissolved in 200 mL of DCM, DCC (23.65 g, 0.114 mol) was added slowly at −10° C. After the addition, the reaction mixture was stirred for 1 hour at room temperature, suction filtered, and rotary evaporated to remove solvents. The resulting residue was dispersed in 200 mL of ammonia cooled with an ice-water bath, and then heated to 80° C., maintained at that temperature for 2 hours, and then pressurized to remove most of the ammonia gas, and extracted with ethyl acetate, dried and concentrated, then crystallized from ethyl acrylate/petroleum ether to give Compound 8-3 (9.5 g, 71.1% yield).

3) Benzyl 4-methylenecyclohexylmethylcarbamate (Compound 8-4)

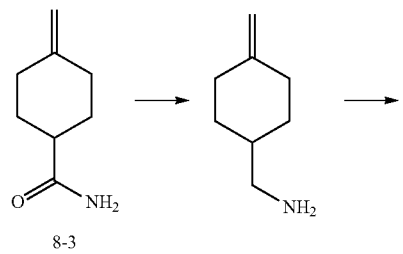

Compound 8-3 (9.5 g, 0.068 mol) was dissolved in 300 mL of THF, and lithium aluminium hydride (2.62 g, 0.069 mol) was added slowly at −10° C. After the addition, reacted at room temperature for 2 hours, and added 5 mL of water after completion of the reaction of raw materials, suction filtered through Celite and the filtrate was concentrated to give an oil. The obtained oil and triethylamine (10.7 mL, 0.075 mol) were dissolved in 100 mL of DCM, and added dropwise benzyl chloroformate (11.6 g, 0.068 mol) slowly at −10° C., then further reacted for 2 hours at room temperature after the addition was completed. The reaction mixture was washed with 100 mL of water and 100 mL of saturated brine once respectively, dried and concentrated and purified by column chromatography (petroleum ether/ethyl acetate=10:1) to give Compound 8-4 as a white solid (6.3 g, yield 35.7%).

4) Benzyl spiro[2.5]octan-6-ylmethylcarbamate (Compound 8-5)

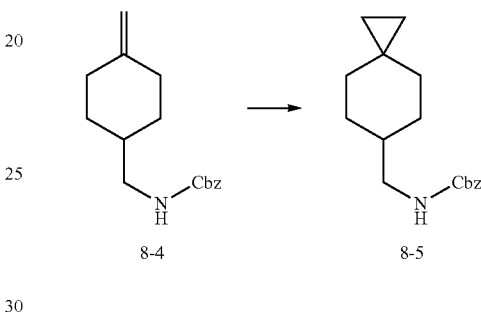

Diethyl zinc (25 mL, 1M hexane solution) was slowly added to 100 mL of anhydrous DCM at −40° C. under nitrogen, and further slowly added TFA (2.85 g, 0.025 mol) and reacted for 0.5 h, then diiodomethane (6.67 g, 0.025 mol) was slowly added thereto. The reaction was continued for 0.5 h, then Compound 8-4 (3 g, 0.012 mol) was dissolved in 20 mL of anhydrous DCM and added dropwise to the reaction mixture under nitrogen, reacted overnight at −5° C., added saturated ammonium chloride solution to quench the reaction, followed by liquid separated, the organic phase was concentrated and purified by column chromatography (petroleum ether/ethyl acetate=10:1) to give Compound 8-5 as a white solid (2.85 g, yield 86.9%).

5) Spiro[2.5]octan-6-ylmethylamine hydrochloride (Compound 8-6)

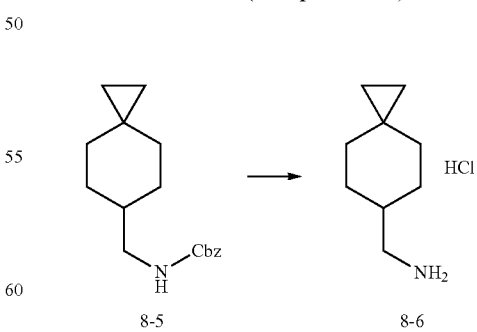

Compound 8-5 (2.85 g, 10.4 mmol) was dissolved in 30 mL of methanol, added 0.2 g of palladium on carbon and 1 mL of concentrated hydrochloric acid, and subjected to catalytic hydrogenation reaction overnight and filtered to remove insolubles, then concentrated to give Compound 8-6 (1.8 g, yield 98.5%).

6) Compound 8

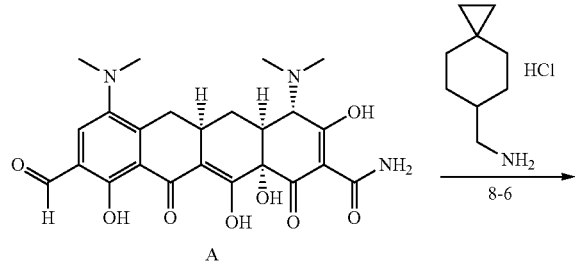

A 8-6

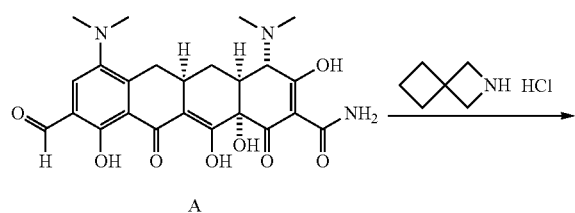

8

Compound A (1 g, 2.06 mmol), Compound 8-6 (1 g, 5.69 mmol), 2 mL of TEA and 30 mg of anhydrous indium trichloride were dissolved in 10 mL of DMF, reacted at room temperature for 0.5 h, then slowly added 1 g of sodium cyanoborohydride, and further reacted for 0.5 h. The reaction mixture was diluted with 1 L of water, separated by reverse-phase preparative chromatography to give Compound 8 (320 mg).

$^1$H-NMR (CD$_3$OD, 400 MHz) δ: 7.52 (s, 1H), 4.20-4.32 (m, 2H), 3.62 (br. s., 1H), 3.41-3.35 (m, 1H), 2.98 (m, 4H), 2.81 (m, 5H), 2.54-2.75 (m, 7H), 2.06-2.28 (m, 2H), 1.59-1.86 (m, 6H), 1.17-1.25 (m, 2H), 0.89-1.03 (m, 2H), 0.17-0.36 (m, 4H)

Example 8

Preparation of (4S,4aS,5aR,12aS)-9-(2-azaspiro[3.3]heptan-2-ylmethyl)-4,7-bis(dimethylamino)-3,10,12,12a-tetrahydroxy-1,1'-dioxo-1,4,4a,5,5a,6,11,12a-octahydrotetracene-2-carboxamide (Compound 9)

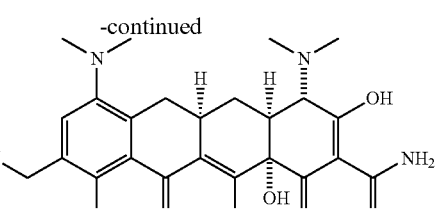

A

-continued

9

Compound A (0.230 g, 0.474 mmol) was dissolved in DMF (2 mmol), and added 2-azaspiro[3.3]heptane hydrochloride (0.126 g, 0.948 mmol) and triethylamine (180 mg, 1.8 mmol). After the mixture was stirred at room temperature for 30 minutes, added sodium cyanoborohydride (0.2 g, 1.7 mmol), then stirred for 4 hours at room temperature, separated by HPLC to give Compound 9 (60 mg).

$^1$H-NMR (CD$_3$OD, 400 MHz) δ: 7.57 (s, 1H), 4.35 (br. s., 2H), 4.16 (br. s., 4H), 3.69 (s, 1H), 3.34-3.50 (m, 1H), 2.82-2.97 (m, 7H), 2.77 (d, 1H), 2.56-2.70 (m, 6H), 2.29 (t, 4H), 2.20 (d, 2H), 1.85 (m, 2H), 1.57-1.71 (m, 1H)

Example 9

Preparation of (4S,4aS,5aR,12aS)-9-(((3,3-difluorocyclobutyl)methylamino)methyl)-4,7-bis(dimethylamino)-3,10,12,12a-tetrahydroxy-1,11-dioxo-1,4,4a,5,5a,6,11,12a-octahydrotetracene-2-carboxamide (Compound 10)

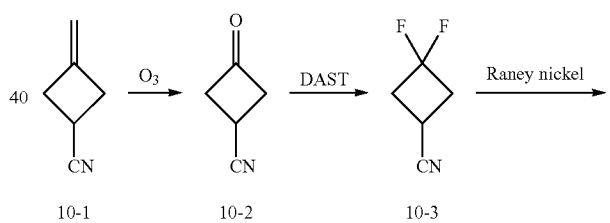

10

1) 3-oxocyclobutanecarbonitrile (Compound 10-2)

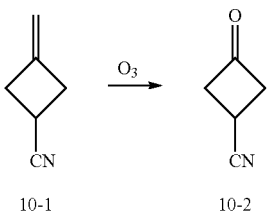

Compound 10-1 (10 g, 0.108 mol) was dissolved in a mixed solvent of 50 mL of MeOH and 50 mL of DCM. To the reaction system was blown $O_3$ gas, cooled to −78° C., the solution became blue. The end of the reaction was monitored with TLC (petroleum ether/ethyl acetate=2:1). To the reaction system was blown $O_2$ gas for 0.5 h, and then $N_2$ gas for 0.5 h to remove the excess $O_3$ gas. 15 mL of $Me_2S$ was added to quench the reaction, and stirred at room temperature overnight, rotary dried to give the crude product, then purified by silica gel column chromatography (petroleum ether/ethyl acetate=15: 1-7:1) to give Compound 10-2 (7.5 g, yield 73.0%) as a white solid.

2) 3,3-difluorocyclobutanecarbonitrile (Compound 10-3)

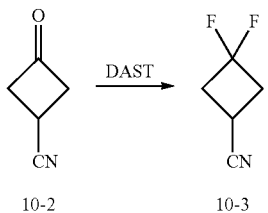

Compound 10-2 (8.0 g, 84.21 mmol) was dissolved in DCM (80 mL) at 0° C., added DAST (27 g, 0.168 mol). The reaction mixture was stirred overnight at room temperature, and the end of the reaction was monitored by TLC (petroleum ether/ethyl acetate=3:1). Ice water was added to the reaction solution, extracted with DCM, washed with saturated brine, and then dried over anhydrous $Na_2SO_4$. The organic layer was concentrated under reduced pressure and purified by column chromatography (petroleum ether/ethyl acetate=150: 1-30:1) to give the crude Compound 10-3 (8.1 g) as a brown oil.

3) 3,3-difluorocyclobutylmethylamine hydrochloride (Compound 10-4)

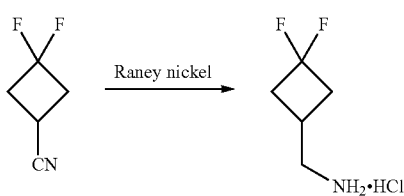

Compound 10-3 (7.0 g, 59.78 mmol), $NH_3 \cdot H_2O$ (7 mL) and Raney nickel (7.0 g, 100%/W) were dissolved in ethanol (70 mL) and the mixture was stirred for 3 hours in $H_2$ (50 psi) atmosphere at room temperature. Then the mixture was filtered, added 10 mL of 4M hydrochloric acid methanol solution, and concentrated to give Compound 10-4 (5.5 g, 58.4%) as a white solid.

4) Compound 10

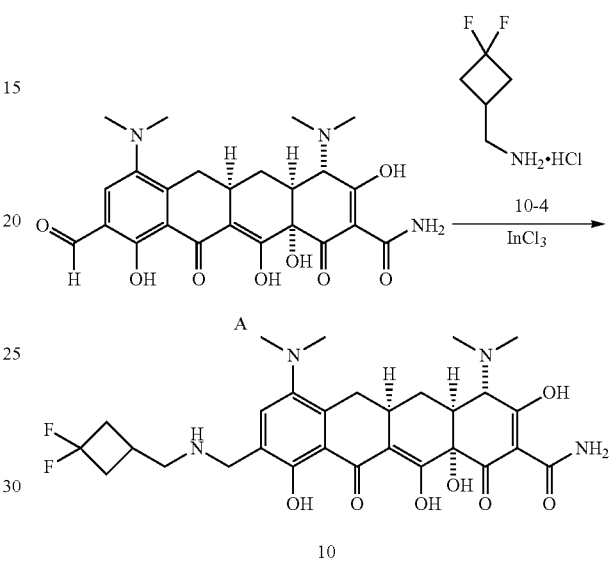

Compound A (1.0 g, 2.06 mmol), Compound 10-4 (0.65 g, 4.12 mmol), $Et_3N$ (0.416 g, 4.12 mmol) and $InCl_3$ (91 mg, 0.41 mmol) were dissolved in DMF (10 mL) and the mixture was stirred at room temperature for 2 hours. $NaBH_3CN$ (260 mg, 4.14 mmol) was added, and the mixture was stirred at room temperature overnight, purified by preparative chromatography to give Compound 10 (0.5 g) as a yellow solid.

LC-MS (M+H): 591.3 (Found)

$^1$H-NMR ($D_2O$, 400 MHz) δ: 7.95 (s, 1H), 4.32 (s, 2H), 4.11 (s, 1H), 3.37-3.28 (m, 3H), 3.20-2.92 (m, 13H), 2.79 (m, 2H), 2.65-2.54 (m, 1H), 2.52-2.40 (m, 4H), 2.31-2.15 (m, 1H), 1.68 (m, 1H)

Example 10

Preparation of (4S,4aS,5aR,12aS)-9-(4-azaspiro[2.4] heptan-4-ylmethyl)-4,7-bis(dimethylamino)-3,10,12, 12a-tetrahydroxy-1,1'-dioxo-1,4,4a,5,5a,6,11,12a-octahydrotetracene-2-carboxamide (Compound 11)

1) 4-azaspiro[2.4]heptane trifluoroacetate (Compound 11-2)

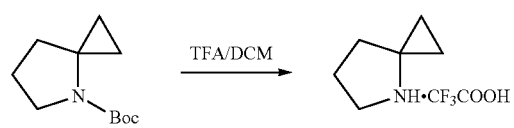

tert-Butyl 4-azaspiro[2.4]heptane-4-carboxylate (Compound 11-1) (0.75 g, 3.80 mmol) and TFA (3 mL) were added in DCM (10 mL) and the mixture was stirred at room temperature for 1 hour and concentrated to give Compound 11-2 (800 mg, 99.6%) as a yellow oil.

2) Compound 11

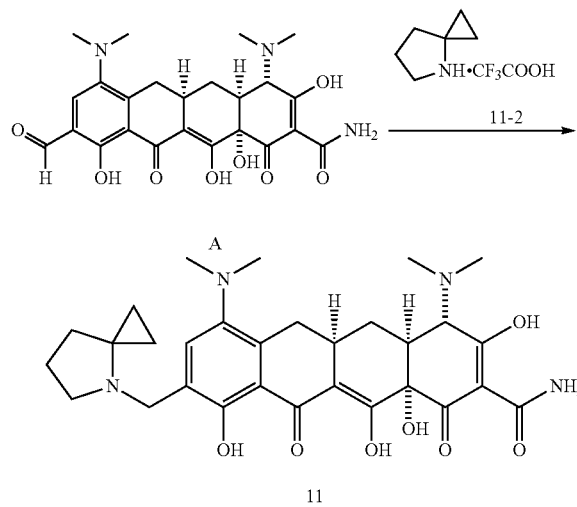

Compound A (0.8 g, 1.65 mmol), Compound 11-2 (0.7 g, 3.30 mmol), Et₃N (0.33 g, 3.30 mmol) and InCl₃ (73 mg, 0.33 mmol) were dissolved in DMF (8 mL), and stirred at room temperature for 2 hours. NaBH₃CN (0.21 g, 3.30 mmol) was added, and the mixture was stirred at room temperature overnight, purified by preparative chromatography to give Compound 11 (0.21 g) as a yellow solid.

LC-MS (M+H): 567.3 (Found)

$^1$H-NMR (CD$_3$OD, 400 MHz) δ: 7.71 (d, 1H), 4.30-4.23 (m, 2H), 4.08 (s, 1H), 3.49-3.36 (m, 3H), 3.25-2.85 (m, 9H), 2.76 (m, 5H), 2.48-1.90 (m, 6H), 1.65 (m, 2H), 1.39 (m, 1H), 1.02 (m, 2H)

Example 11

Preparation of (4S,4aS,5aR,12aS)-4,7-bis(dimethylamino)-3,10,12,12a-tetrahydroxy-9-(((3-methyloxetan-3-yl)methylamino)methyl)-1,1'-dioxo-1,4,4a,5,5a,6,11,12a-octahydrotetracene-2-carboxamide (Compound 14)

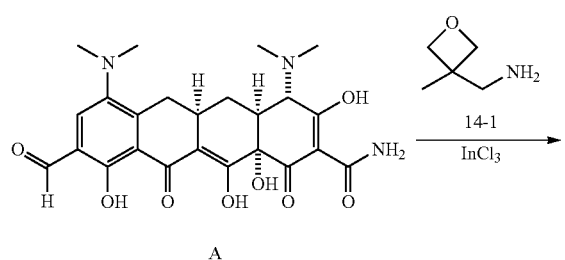

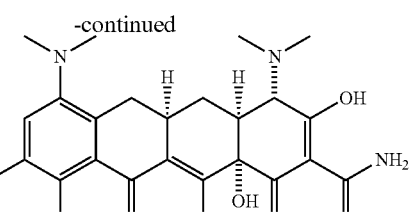

Compound A (0.8 g, 1.65 mmol), (3-methyl-oxetan-3-yl)methylamine (Compound 14-1) (333 mg, 3.30 mmol) and InCl₃ (73 mg, 0.33 mmol) were dissolved in DMF (8 mL), and stirred at room temperature for 2 hours. NaBH₃CN (208 mg, 3.30 mmol) was added, and the mixture was stirred at room temperature overnight, purified by preparative chromatography to give Compound 14 (0.4 g) as a yellow solid.

LC-MS (M+H): 571.3 (Found)

$^1$H-NMR (D$_2$O, 400 MHz) δ: 7.67 (s, 1H), 4.50 (m, 2H), 4.42 (m, 2H), 4.34 (m, 2H), 4.09 (s, 1H), 3.44 (m, 3H), 2.89-3.12 (m, 8H), 2.74 (s, 6H), 2.15-2.40 (m, 2H), 1.67 (m, 1H), 1.46 (s, 3H)

Example 12

Preparation of (4S,4aS,5aR,12aS)-9-((6,6-difluoro-2-azaspiro[3.3]heptan-2-yl)methyl)-4,7-bis(dimethylamino)-3,10,12,12a-tetrahydroxy-1,1'-dioxo-1,4,4a,5,5a,6,11,12a-octahydrotetracene-2-carboxamide (Compound 16)

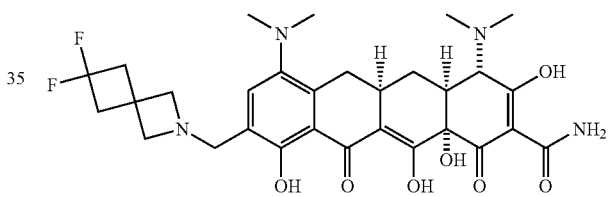

The entitled compound was prepared according to the same method of Example 8 but replacing 2-azaspiro[3.3]heptane hydrochloride with 6,6-difluoro-2-azaspiro[3.3]heptane hydrochloride.

$^1$H-NMR (CD$_3$OD, 400 MHz) δ: 7.48-7.57 (m, 1H), 4.40-4.49 (m, 2H), 4.24-4.36 (m, 4H), 4.02-4.13 (m, 1H), 3.37-3.50 (m, 1H), 2.85-3.05 (m, 10H), 2.56-2.70 (m, 8H), 2.14-2.33 (m, 2H), 1.57-1.75 (m, 1H)

Example 13

Preparation of (4S,4aS,5aR,12aS)-9-(2-oxa-6-azaspiro[3.3]heptan-6-ylmethyl)-4,7-bis(dimethylamino)-3,10,12,12a-tetrahydroxy-1,1'-dioxo-1,4,4a,5,5a,6,11,12a-octahydrotetracene-2-carboxamide (Compound 17)

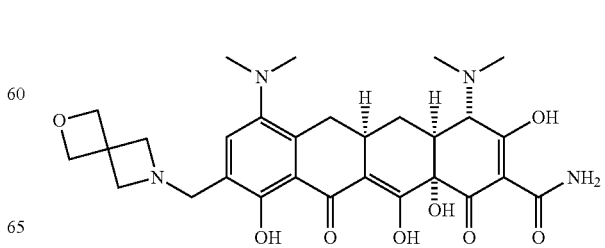

The entitled compound was prepared according to the same method of Example 8 but replacing 2-azaspiro[3.3]heptane hydrochloride with 2-oxa-6-azaspiro[3.3]heptane hydrochloride.

$^1$H-NMR (D$_2$O, 400 MHz) δ: 7.85 (s, 1H), 4.27-4.37 (m, 2H), 3.80-4.00 (m, 4H), 3.51 (s, 2H), 3.41 (s, 2H), 2.65-3.20 (m, 15H), 2.40 (m, 1H), 2.09 (m, 1H), 1.50 (m, 1H)

Example 14

Preparation of (4S,4aS,5aR,12aS)-9-((3,3-difluoroazetidin-1-yl)methyl)-4,7-bis(dimethylamino)-3,10,12,12a-tetrahydroxy-1,1'-dioxo-1,4,4a,5,5a,6,11,12a-octahydrotetracene-2-carboxamide (Compound 18)

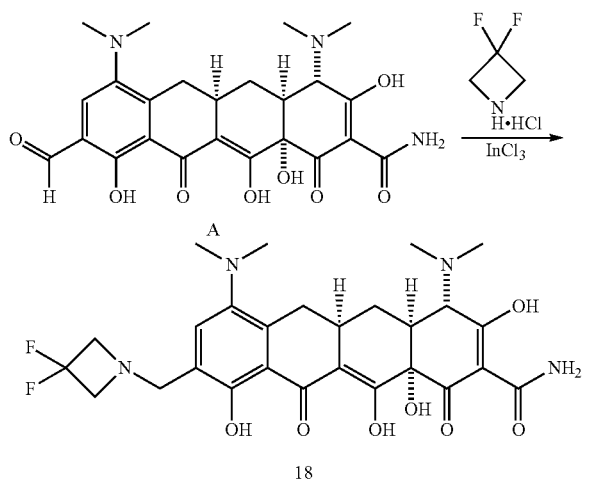

Compound A (0.8 g, 1.65 mmol), 3,3-difluoroazetidine hydrochloride (0.43 g, 3.30 mmol), Et$_3$N (0.33 g, 3.30 mmol) and InCl$_3$ (73 mg, 0.33 mmol) were dissolved in DMF (10 mL). The mixture was stirred at room temperature for 2 hours, added NaBH$_3$CN (208 mg, 3.30 mmol), and stirred at room temperature overnight, purified by preparative chromatography to give Compound 18 (0.377 g) as a yellow solid.

$^1$H-NMR (CD$_3$OD, 400 MHz) δ: 7.63 (br. s., 1H), 4.78 (m, 4H), 4.58 (br. s., 2H), 4.08 (br. s., 1H), 3.40 (m, 1H), 2.85-3.08 (m, 8H), 2.72 (s, 6H), 2.13-2.45 (m, 2H), 1.68 (m, 1H)

Example 15

Figure 2:
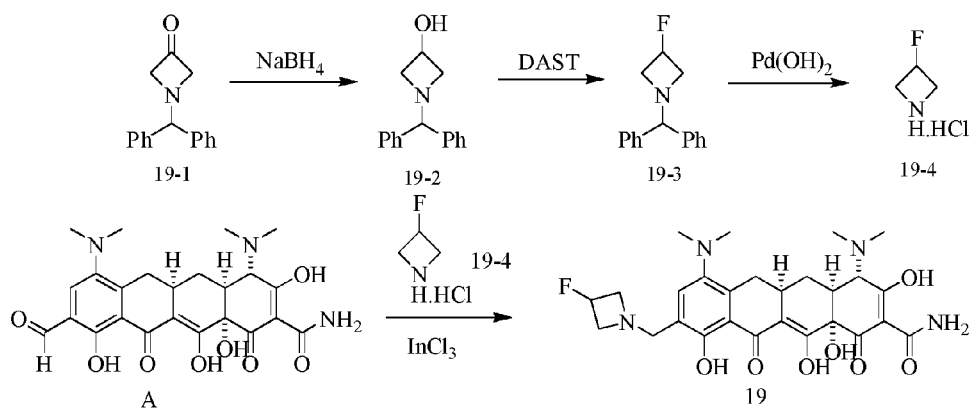
FIG. 2 is a synthetic scheme depicting a method for preparing Compound 19.

Preparation of (4S,4aS,5aR,12aS)-4,7-bis(dimethylamino)-9-((3-fluoroazetidin-1-yl)methyl)-3,10,12,12a-tetrahydroxy-1,11-dioxo-1,4,4a,5,5a,6,11,12a-octahydrotetracene-2-carboxamide (Compound 19): See FIG. 2

1) 1-benzhydrylazetidin-3-ol (Compound 19-2)

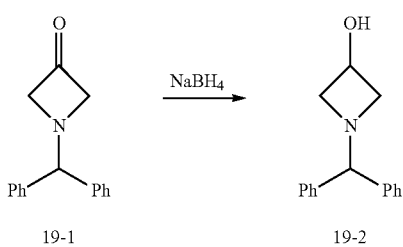 [SMILES: O=C1CN(C(c2ccccc2)c2ccccc2)C1 ; "NaBH4" ; OC1CN(C(c2ccccc2)c2ccccc2)C1]

NaBH$_4$ (2.39 g, 0.063 mol) was added portionwise to a solution of Compound 19-1 (15.0 g, 0.063 mol) in methanol (100 mL) at 0° C. The reaction mixture was stirred at room temperature for 2 hours, the end of the reaction was monitored with TLC (petroleum ether/ethyl acetate=3:1). The reaction mixture was poured into ice water, and concentrated under reduced pressure, extracted with ethyl acetate (100 mL×3), washed with saturated brine, dried over anhydrous Na$_2$SO$_4$, the dried organic layer was concentrated under reduced pressure to give Compound 19-2 (13.0 g, 86.2% yield) as a white solid.

2) 1-benzhydryl-3-fluoroazetidine (Compound 19-3)

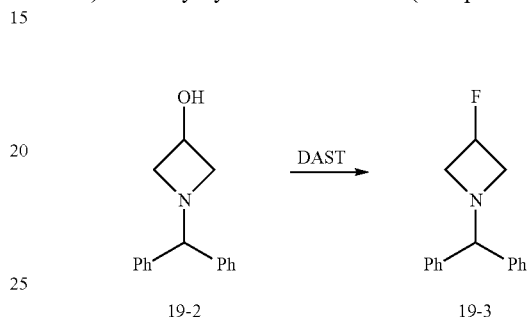

DAST (26.46 g, 0.164 mol) was added to a solution of Compound 19-2 (13.1 g, 0.0547 mol) in dry DCM (200 mL) at 0° C. The reaction mixture was stirred at room temperature overnight. The end of the reaction was monitored with TLC (petroleum ether/ethyl acetate=5:1). The reaction mixture was poured into ice water, extracted with DCM, washed with saturated brine, dried over anhydrous Na$_2$SO$_4$, and the organic layer was concentrated under reduced pressure, the resulting crude product was purified by column chromatography (petroleum ether/ethyl acetate=150:1) to give Compound 19-3 (4.0 g, 30% yield) as a white solid.

3) 3-fluoroazetidine hydrochloride (Compound 19-4)

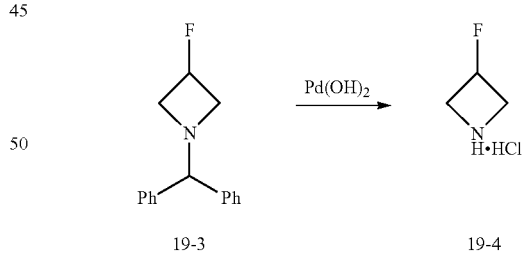

Pd(OH)$_2$ (8 g, 0.057 mol) was added to a solution of Compound 19-3 (6 g, 0.025 mol) in methanol (70 mL) under argon, evacuated to remove gases, and then purged with hydrogen gas for several times. The mixture was stirred overnight under H$_2$ (50 psi) at 30° C., the end of the reaction was monitored with TLC (petroleum ether/ethyl acetate=10:1). After filtration, to the filtrate was added dropwise 30 mL of 1 mol/L hydrochloric acid-methanol solution, and concentrated to give Compound 19-4 (1.96 g, 70.3% yield) as a white solid.

4) Compound 19

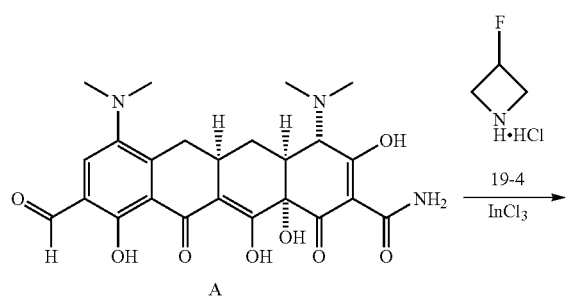

Compound A (0.8 g, 1.65 mmol), Compound 19-4 (0.366 g, 3.30 mmol), Et₃N (0.333 g, 3.30 mmol) and InCl₃ (73 mg, 0.33 mmol) were dissolved in DMF (15 mL) and stirred at room temperature for 2 hours, added NaBH₃CN (208 mg, 3.30 mmol), further stirred at room temperature overnight, purified by preparative chromatography to give Compound 19 (0.242 g) a yellow solid.

¹H-NMR (CD₃OD, 400 MHz) δ: 7.62 (br. s., 1H), 5.40 (m, 1H), 4.30-4.70 (m, 6H), 4.08 (s, 1H), 3.33 (m, 1H), 2.99 (m, 8H), 2.73 (m, 6H), 2.15-2.40 (m, 2H), 1.61 (m, 1H)

Example 16

Preparation of (4S,4aS,5aR,12aS)-9-(6-azaspiro[2.5]
octan-6-ylmethyl)-4,7-bis(dimethylamino)-3,10,12,
12a-tetrahydroxy-1,1'-dioxo-1,4,4a,5,5a,6,11,12a-
octahydrotetracene-2-carboxamide (Compound 20)

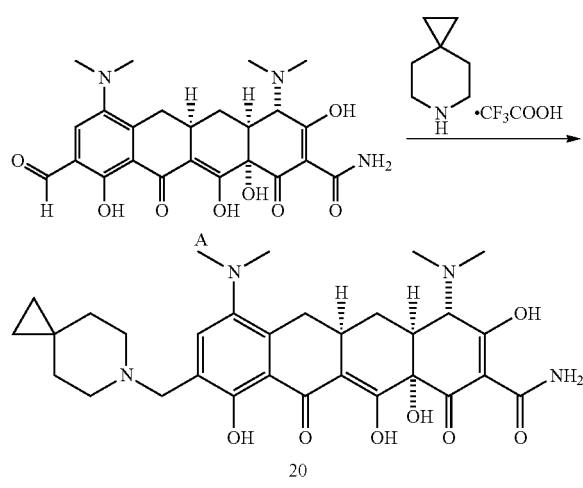

The entitled compound was prepared according to the same method of Example 10 Step 2) but replacing 4-azaspiro[2.4]heptane trifluoroacetate with 6-azaspiro[2.5]octane trifluoroacetate.

¹H-NMR (D₂O, 400 MHz) δ: 7.49-7.69 (m, 1H), 4.24 (br. s., 2H), 3.72 (s, 1H), 3.36 (m, 2H), 2.93-3.13 (m, 3H), 2.55-2.93 (m, 13H), 2.29 (m, 1H), 2.11 (m, 1H), 1.97 (m, 2H), 1.48-1.67 (m, 1H), 0.94-1.14 (m, 2H), 0.13-0.44 (m, 4H)

Example 17

Preparation of (4S,4aS,5aR,12aS)-9-(5-azaspiro[2.4]
heptan-5-ylmethyl)-4,7-bis(dimethylamino)-3,10,12,
12a-tetrahydroxy-1,1'-dioxo-1,4,4a,5,5a,6,11,12a-
octahydrotetracene-2-carboxamide (Compound 21)

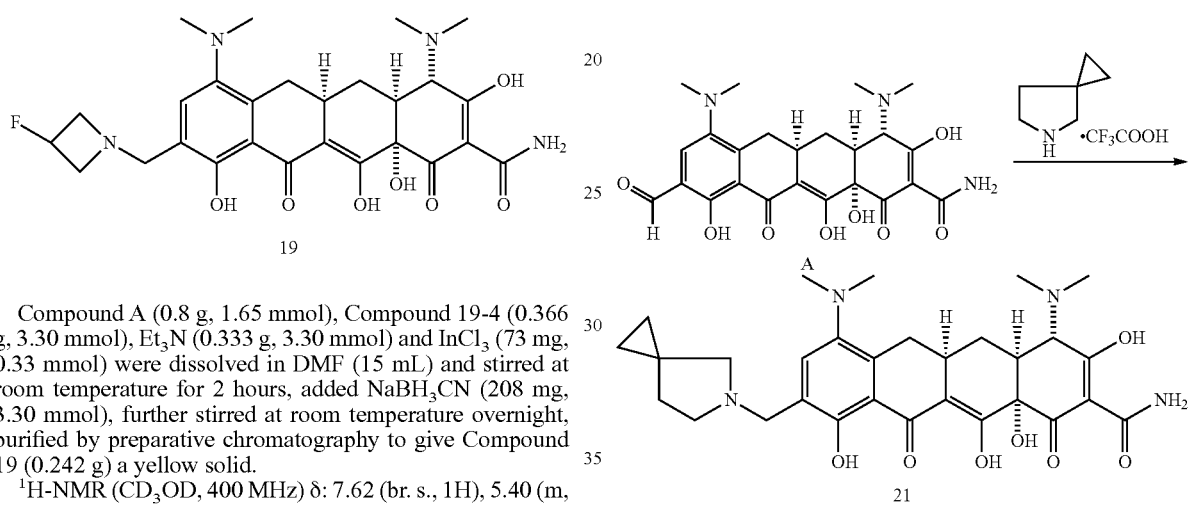

The entitled compound was prepared according to the same method of Example 10 Step 2) but replacing 4-azaspiro[2.4]heptane trifluoroacetate with 5-azaspiro[2.4]heptane trifluoroacetate.

¹H-NMR (CD₃OD, 400 MHz) δ: 7.44-7.58 (m, 1H), 4.64 (m, 1H), 4.20-4.45 (m, 2H), 3.49 (s, 2H), 3.09-3.27 (m, 4H), 2.48-2.85 (m, 11H), 1.94-2.11 (m, 4H), 1.48-1.64 (m, 1H), 0.64-0.81 (m, 4H)

Example 18

Preparation of (4S,4a-5,5aR,12a5)-9-(6-azaspiro[3.4]
octan-6-ylmethyl)-4,7-bis(dimethylamino)-3,10,12,
12a-tetrahydroxy-1,1'-dioxo-1,4,4a,5,5a,6,11,12a-
octahydrotetracene-2-carboxamide (Compound 22)

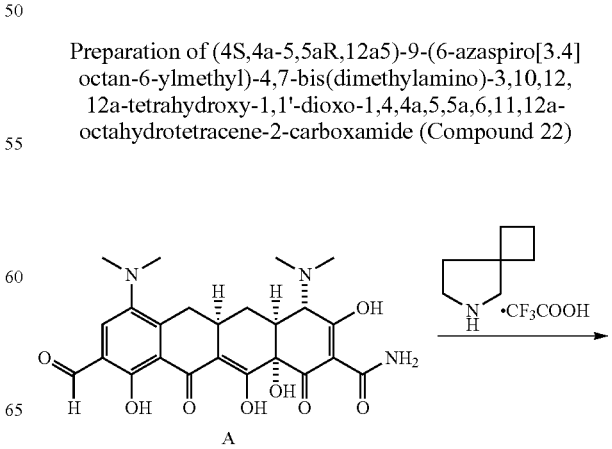

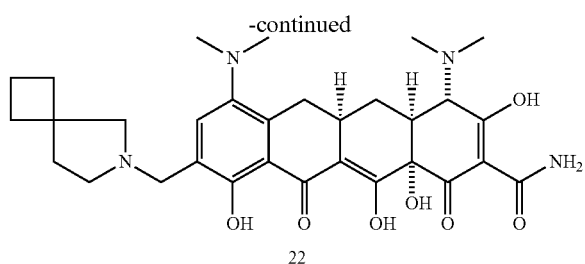

The entitled compound was prepared according to the same method of Example 10 Step 2) but replacing 4-azaspiro[2.4]heptane trifluoroacetate with 6-azaspiro[3.4]octane trifluoroacetate.

$^1$H-NMR (CD$_3$OD, 400 MHz) δ: 7.54 (s, 1H), 4.38 (s, 2H), 3.71 (br. s., 1H), 3.36-3.54 (m, 4H), 2.89-3.02 (m, 1H), 2.84 (s, 6H), 2.70-2.78 (m, 1H), 2.64 (s, 6H), 2.11-2.33 (m, 5H), 1.59-1.76 (m, 1H), 1.49 (m, 1H), 1.29 (s, 4H)

Example 19

Figure 3:
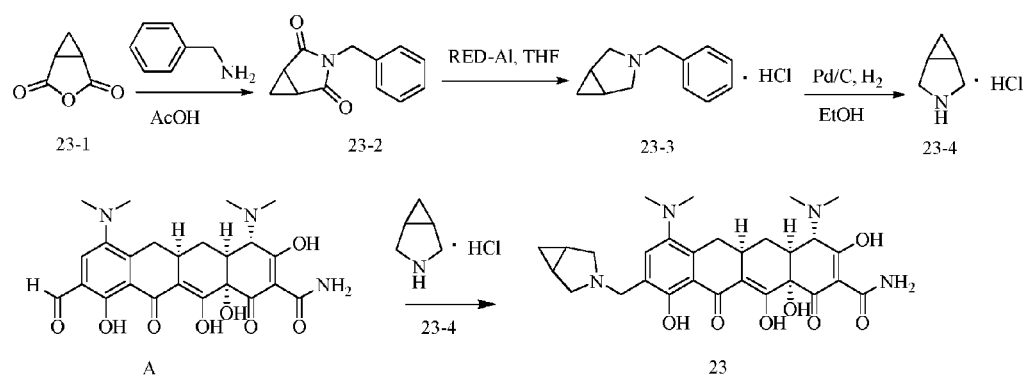
FIG. 3 is a synthetic scheme depicting a method for preparing Compound 23.

Preparation of (4S,4aS,5aR,12aS)-9-(3-azabicyclo[3.1.0]hexan-3-ylmethyl)-4,7-bis(dimethylamino)-3,10,12,12a-tetrahydroxy-1,11-dioxo-1,4,4a,5,5a,6,11,12a-octahydrotetracene-2-carboxamide (Compound 23): See FIG. 3

1) 3-benzyl-3-azabicyclo[3.1.0]hexane-2,4-dione (Compound 23-2)

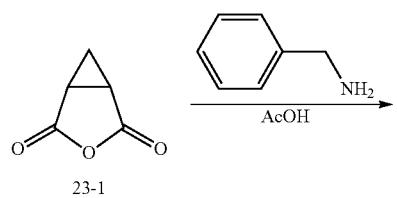

3-oxabicyclo[3.1.0]hexane-2,4-dione (23-1) (20 g, 0.179 mol) was dissolved in acetic acid (100 mL), and benzylamine (28.8 g, 0.269 mol) was added dropwise under cooling in a water bath, after the completion of addition, the temperature was raised to reflux and stirred overnight. The reaction mixture was cooled to room temperature, poured into 1 L of water to precipitate large amount of white solid, filtered, and the filter cake was recrystallized from isopropanol to give Compound 23-2 (27 g).

2) 3-benzyl-3-azabicyclo[3.1.0]hexane hydrochloride (Compound 23-3)

Sodium bis(2-methoxyethoxy)aluminum dihydride (trade name Red-Al) (70% toluene solution) (100 mL, 0.36 mol) was dissolved in 100 mL of THF under nitrogen, and a solution of Compound 23-2 (16 g, 0.08 mol) in THF (100 mL) was added dropwise under cooling with an ice bath. The mixture was stirred for 0.5 h after the completion of addition, and warmed to room temperature and stirred overnight. Water was added carefully to quench the reaction, extracted with ethyl acetate, and rotary evaporated to dryness. Ethanol was added to the concentrate to dissolve it. Hydrogen chloride-ethanol solution was added to adjust the pH to be strongly acidic, and rotary evaporated to dryness to give a white solid, washed with ethyl acetate to give a crude product of Compound 23-3 (18.5 g) and used directly in the next step reactions.

3) 3-azabicyclo[3.1.0]hexane hydrochloride (Compound 23-4)

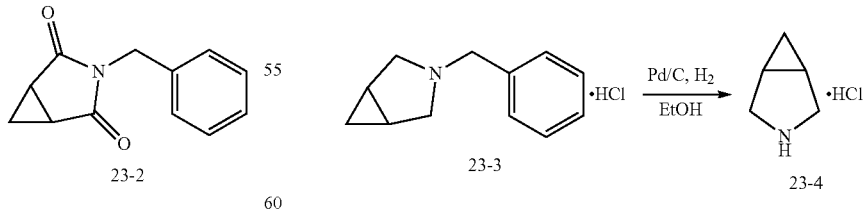

Compound 23-3 (18 g, 0.086 mol) was dissolved in 270 mL of ethanol, added 10% Pd/C (2.8 g), the atmosphere was replaced with hydrogen, followed by stirring at room temperature overnight. The reaction mixture was filtered and the filtrate was rotary evaporated to dryness to give a white solid, washed with ethyl acetate to give Compound 23-3 (9.4 g).

4) Compound 23

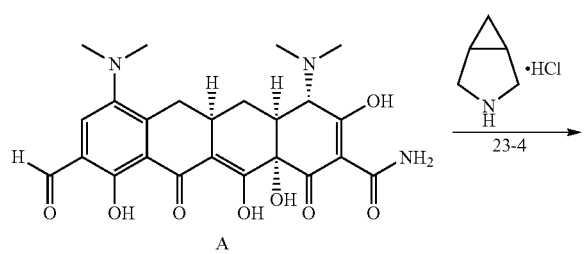

Compound A (4.85 g, 10 mmol), and 3-azabicyclo[3.1.0]hexane hydrochloride (1.43 g, 12 mmol) were dissolved in 80 mL of dichloromethane. NaBH(OAc)$_3$ (6.36 g, 30 mmol) was added portionwise at room temperature, reacted for 30 minutes after the addition. 30 mL of methanol was added to quench the reaction, and the reaction mixture was evaporated to dryness, added 100 mL of acetone and adjusted the pH to 3' with trifluoroacetic acid, filtered and added excess hydrogen chloride-ethanol solution (7 mol/L) to the filtrate until a large amount of solid precipitated, then filtered and dried to give 5 g of solid. The solid was separated by a reverse-phase column to give 0.8 g of a crude product, and further purified by a reverse-phase column to give Compound 23 (0.5 g).

$^1$H-NMR (CD$_3$OD, 400 MHz) δ: 7.42 (s, 1H), 3.93-4.05 (Abq, 2H), 3.23-3.35 (m, 3H), 3.16 (s, 1H), 2.92-3.06 (m, 2H), 2.73-2.84 (m, 1H), 2.59 (s, 6H), 2.55 (s, 6H), 2.53-2.61 (m, 1H), 1.96-2.07 (m, 2H), 1.52-1.63 (m, 3H), 0.81-0.86 (m, 1H), 0.54-0.61 (m, 1H)

5) Hydrochloride of Compound 23

Compound 23 (0.3 g) was added into a single-neck flask, and added 4.5 mL of acetone, further added dropwise excess hydrogen chloride-ethanol solution (7 mol/L) under cooling in an ice bath until a large amount of white solid precipitated. Stirring was further continued for 15 min, filtered, rinsed with 2 mL of acetone, dried to give 0.28 g of hydrochloride of Compound 23.

$^1$H-NMR (CD$_3$OD, 400 MHz) δ: 7.52 (s, 1H), 4.30-4.45 (m, 2H), 3.62 (br. s., 1H), 3.56 (m, 4H), 3.36 (m, 1H), 2.77-3.02 (m, 6H), 2.69 (m, 1H), 2.58 (s, 6H), 2.09-2.26 (m, 2H), 1.83 (m, 1H), 1.52-1.70 (m, 1H), 0.90 (m, 2H), 0.82 (m, 1H), 0.52-0.63 (m, 1H)

Example 20

Preparation of (4S,4aS,5aR,12aS)-9-(3-azabicyclo[3.1.1]heptan-3-ylmethyl)-4,7-bis(dimethylamino)-3,10,12,12a-tetrahydroxy-1,1'-dioxo-1,4,4a,5,5a,6,11,12a-octahydrotetracene-2-carboxamide (Compound 24)

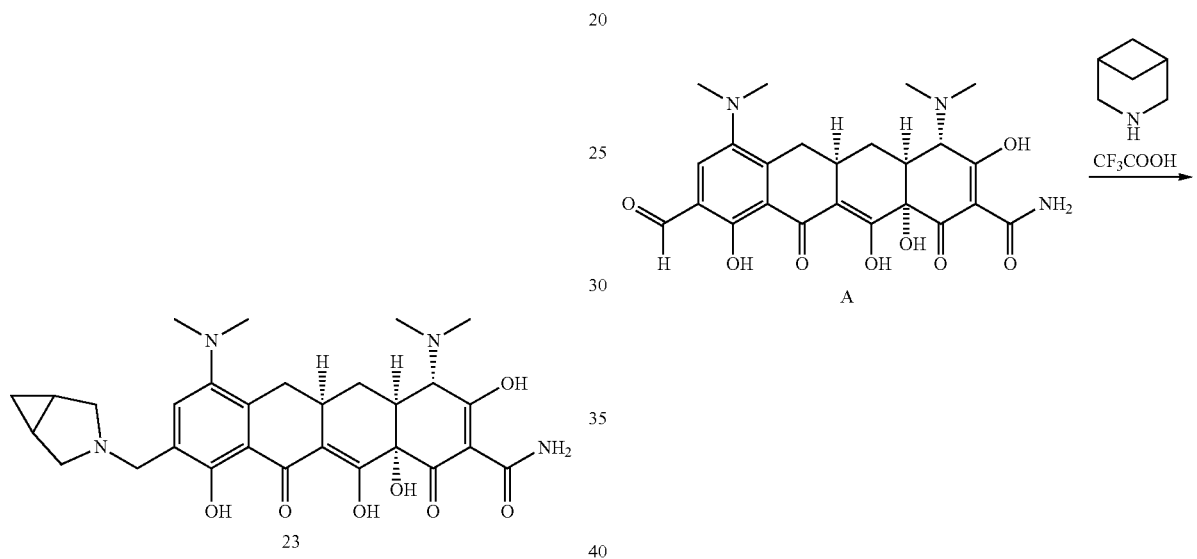

In a 25 mL single-neck flask, Compound A (0.5 g), 3-azabicyclo[3.1.1]heptane trifluoroacetate (150 mg), 1 mL TEA and 10 mg of anhydrous indium trichloride were dissolved in 10 mL of DMF and reacted at room temperature for 0.5 h. 300 mg of sodium cyanoborohydride was added slowly, and further reacted for 0.5 h. Then the reaction mixture was diluted with 1 L of water, separated by a reverse-phase column to give 300 mg of a crude product, further purified by high-pressure semi-preparative chromatographed to give Compound 24 (74 mg).

$^1$H-NMR (CD$_3$OD, 400 MHz) δ: 7.63 (s, 1H), 4.41-4.57 (m, 2H), 4.08 (s, 1H), 3.53-3.91 (m, 4H), 3.38-3.49 (m, 1H), 2.92-3.06 (m, 8H), 2.59-2.70 (m, 6H), 2.53 (m, 2H), 2.08-2.32 (m, 2H), 1.55-1.75 (m, 1H), 1.23-1.40 (m, 4H)

Example 21

Preparation of (4S,4aS,5aR,12aS)-9-((6-amino-3-azabicyclo[3.1.0]hexan-3-yl)methyl)-4,7-bis(dimethylamino)-3,10,12,12a-tetrahydroxy-1,1'-dioxo-1,4,4a,5,5a,6,11,12a-octahydrotetracene-2-carboxamide hydrochloride (the hydrochloride of Compound 26)

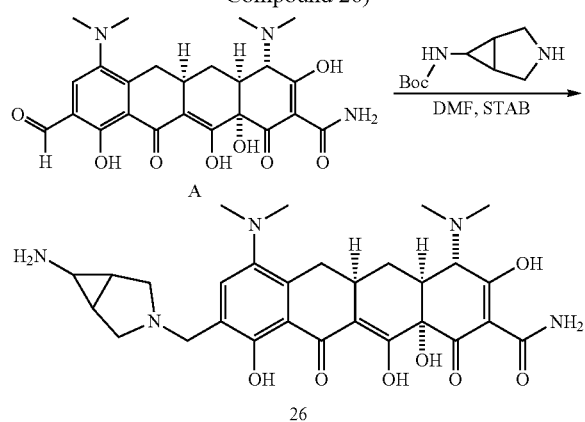

In a 25 mL single-neck flask, Compound A (1 g) and tert-butyl 3-azabicyclo[3.1.0]hexan-6-ylcarbamate (1 g) were dissolved in 5 mL of DMF, and reacted at room temperature for 0.5 h, 1.4 g of sodium triacetoxy borohydride was added slowly, and further reacted for 0.5 h. Then the reaction solution was mixed with 10 g of C18 fillers, packed into a column, separated by a quick preparative chromatography of ISCO (acetonitrile:water=1-10:100), collected the fraction which was confirmed by thin layer chromatography (TLC) to contain Compound 26. 10 mL of concentrated hydrochloric acid was added and stirred at room temperature for 0.5 h. After enrichment, the mixture was concentrated and freeze-dried to give hydrochloride of Compound 26 (58 mg, pale yellow powder).

$^1$H NMR (D$_2$O, 400 MHz) δ: 7.93 (s, 1H), 4.50 (m, 3H), 3.97 (s, 1H), 3.67 (br, 2H), 3.18 (s, 6H), 2.86-3.09 (m, 10H), 2.49 (t, 1H), 2.32 (s, 2H), 2.17 (d, 2H), 1.58 (m, 1H)

Example 22

Preparation of (4S,4aS,5aR,12aS)-9-((6-dimethyl-3-azabicyclo[3.1.0]hexan-3-yl)methyl)-4,7-bis(dimethylamino)-3,10,12,12a-tetrahydroxy-1,1'-dioxo-1,4,4a,5,5a,6,11,12a-octahydrotetracene-2-carboxamide (Compound 27)

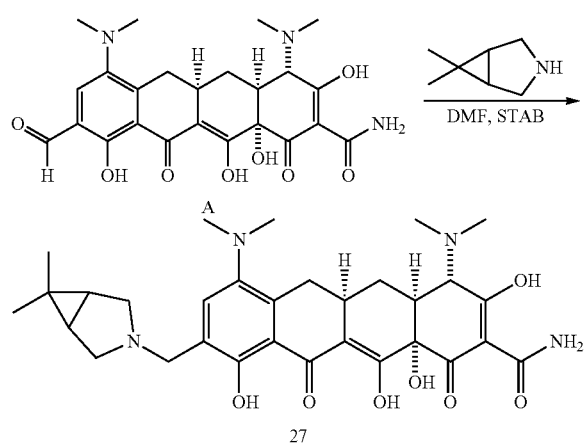

In a 25 mL single-neck flask, Compound A (1 g) and 6,6-dimethyl-3-azabicyclo[3.1.0]hexane (1 g) were dissolved in 5 mL of DMF, and reacted at room temperature for 0.5 h. 1.4 g of sodium triacetoxyborohydride was added slowly and further reacted for 0.5 h. Then the reaction solution was mixed with 10 g of C18 fillers, packed into a column, separated by a quick preparative chromatography of ISCO (acetonitrile: water=1-10:100), collected the fraction which was confirmed by thin layer chromatography (TLC) to contain Compound 27. After enrichment, the mixture was concentrated and freeze-dried to give Compound 27 (60 mg, a pale yellow powder).

LC-MS (M+1): 581 (Found)

$^1$H NMR (D$_2$O, 400 MHz) δ: 7.34 (s, 1H), 4.17 (s, 2H), 3.68 (s, 1H), 3.53 (br, 2H), 2.96 (m, 1H), 2.79 (s, 6H), 2.55-2.73 (m, 4H), 2.43 (s, 6H), 2.07-2.13 (m, 2H), 1.66 (s, 2H), 1.50-1.60 (m, 1H), 0.99 (s, 3H), 0.93 (s, 3H)

Example 23

Preparation of (4S,4aS,5aR,12aS)-4,7-bis(dimethylamino)-9-((hexahydrocyclopenta[c]pyrrol-2(1H)-yl)methyl)-3,10,12,12a-tetrahydroxy-1,1'-dioxo-1,4,4a,5,5a,6,11,12a-octahydrotetracene-2-carboxamide (Compound 28)

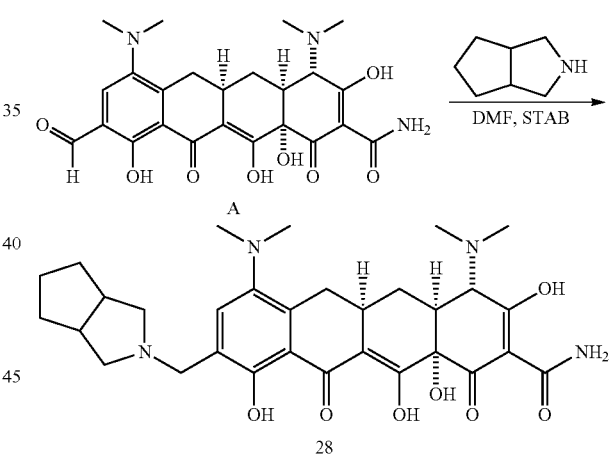

In a 25 mL single-neck flask, Compound A (1 g) and octahydrocyclopenta[c]pyrrole (1 g) were dissolved in 5 mL of DMF, and reacted at room temperature for 0.5 h. 1.4 g of sodium triacetoxyborohydride was added slowly, and further reacted for 0.5 h. Then the reaction solution was mixed with 10 g of C18 fillers, packed into a column, separated by a quick preparative chromatography of ISCO (acetonitrile: water=1-10:100), collected the fraction which was confirmed by thin layer chromatography (TLC) to contain Compound 28. After enrichment, the mixture was concentrated and freeze-dried to give Compound 28 (50 mg, a pale yellow powder).

LC-MS (M+1): 581 (Found)

$^1$H NMR (D$_2$O, 400 MHz) δ: 7.42 (s, 1H), 4.18 (s, 2H), 3.66 (s, 1H), 3.49 (br, 2H), 2.93-2.98 (m, 1H), 2.79 (s, 6H), 2.55-2.73 (m, 5H), 2.43 (s, 6H), 2.08 (t, 2H), 1.38-1.56 (m, 8H)

Example 24

Preparation of (4S,4aS,5aR,12aS)-9-((1H-isoindol-2 (3H,3aH,4H,5H,6H,7H,7aH)-yl)methyl)-4,7-bis (dimethylamino)-3,10,12,12a-tetrahydroxy-1,11-dioxo-1,4,4a,5,5a,6,11,12a-octahydrotetracene-2-carboxamide (Compound 29)

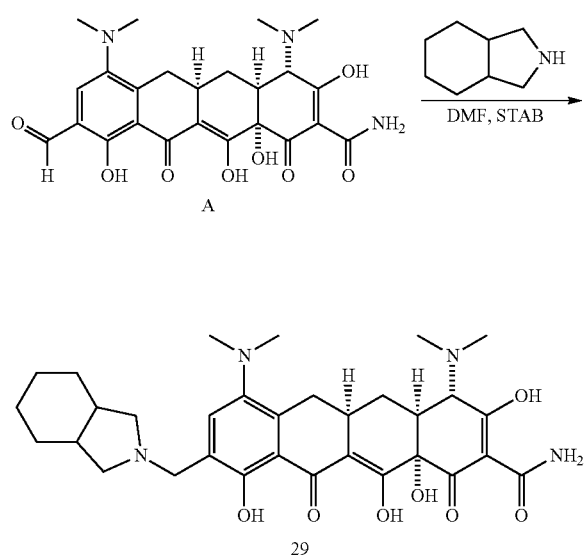

In a 25 mL single-neck flask, Compound A (1 g) and octahydro-1H-isoindole (1 g) were dissolved in 5 mL of DMF, and reacted at room temperature for 0.5 h. 1.4 g of sodium triacetoxyborohydride was added slowly, and further reacted for 0.5 h. Then the reaction solution was mixed with 10 g of C18 fillers, packed into a column, separated by a quick preparative chromatography of ISCO (acetonitrile: water=1-10:100), collected the fraction which was confirmed by thin layer chromatography (TLC) to contain Compound 29. After enrichment, the mixture was concentrated and freeze-dried to give Compound 29 (160 mg, a pale yellow powder).

LC-MS (M+1): 595 (Found)

$^1$H NMR (MeOD, 400 MHz) □δ: 7.58 (s, 1H), 4.44 (s, 2H), 3.69 (s, 1H), 3.48 (s, 2H), 3.37-3.42 (m, 2H), 2.87-2.99 (m, 1H), 2.83 (s, 6H), 2.65-2.71 (d, 1H), 2.62 (s, 6H), 2.48 (s, 2H), 2.14-2.26 (m, 2H), 1.14-1.71 (m, 10H)

The beneficial effects of the compound of the present invention will be further elaborated by the following in vitro and in vivo antibacterial experiments and pharmacokinetic experimental determination, but this should not be understood that the compound of the present invention has only the following beneficial effects.

Test Example 1

The antibacterial spectrum and in vitro antibacterial activity of the compound of the present invention Test Strains:

| Strains | Category | Source |
|---|---|---|
| G+ | Methicillin-resistant Staphylococcus aureus (MRSA) | Shanghai Renji Hosptital |
| | Methicillin-resistant Staphycoccus epidermidis (MRSE) | Shanghai Changzheng Hosptital |

-continued

| Strains | Category | Source |
|---|---|---|
| | Staphylococcus aureus | Southwest Hospital affiliated to Third Military Medical University |
| | Enterococcus faecalis | Shanghai Changzheng Hosptital |
| | Enterococcus faecium | Shanghai Renji Hosptital |
| G− | Klebsiella pneumoniae | Southwest Hospital affiliated to Third Military Medical University |
| | Escherichia coli | Southwest Hospital affiliated to Third Military Medical University |
| | Acinetobacter baumannii | Jilin Province People Hospital |
| | Klebsiella oxytoca | Jilin Province People Hospital |
| | Acinetobacter calcoaceticus | Jilin Province People Hospital |
| | Hemophilus influenzae | Southwest Hospital affiliated to Third Military Medical University |
| fastidious bacteria | Streptococus agalactiae | Beijing Chaoyang Hospital |
| | Streptococcus pyogenes | Shanghai Renji Hosptital |
| | Streptococcus constellatus | Sun Yat-Sen Memorial Hosptital |

Test Substance:

control drugs: (1) tigecycline, (2) PTK-0796, see above structural disclosed in the "Background Art" section;

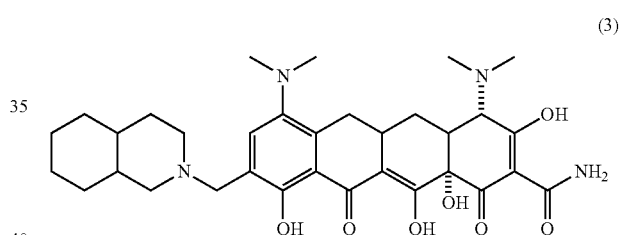

(Hereinafter referred to as Compound c),

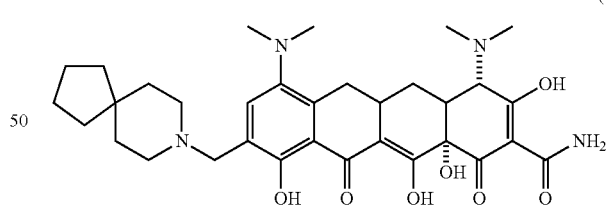

(Hereinafter referred to as Compound d),

Compound c and Compound d were prepared according to the preparation method disclosed in WO2004/064728.

The chemical names, structural formulas and preparation methods of the present compounds, see Examples.

Experimental method: the agar dilution method, with reference to Clinical And Laboratory Standards Institute. Methods for Dilution Antimicrobial Susceptibility Tests for Bacteria That Grow Aerobically; Approved Standard-Seventh Edition. CLSI Document M7-A7. Vol 26, no. 2, Wayne, Pa.: Clinical and Laboratory Standards Institute, 2006.

Experimental Results and Conclusions:

TABLE 2

| Test substances | antibacterial activity MIC (µg/mL) | | | | | |
| --- | --- | --- | --- | --- | --- | --- |
| | MRSA | MRSE | Escherichia coli | Klebsiella pneumoniae | Acinetbacter baumannii | Streptococcus pyogenes |
| PTK-0796 | 0.5 | 0.5 | 1 | 4 | 2 | 0.25 |
| Compound 2 | 0.5 | 0.25 | 1 | 4 | 0.5 | 0.125 |
| Compound 3 | 0.5 | 0.5 | 1 | 2 | 4 | 0.06 |
| Compound 10 | 1 | 0.5 | 1 | 2 | 4 | 0.125 |

TABLE 3

| Test substances | antibacterial activity MIC (µg/mL) | | | | | |
| --- | --- | --- | --- | --- | --- | --- |
| | MRSA | MRSE | Escherichia coli | Klebsiella pneumoniae | Acinetobacter baumannii | Klebsiella oxytoca |
| Compound d | 1 | 2 | 2 | 8 | 4 | 8 |
| Compound 9 | 0.5 | 0.5 | 0.5 | 1 | 4 | 1 |
| Compound 16 | 0.5 | 0.5 | 1 | 1 | 1 | 1 |
| Compound 20 | 0.5 | 1 | 0.5 | 2 | 1 | 1 |
| Compound 1 | 0.5 | 1 | 1 | 2 | 1 | 1 |
| Compound 19 | 0.5 | 0.5 | 1 | 1 | 0.25 | 0.25 |

TABLE 4

| Test substances | antibacterial activity MIC (µg/mL) | | | | | | |
| --- | --- | --- | --- | --- | --- | --- | --- |
| | MRSA | Acinetobacter baumannii | Acinetobacter calcoaceticus | Escherichia coli | Streptococus agalactiae | Klebsiella pneumoniae | Enterococcus faecalis |
| PTK-0796 | 2 | 4 | 0.5 | 4 | 0.5 | 8 | 0.25 |
| Compound c | 1 | 4 | 0.5 | 4 | 0.25 | 16 | 0.5 |
| Compound 23 | 0.25 | 1 | 0.125 | 0.25 | 0.06 | 1 | 0.06 |
| Compound 24 | 0.5 | 1 | 0.25 | 1 | 0.125 | 2 | 0.25 |
| Compound 27 | 0.5 | 0.5 | 0.125 | 2 | 0.125 | 4 | 0.125 |
| Compound 28 | 0.5 | 1 | 0.125 | 1 | 0.125 | 2 | 0.06 |
| Compound 29 | 1 | 2 | 0.25 | 1 | 0.25 | 4 | 0.125 |

TABLE 5

| Test substances | antibacterial activity $MIC_{90}$ (µg/mL) | | | | |
| --- | --- | --- | --- | --- | --- |
| | MRSA | Streptococcus constellatus | Staphylococcus aureus | Acinetobacter baumannii | Hemophilus influenzae |
| tigecycline | 1 | 0.25 | 0.5 | 4 | 0.5 |
| PTK-0796 | 2 | 0.5 | 0.5 | 8 | 1 |
| Compound 23 | 0.5 | 0.125 | 0.25 | 2 | 0.5 |

Wherein MIC represents the minimum inhibitory concentration, $MIC_{90}$ represents the 90% inhibitory concentration.

As shown in Tables 2-5, the compounds of the present invention have good activity to both Grain-positive bacteria and Grain-negative bacteria, and the antibacterial activity thereof is higher than that of the control drugs.

Test Example 2

In Vivo Pharmacokinetics Experiment of the Compounds of the Present Invention in Rats Test animals: male SD rats, weighing 230-250 g, purchased from Shanghai SLAC Laboratory Animals Co., Ltd., Certificate of Conformity: SCXK (SH) 2007-0005 22045; Six rats were tested for each compound.

Test substances: Compound 2 of the present invention, prepared in accordance with the method of Example 3; dissolved in physiological saline.

Internal standard substance: The acetonitrile solution of 50 ng/ml KBP-5747 was used as an internal standard solution in the measurement of Compound 2.

Experimental Methods:

Administration of Compound 2 of the present invention: intravenous bolus injection (iv), dose: 5 mg/kg, administrating volume: 5 mL/kg; gavage (po), dose: 5 mg/kg, administrating volume: 5 mL/kg. Prior to administration help but water fasting for 12 hours, 4 hours after administration to food.

Blood Sampling Time Point iv blood sampling time point: denoted by 0 min before administration, 5 min, 15 min, 30 min, 1 h, 2 h, 4 h, 8 h, 24 h, 30 h, 48 h after administration po blood sampling time point: denoted by 0 min before administration, 5 min, 15 min, 30 min, 1 h, 2 h, 4 h, 8 h, 24 h, 30 h, 48 h after administration Each time point to take around 150 μl whole blood, centrifugated at 2000×g at 4° C. for 5 minutes in a low-temperature high-speed centrifuge to separate plasma, the resulting plasma frozen was at −70° C. in a refrigerator.

Plasma samples analysis: 30 μl of plasma was taken and added 100 μl of internal standard solution, subjected to vortex at 14,000 rev/min for 5 minutes, then to centrifugation at 12,000 rpm/min for 5 minutes. The supernatant was taken and analyzed using LC-MS/MS.

Formula

Absolute Bioavailability $F\%=[AUC]_{INF\,(po)} \times Dose_{(iv)} / [AUC]_{INF\,(iv)} \times Dose_{(po)}$ Experimental Results and Conclusions

TABLE 6

The evaluation results of pharmacokinetics of the present compound (iv)

| Test substance | dose (mg/kg) | $AUC_{inf}$ (ng/mL/h) | Vss (L/kg) | $T_{1/2}$ (h) | CL (L/kg/h) |
|---|---|---|---|---|---|
| Compound 2 | 5 | 2293 | 5.12 | 4.07 | 2.23 |

TABLE 7

The evaluation results of pharmacokinetics of the present compound (po) in rats

| | dosage (mg/kg) | $AUC_{inf}$ (ng/mL/h) | $C_{max}$ (ng/mL) | $T_{max}$ (h) | $T_{1/2}$ (h) | F % |
|---|---|---|---|---|---|---|
| Compound 2 | 5 | 777 | 251 | 1.00 | 2.32 | 33.9 |

$AUC_{inf}$ represents the area under the plasma concentration versus time curve from zero to infinity;
CL represents the plasma clearance;
Vss represents the apparent volume of distribution;
$T_{1/2}$ represents the half-life;
$T_{max}$ represents the time to maximum plasma concentration;
$C_{max}$ represents the maximum plasma concentration;
F % represents the absolute bioavailability.

Tables 6 and 7 show that the compounds of the present invention have good pharmacokinetics property and high bioavailability, and therefore have great clinical value.

Test Example 3

In Vivo Pharmacokinetic Experiment of the Present Compound in Rats

Test animals: male SD rats, weighing 180-280 g, purchased from Beijing Vital River Laboratory Animal Technology Co., Ltd.; animal Certificate of Conformity: SCXK (Beijing) 2006-0009. Six rats were tested for each compound.

Test Substances:

the compounds of the present invention, prepared in accordance with the methods of above Examples, dissolved in physiological saline.

tigecycline, dissolved in physiological saline.

Internal Standard Substances:

The methanol solution of 50 ng/ml alogliptin was used as an internal standard solution in the measurement of Compound 9.

The 0.1% formic acid-methanol solution of 50 ng/ml alogliptin was used as an internal standard solution in the measurement of Compound 20.

The methanol solution of 20 ng/ml alogliptin was used as an internal standard solution in the measurement of Compound 23.

The methanol solution of 200 ng/ml alogliptin was used as an internal standard solution in the measurement of tigecycline.

Experimental Methods

Administration of the compounds of the present invention: intravenous bolus injection (iv), dose: 5 mg/kg, administrating volume: 5 mL/kg; gavage (po), dose: 5 mg/kg, administrating volume: 5 mL/kg.

Administration of tigecycline: gavage (po), dose: 10 mg/kg, administrating volume: 5 mL/kg.

Prior to administration help but water fasting for 16 hours, 4 hours after administration to food.

Blood Sampling

Compound 9: iv blood sampling time point: denoted by 0 min before administration, 5 min, 15 min, 30 min, 1 h, 2 h, 4 h, 8 h, 24 h, 30 h after administration; po blood sampling time point: denoted by 0 min before administration, 5 min, 15 min, 30 min, 1 h, 2 h, 4 h, 8 h, 24 h, 30 h after administration;

Compound 20: iv blood sampling time point: 5 min, 15 min, 30 min, 1 h, 2 h, 4 h, 8 h, 24 h, 30 h after administration; po blood sampling time point: 10 min, 30 min, 1 h, 2 h, 4 h, 8 h, 24 h, 30 h after administration;

Compound 23: iv blood sampling time point: denoted by 0 min before administration, 5 min, 15 min, 30 min, 1 h, 2 h, 4 h, 8 h, 24 h, 30 h, 48 h after administration; po blood sampling time point: denoted by 0 min before administration, 5 min, 15 min, 30 min, 1 h, 2 h, 4 h, 8 h, 24 h, 30 h, 48 h after administration;

Tigecycline: iv blood sampling time point: 5 min, 15 min, 30 min, 1 h, 2 h, 4 h, 6 h, 8 h after administration; po blood sampling time point: 10 min, 30 min, 1 h, 2 h, 4 h, 6 h, 8 h, 24 h after administration.

Each time point is taken around 100 μl whole blood and placed in a heparinized tube, centrifugated at 8000 rpm/min at 4° C. for 6 minutes in a low-temperature high-speed centrifuge to separate plasma, the resulting plasma was frozen at −80° C. refrigerator.

Plasma samples analysis: 20 μl of plasma was taken and added 200 μl of internal standard solution, subjected to vortex for 3 minutes, then to centrifugation at 12,000 rpm/min for 5 minutes. 100 μl of supernatant was taken and analyzed using LC-MS/MS.

Formula

Absolute Bioavailability $F\%=[AUC]_{(po)} \times Dose_{(iv)} / [AUC]_{(iv)} \times Dose_{(po)}$ Experimental results: see Tables 8 and 9.

TABLE 8

The evaluation results of pharmacokinetics of the present compounds (iv) in rats

| | dosage (mg/kg) | AUC (h × ng/mL) | Vss (L/kg) | $T_{1/2}$ (h) | CL (L/kg/h) |
|---|---|---|---|---|---|
| Compound 9 | 5 | 6071① | 4.65 | 5.85 | 0.80 |
| Compound 20 | 5 | 11592① | 2.22 | 4.98 | 0.44 |

TABLE 8-continued

The evaluation results of pharmacokinetics
of the present compounds (iv) in rats

|  | dosage (mg/kg) | AUC (h × ng/mL) | Vss (L/kg) | $T_{1/2}$ (h) | CL (L/kg/h) |
|---|---|---|---|---|---|
| Compound 23 | 5 | 9110[2] | 5.00 | 9.94 | 0.56 |
| tigecycline | 5 | 5121[2] | 4.47 | 3.8 | 0.99 |

TABLE 9

The evaluation results of pharmacokinetics
of the present compound (po) in rats

|  | dosage (mg/kg) | AUC (h × ng/mL) | $C_{max}$ (ng/mL) | $T_{max}$ (h) | F % |
|---|---|---|---|---|---|
| Compound 9 | 5 | 216[1] | 35.6 | 1.00 | 3.56 |
| Compound 20 | 5 | 605[1] | 116 | 2.00 | 5.22 |
| Compound 23 | 5 | 2003[2] | 199.4 | 1.00 | 22.0 |
| tigecycline | 10 | 296[2] | 31.8 | 0.5 | 1.8 |

[1] $AUC_{last}$ represents the area under the plasma concentration-time curve to the last measurable sampling time;
[2] $AUC_{inf}$ represents the area under the plasma concentration versus time curve from zero to infinity;
CL represents the plasma clearance;
Vss represents the apparent volume of distribution;
$T_{1/2}$ represents the half-life;
$T_{max}$ represents the time to maximum plasma concentration;
$C_{max}$ represents the maximum plasma concentration;
F % represents the absolute bioavailability.

In the third paragraph, page 2 of CENTER FOR DRUG EVALUATION AND RESEARCH APPLICATION NUMBER: 21-821 MEDICAL REVIEW(S), it was reported that tigecycline can not be absorbed in an oral use, and therefore it can be administrated only by intravenous injection. In addition, in the text of the paper on page 9, item of "PHARMACOKINETICS/TOXICOKINETICS", the pharmacokinetics of tigecycline administrated orally to a monkey was investigated and revealed tigecycline can not be absorbed in vivo when orally used. The pharmacokinetics of tigecycline administrated by intravenous injection was also investigated and the results were disclosed in page 10 of the paper as below:

| Animals | number | sex | time (h) | dosage (mg/kg) | AUC (ng × hr/mL) | $T_{1/2}$ |
|---|---|---|---|---|---|---|
| SD rats | 4 | male | 0-24 | 5(iv) | 3550 | 1.0 |

As can be seen from Table 8, the intravenous administration of the compounds of the present invention provided better pharmacokinetic indicators than that actually measured in tigecycline and the above literature values, which indicated the pharmacokinetics properties of Compounds 9, 20 and 23 of the present invention are better than that of tigecycline.

As can be seen from Table 9, when the dose of tigecycline was 2 times than the dose of the present compounds, F % of the present compounds was larger than that of tigecycline. Because "F %" is the most important indicator to measure oral medication pharmacokinetic properties, it can be seen, when administered orally, the compounds of the present invention have good pharmacokinetic properties and high bioavailability, and therefore they are suitable for oral formulations.

Test Example 4

Bactericidal Effects of the Present Compounds In Vivo in Mouse Thigh Model with *Staphylococcus aureus* Infection 1. Test Animals and Strains SPF grade CD-1 (ICR) female mice housed in SPF environment, weighing 25±2 g, purchased from Beijing Vital River Laboratory Animal Technology Co., Ltd., licensed cell No: SCXK (Beijing) 2006-0009.

*Staphylococcus aureus*: purchased from Shanghai Renji Hospital.

2. Test Substances (1) control drugs: tigecycline, PTK-0796

(2) The compounds of the present invention

3. Test Method 3.1 Neutropenia Mouse Model

Four days before bacterial infection, intraperitoneal (ip) injection of cyclophosphamide 150 mg/kg;

1 day before bacterial infection, intraperitoneal (ip) injection of cyclophosphamide 100 mg/kg;

Administration volume: 10 ml/kg.

3.2 Neutropenic Mouse Thigh Infection Model

Picked fresh *Staphylococcus aureus* single colonies which were plate cultured for 18 h, and inoculated into broth and cultured at 35° C. for 18 h. The bacterial suspension was diluted with broth, and 0.5 McFarland turbidity standard indicator bacteria suspension was prepared with a McFarland turbiditor, 10-fold diluted with broth and injected into the thigh muscle of mice in an amount of 0.1 mL for each thigh. The concentration of the bacteria suspension was about $10^6$-$10^7$ CFU/ml. The inoculum concentration was determined by an agar-plate count method.

3.3 Test Operation

Blank Group: the animals were sacrificed by dislocation at 2 h (recorded as 0 h) after the inoculation of bacteria.

Solvent group: The first administration time was set at 2 h (denoted as 0 h) after the animals were infected with bacteria, the solvent was subcutaneously administrated, the animals were sacrificed by dislocation at 24 h after the administration.

Treatment group: The first administration time was set at 2 h (denoted as 0 h). The animals were subcutaneously administrated at a dose and in a frequency as shown in Table 10, and were sacrificed by dislocation at 24 h after treatment.

The thigh muscle tissue was separated from the sacrificed animals, and 5 mL of sodium chloride injection was added, homogenated. The homogenate obtained were diluted series, taken 0.05 mL and inoculated to agar plates, two plates were inoculated in parallel for each gradient bacterial suspension, and incubated at 35° C. for 18 h. Observe the growth of the colonies on each plate, and select the plates with the number of colonies between 30-300 for colony count. The number of colonies was recorded as n1, n2. N represents the diluted fold. The number of colonies (units CFU) for each thigh was calculated according to the formula of "$(n_1+n_2)/2/0.05\times5\times N$". A logarithm to the base 10 for the number of colonies of each thigh was calculated to obtain $\log_{10}$ CFU value for each thigh.

4. Results and Discussions

The $\log_{10}$ CFU values and standard deviations for each thigh at 24 h after drug administration in different drug administrated groups are shown in Table 10 as below:

TABLE 10

| Test substances | dosage mg/kg/day | Dose times | MIC values (μg/ml) | blank group mean (0 h) | mean ± standard deviations (24 h) | change values |
|---|---|---|---|---|---|---|
| Compound 23 | 2 | 2 | 0.25 | 6.39 ± 0.07 | 7.67 ± 0.17 | 1.28 |
|  | 6 | 2 |  |  | 6.27 ± 0.41 | −0.12 |
|  | 18 | 2 |  |  | 4.35 ± 0.45 | −2.04 |

TABLE 10-continued

| Test substances | dosage mg/kg/day | Dose times | MIC values (μg/ml) | blank group mean (0 h) | mean ± standard deviations (24 h) | change values |
|---|---|---|---|---|---|---|
| tigecycline | 2 | 2 | 0.25 | | 8.02 ± 0.24 | 1.63 |
| | 6 | 2 | | | 7.02 ± 0.43 | 0.63 |
| | 18 | 2 | | | 4.20 ± 0.25 | −2.19 |
| PTK-0796 | 2 | 2 | 0.5 | | 8.16 ± 0.13 | 1.77 |
| | 6 | 2 | | | 7.59 ± 0.21 | 1.20 |
| | 18 | 2 | | | 5.34 ± 0.79 | −1.05 |
| solvent | 0 | 2 | / | | 8.93 ± 0.14 | 2.54 |

Data of Table 10 shows that when the dosage was 6 mg/kg/day, Compound 23 had bactericidal effect against *Staphylococcus aureus* in vivo in mice, it's bacteria reducing value of each thigh is 0.12, whereas the control drugs tigecycline and PTK-0796 did not show bactericidal effect, their bacteria growing values of each thigh were 0.63 and 1.20 respectively. The control drugs tigecycline and PTK-0796 did not show bactericidal effect until the dosage reached 18 mg/kg/day. From the above results, it can be concluded that the subcutaneous administration of compound 23 provided a better bactericidal effect than the control drugs tigecycline and PTK-0796 in vivo.

The invention claimed is:

1. A compound of the general formula I:

(I)

[Structure of formula I shown with substituents $R^{2a}$, $R^{2b}$, $R^3$, $R^{4a}$, $R^{4b}$, $R^5$, $R^{6a}$, $R^{6b}$, $R^7$, $R^8$, $R^{9a}$, $R^{9b}$, $R^{10}$, $R^{11}$, $R^{12}$, $R^{13a}$, $R^{13b}$]

or pharmaceutically acceptable salt, solvate or isomer thereof, wherein $R^{2a}$, $R^{2b}$, $R^3$, $R^{10}$, $R^{11}$ and $R^{12}$ are each independently hydrogen;

$R^5$, $R^{6a}$, $R^{6b}$ and $R^8$ are each independently hydrogen;

$R^7$ is $NR^{7a}R^{7b}$;

$R^{4a}$, $R^{4b}$, $R^{7a}$ and $R^{7b}$ are each independently hydrogen or $C_{1-6}$alkyl;

$R^{9a}$ and $R^{9b}$ are selected from the following:

(1) one of $R^{9a}$ and $R^{9b}$ is hydrogen and the other of $R^{9a}$ and $R^{9b}$ is selected from:

(a) cyclobutyl or 6- to 12-membered spirocyclic group, the above groups are unsubstituted or substituted by 1 to 3 substituent(s) which may be the same or different and comprise $Q^1$; or (b) cyclobutyl$C_{1-6}$alkyl or 6- to 12-membered spirocyclic group $C_{1-6}$alkyl, the above groups are unsubstituted or substituted by 1 to 3 substituent(s) which may be the same or different and selected from $Q^1$, and carbon(s) in said cyclobutyl may be replaced by 1 oxygen atom;

alternatively, (2) $R^{9a}$ and $R^{9b}$ together with the nitrogen atom to which they are attached form azetidinyl, 6- to 9-membered spirocyclic group or 6- to 9-membered saturated fused ring group, the above groups are unsubstituted or substituted by 1 to 3 $Q^2$ substituent(s) which may be the same or different, and carbon(s) in said 6- to 9-membered spirocyclic group may be replaced by 1 oxygen atom;

$Q^1$ and $Q^2$ are independently selected from halogen, amino, or $C_{1-6}$alkyl; and $R^{13a}$ and $R^{13b}$ are each independently hydrogen.

2. The compound of claim 1, or pharmaceutically acceptable salt, solvate or isomer thereof, wherein formula (I) has a structure represented by formula (II) as below:

(II)

[Structure of formula II]

wherein $R^{9a}$ and $R^{9b}$ are each independently as defined in claim 1.

3. The compound of claim 1, or pharmaceutically acceptable salt, solvate or isomer thereof, wherein formula (I) has a structure represented by formula (III) as below:

(III)

[Structure of formula III]

wherein $R^{9a}$ and $R^{9b}$ are each independently as defined in claim 1.

4. The compound of claim 1, or pharmaceutically acceptable salt, solvate or isomer thereof, wherein the compound is selected from:

[Two compound structures shown]

67
-continued
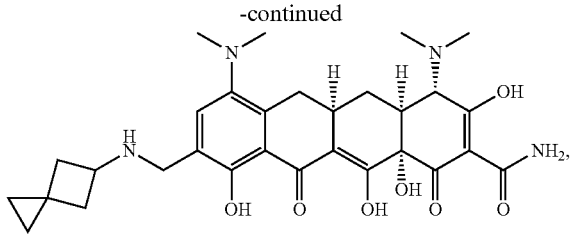
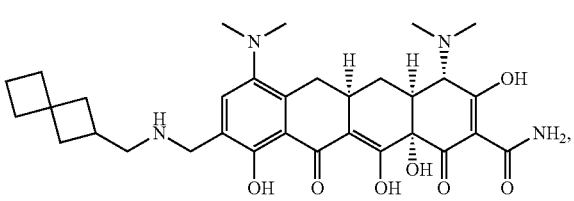
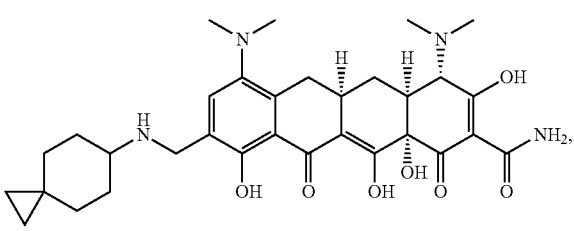
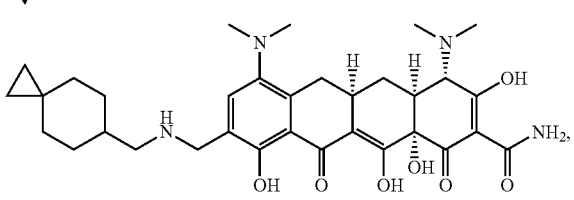
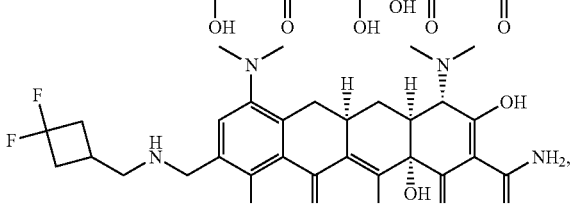
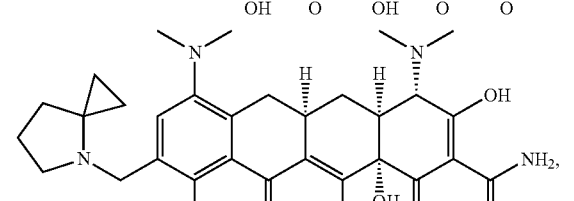
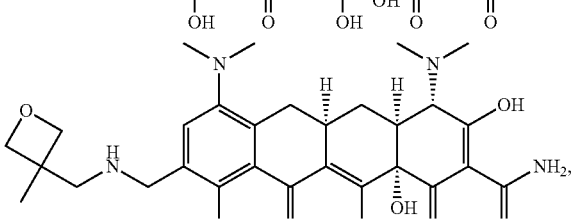
68
-continued
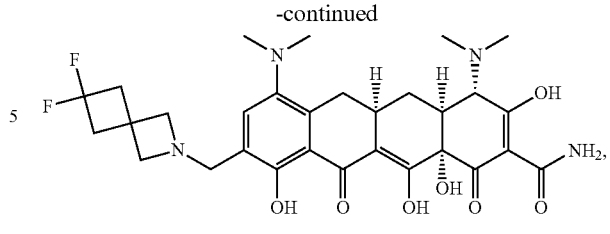
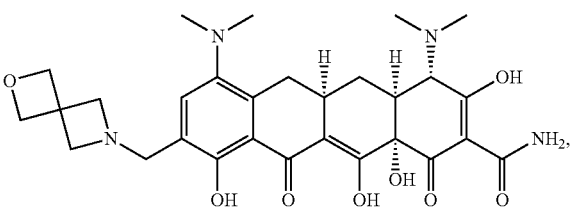
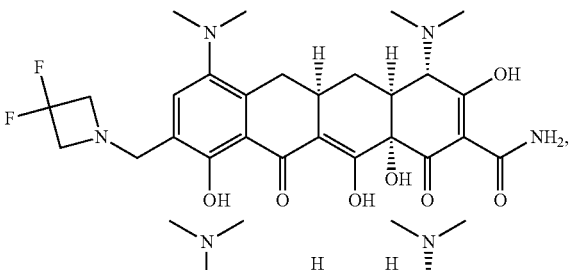
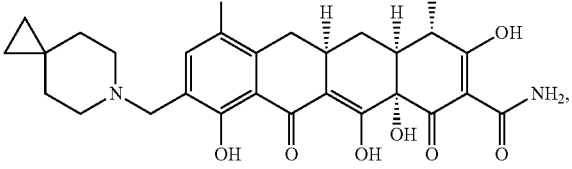
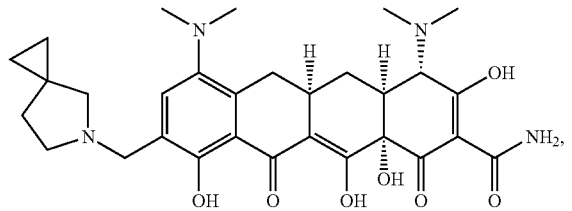
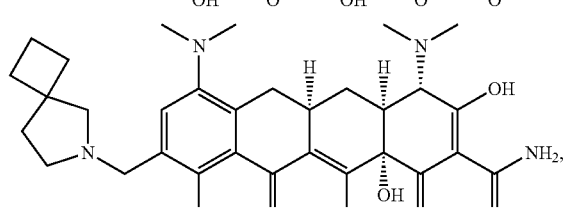
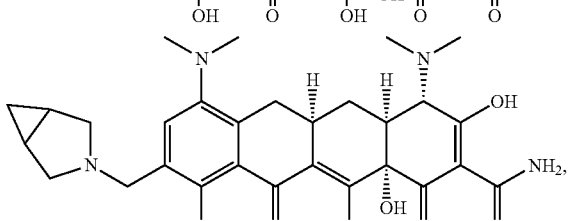

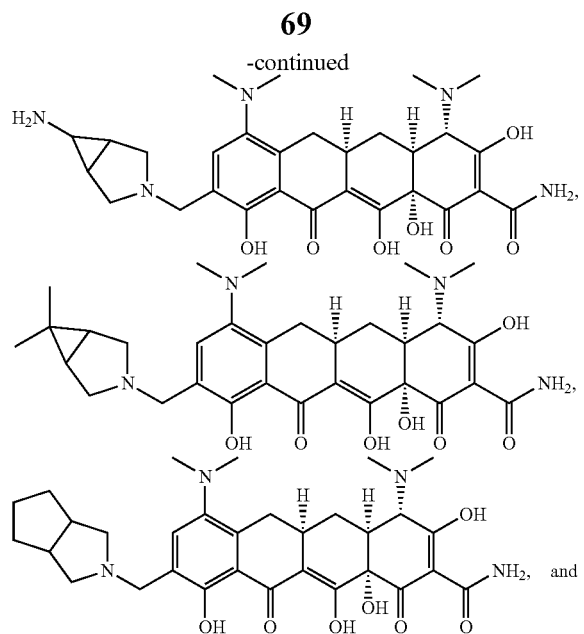

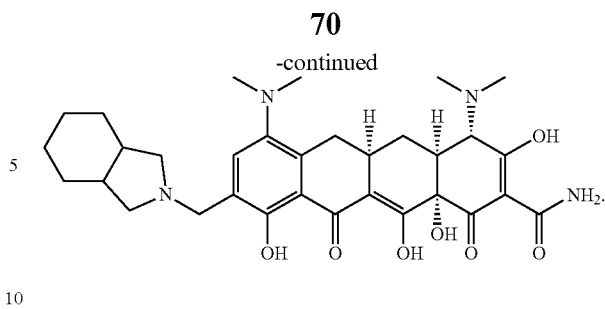

5. A pharmaceutical composition comprising the compound of claim 1, or pharmaceutically acceptable salt, solvate or isomer thereof, and a pharmaceutically acceptable carrier and/or diluent.

6. A method for treating or prophylaxis of infections, cancers, diabetes and any other diseases which have been found to be treatable and/or preventable by tetracycline compounds comprising administering to a recipient in need thereof an amount of a medicament comprising the compound of claim 1, or pharmaceutically acceptable salt, solvate or isomer thereof.

* * * * *